(12) United States Patent
Navratil et al.

(10) Patent No.: US 10,849,656 B2
(45) Date of Patent: Dec. 1, 2020

(54) IMPLANT APPLICATORS AND METHODS OF ADMINISTERING IMPLANTS

(71) Applicant: Aerie Pharmaceuticals, Inc., Bedminster, NJ (US)

(72) Inventors: Tomas Navratil, Carrboro, NC (US); Jessie Delgado, Durham, NC (US); Michael Hunter, Cary, NC (US)

(73) Assignee: Aerie Pharmaceuticals, Inc., Bedminster, NJ (US)

( * ) Notice: Subject to any disclaimer, the term of this patent is extended or adjusted under 35 U.S.C. 154(b) by 0 days.

(21) Appl. No.: 15/695,810

(22) Filed: Sep. 5, 2017

(65) Prior Publication Data

US 2018/0368886 A1 Dec. 27, 2018

Related U.S. Application Data

(63) Continuation of application No. PCT/US2016/021081, filed on Mar. 4, 2016.
(Continued)

(51) Int. Cl.
*A61F 2/06* (2013.01)
*A61B 17/34* (2006.01)
(Continued)

(52) U.S. Cl.
CPC .......... *A61B 17/3468* (2013.01); *A61F 9/007* (2013.01); *A61F 9/0017* (2013.01); *A61F 9/00736* (2013.01); *A61M 5/3202* (2013.01)

(58) Field of Classification Search
CPC ............ A61B 17/3468; A61B 17/3421; A61B 17/3478; A61F 9/0017; A61M 5/3202; A61M 25/0631; A61M 37/0069
See application file for complete search history.

(56) References Cited

U.S. PATENT DOCUMENTS 3,405,713 A 10/1968 Solowey
4,251,310 A 2/1981 Goldhaber
(Continued)

FOREIGN PATENT DOCUMENTS

WO 2015/085251 A1 6/2015
WO 2016/144832 A1 9/2016
(Continued)

OTHER PUBLICATIONS

International Search Report and Written Opinion for International Application No. PCT/US2016/043675 dated Nov. 29, 2016.
(Continued)

*Primary Examiner* — Rebecca E Eisenberg
(74) *Attorney, Agent, or Firm* — K&L Gates LLP; Louis C. Cullman; Benjamin D. Hueberger

(57) ABSTRACT

Embodiments described herein relate generally to medical implant delivery apparatuses and methods. In some embodiments, an apparatus comprises a first cap, a needle hub at least partially disposed within the first cap, a pusher wire and a pusher wire connector disposed within the needle hub, a needle and a second cap. The first cap includes a proximal end, a distal end, and a longitudinal axis. The needle includes a first, beveled end configured to receive an implant, and a second end disposed within a hub pocket of the needle hub. The second cap is connected to the needle hub and disposed at a proximal end of the first cap. The pusher wire, the pusher wire connector, and the needle are substantially aligned with one another along the longitudinal axis of the first cap. In some embodiments, the pusher wire is sized to be received in the bore of the needle.

21 Claims, 66 Drawing Sheets

Related U.S. Application Data

(60) Provisional application No. 62/129,737, filed on Mar. 6, 2015, provisional application No. 62/263,373, filed on Dec. 4, 2015, provisional application No. 62/263,396, filed on Dec. 4, 2015.

(51) Int. Cl.
*A61F 9/00* (2006.01)
*A61F 9/007* (2006.01)
*A61M 5/32* (2006.01)

(56) References Cited

U.S. PATENT DOCUMENTS

| | | | |
|---|---|---|---|
| 5,869,079 | A | 2/1999 | Wong et al. |
| 6,129,710 | A | 10/2000 | Padgett et al. |
| 2004/0151754 | A1 | 8/2004 | Ashton |
| 2004/0171598 | A1 | 9/2004 | Bingaman et al. |
| 2005/0154399 | A1 | 7/2005 | Weber et al. |
| 2005/0244467 | A1 | 11/2005 | Nivaggioli et al. |
| 2005/0244468 | A1 | 11/2005 | Huang et al. |
| 2006/0233860 | A1 | 10/2006 | Chang et al. |
| 2008/0033351 | A1 | 2/2008 | Trogden et al. |
| 2008/0071246 | A1 | 3/2008 | Nazzaro et al. |
| 2010/0124565 | A1 | 5/2010 | Spada et al. |
| 2010/0278897 | A1 | 11/2010 | Shi et al. |
| 2011/0229551 | A1 | 9/2011 | Doshi et al. |
| 2013/0138047 | A1* | 5/2013 | Takemoto ............ A61M 5/343 604/192 |
| 2013/0158561 | A1 | 6/2013 | Bhagat et al. |
| 2013/0218102 | A1 | 8/2013 | Iwase et al. |
| 2013/0253528 | A1 | 9/2013 | Haffner et al. |
| 2015/0118279 | A1 | 4/2015 | Ghebremeskel et al. |
| 2015/0209180 | A1 | 7/2015 | Prausnitz et al. |
| 2016/0067426 | A1 | 3/2016 | Ujaoney |
| 2019/0083512 | A1 | 3/2019 | Williams et al. |
| 2019/0374380 | A1 | 12/2019 | Navratil et al. |

FOREIGN PATENT DOCUMENTS

| | | |
|---|---|---|
| WO | 2017/015604 A1 | 1/2017 |
| WO | 2018/045386 A1 | 3/2018 |

OTHER PUBLICATIONS

Singaporean Search Report and Written Opinion for Singaporean Application No. 11201800538R (date of actual completion of search: Nov. 2, 2018).
Supplementary European Search Report for European Patent Application No. 16762267.9 dated Oct. 15, 2018 (8 pages).
U.S. Appl. No. 16/330,025, filed Mar. 1, 2019.
International Search Report and Written Opinion for International Application No. PCT/US2016/021081 dated Jul. 18, 2016.
International Search Report and Written Opinion for International Application No. PCT/US2017/050122 dated Nov. 16, 2017.
Singaporean Written Opinion (Second) for Singaporean Application No. 11201800538R (date of written opinion: Oct. 11, 2019).
U.S. Appl. No. 16/712,624, filed Dec. 12, 2019.

* cited by examiner

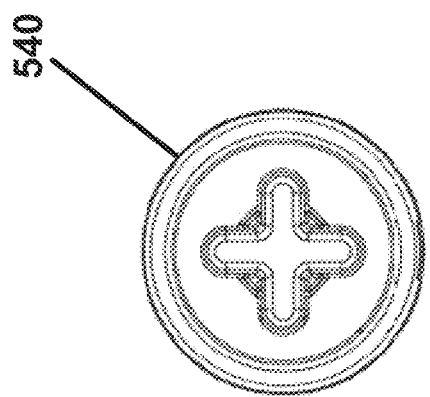
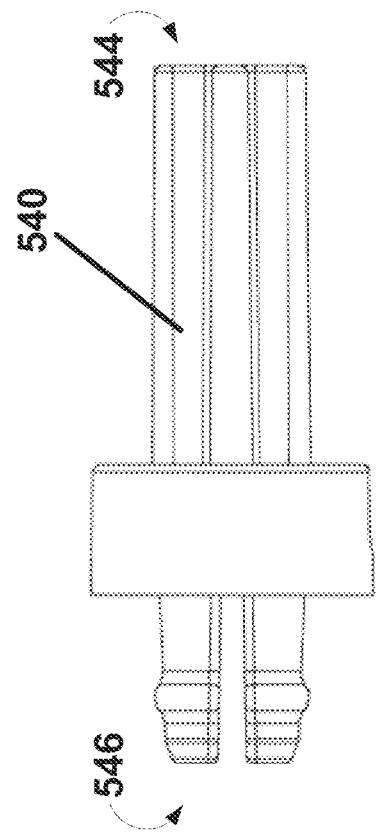
FIG. 5B
FIG. 5A

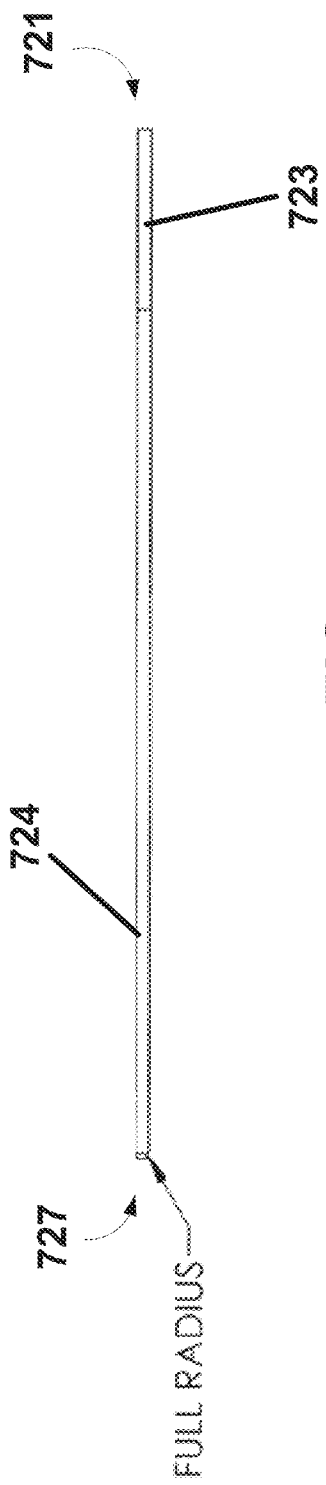

SECTION D-D

SECTION C-C

SECTION B-B

SECTION A-A

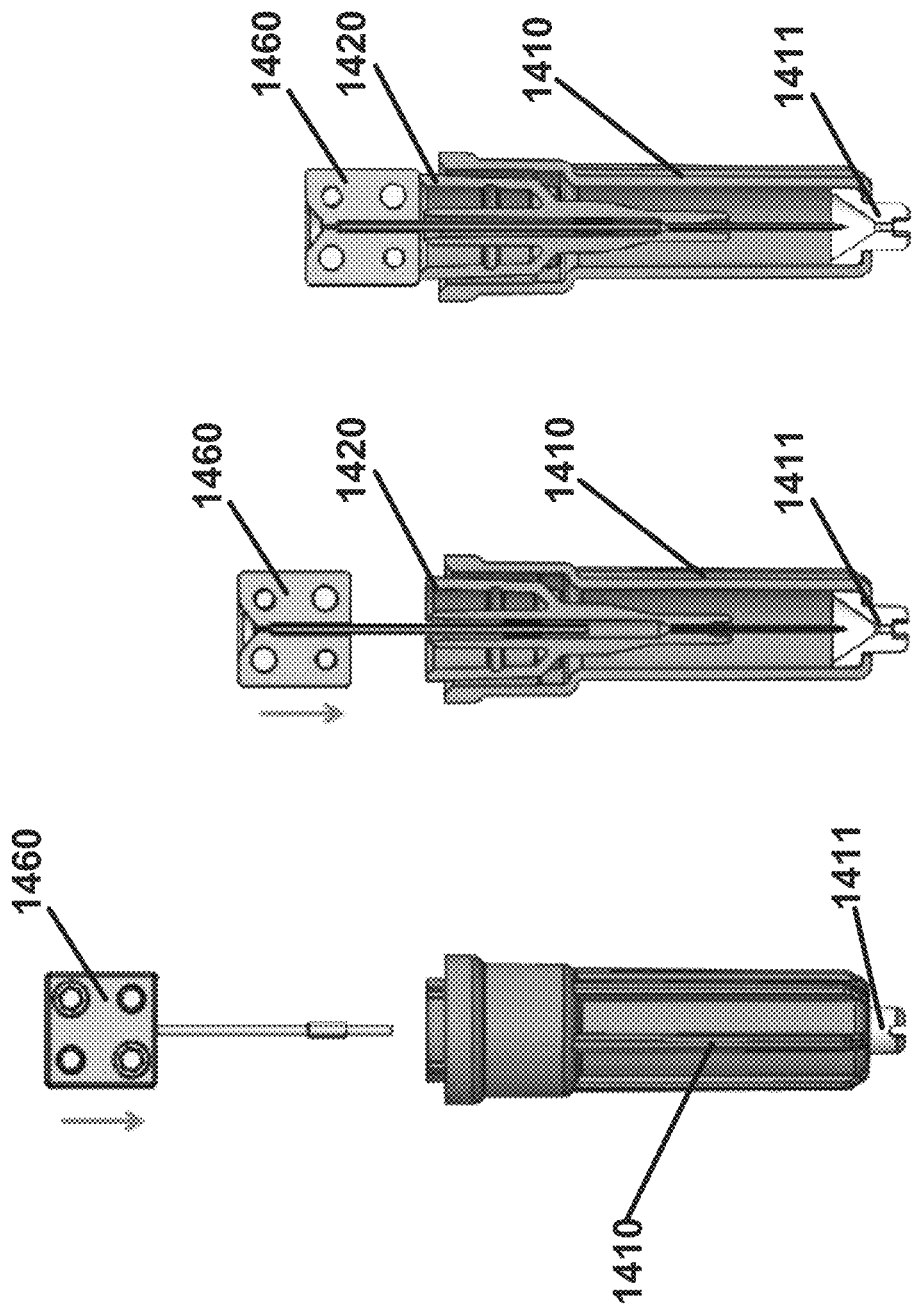

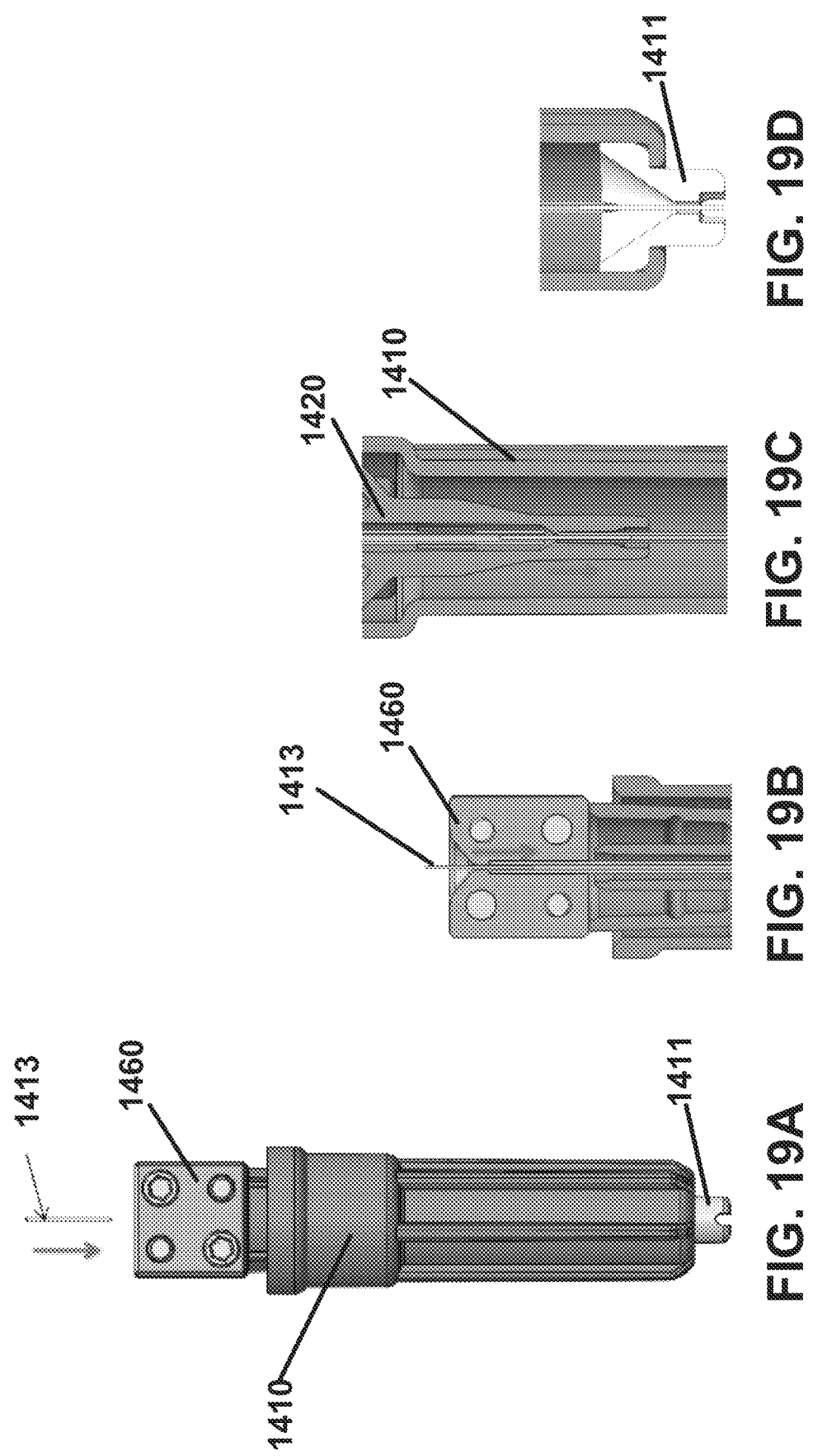

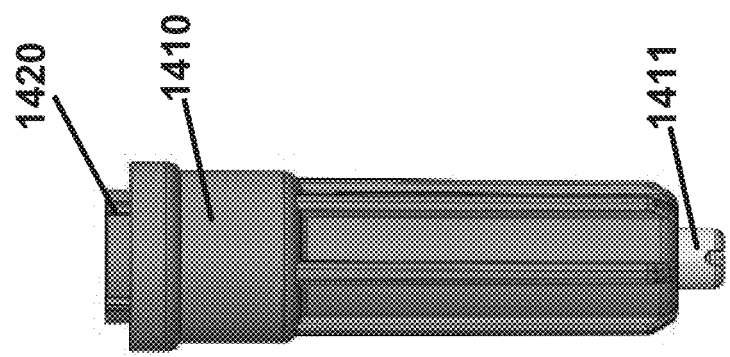
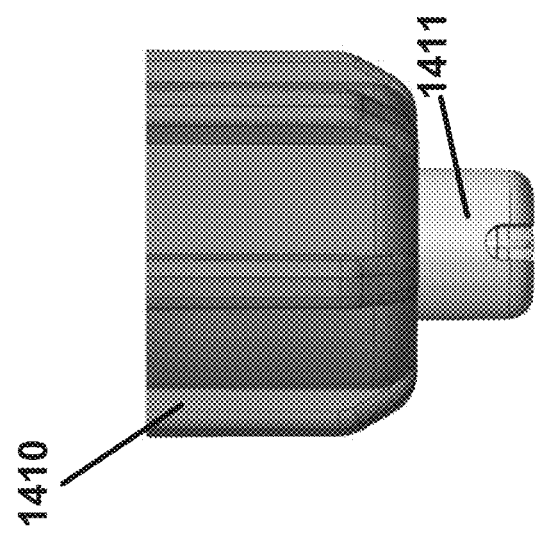
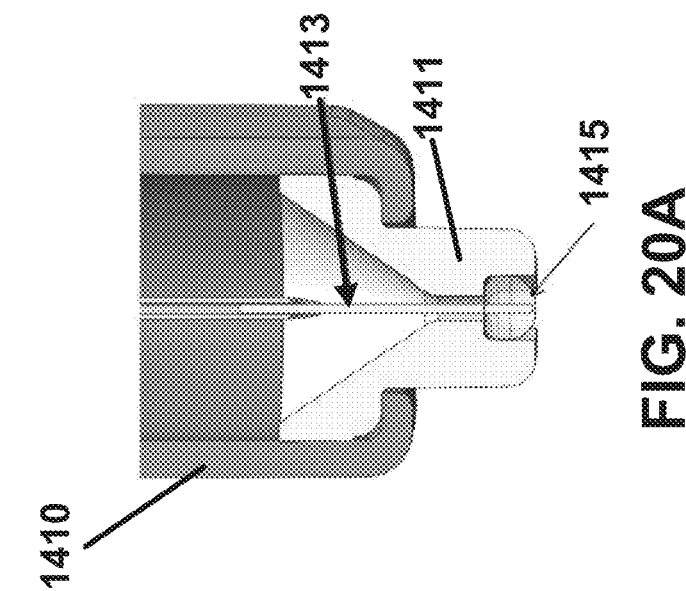
FIG. 20C
FIG. 20B
FIG. 20A

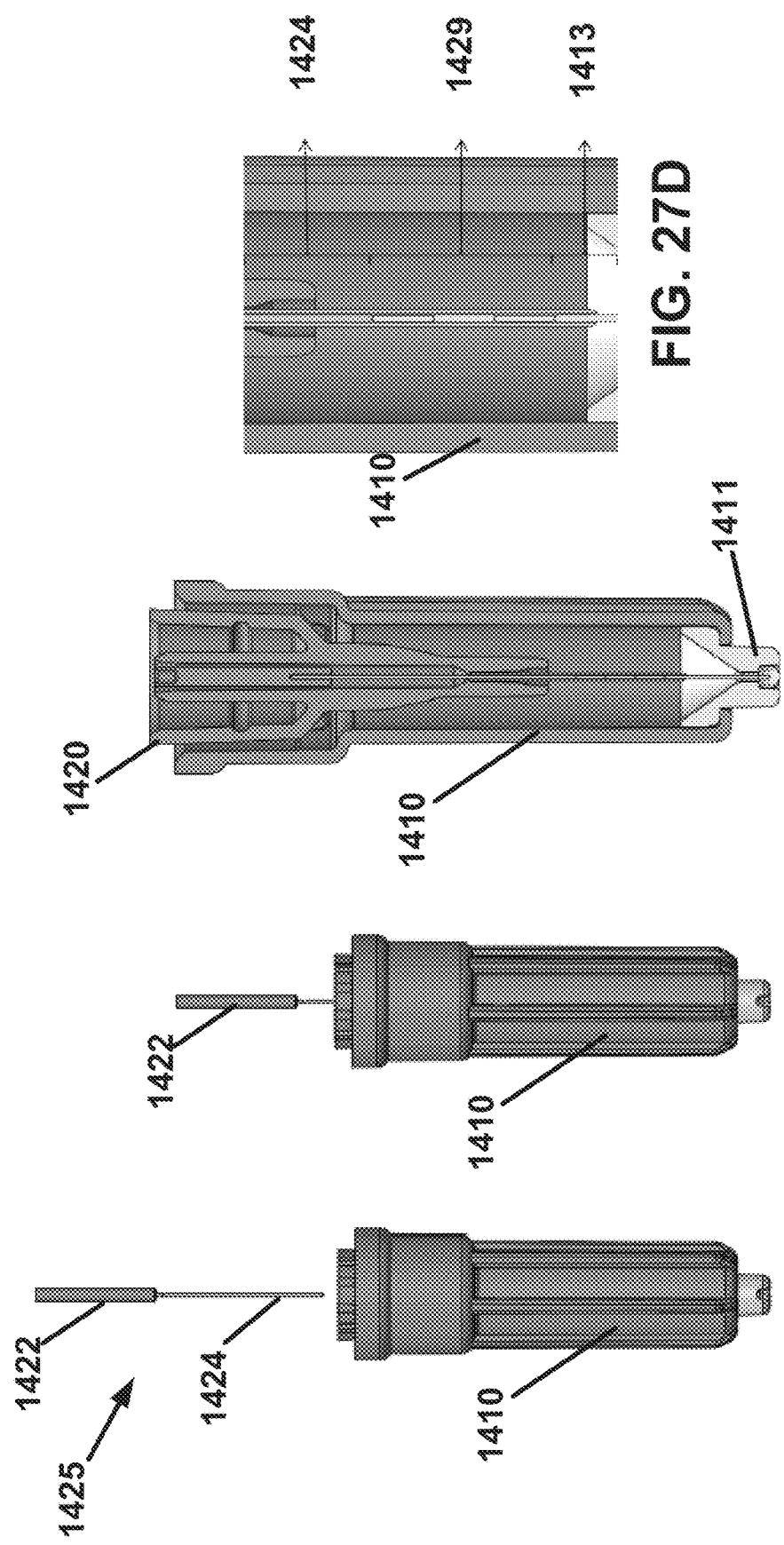

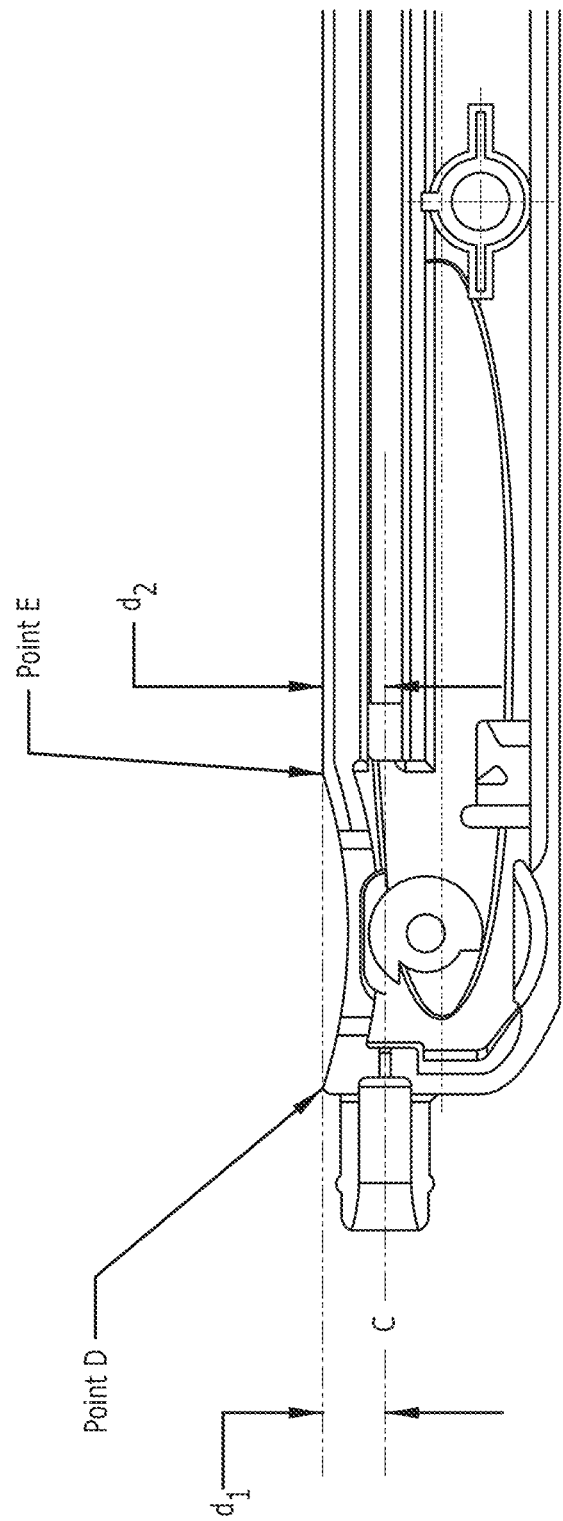

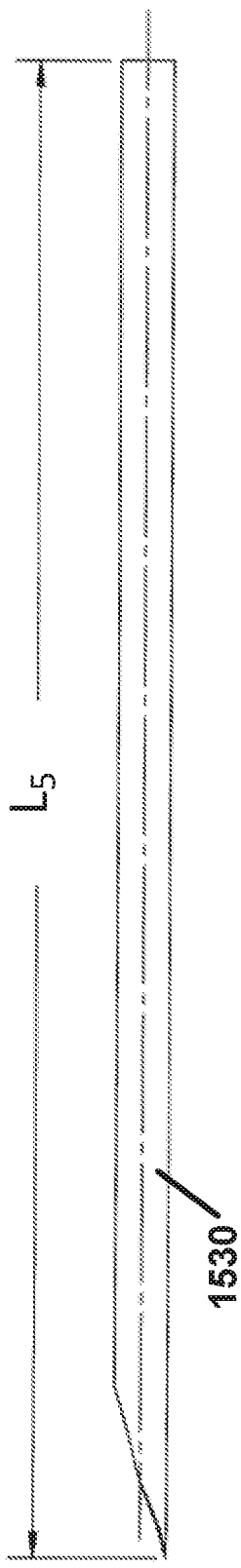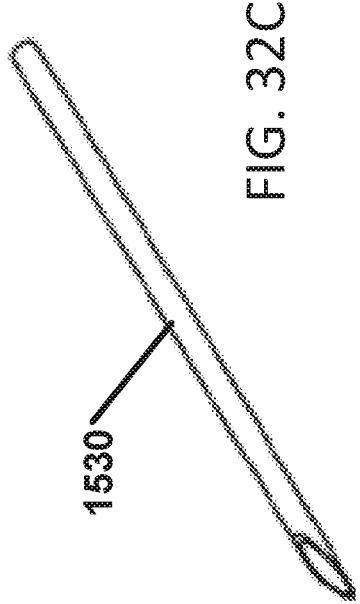
FIG. 32A
FIG. 32B
FIG. 32C

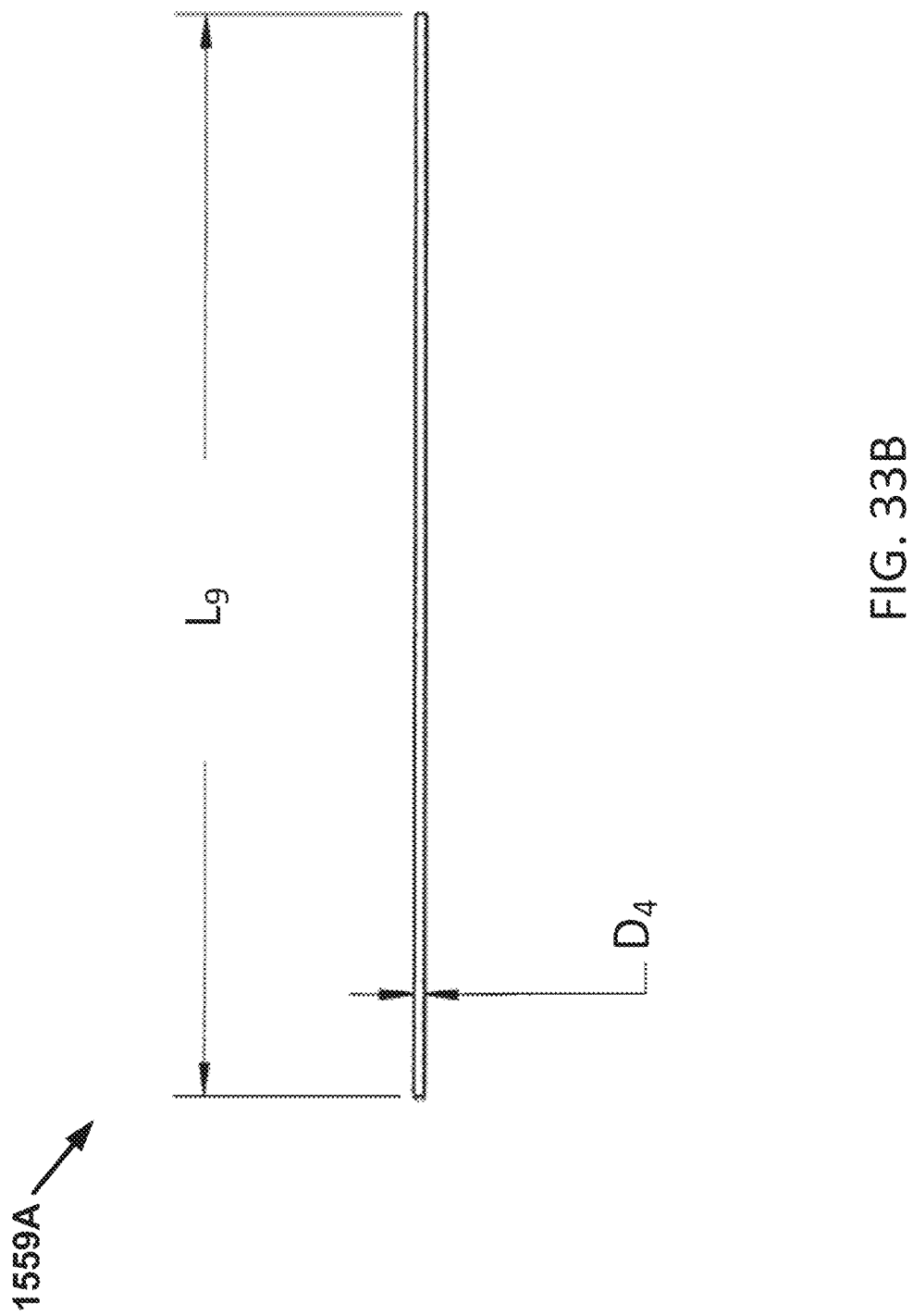

SECTION A-A

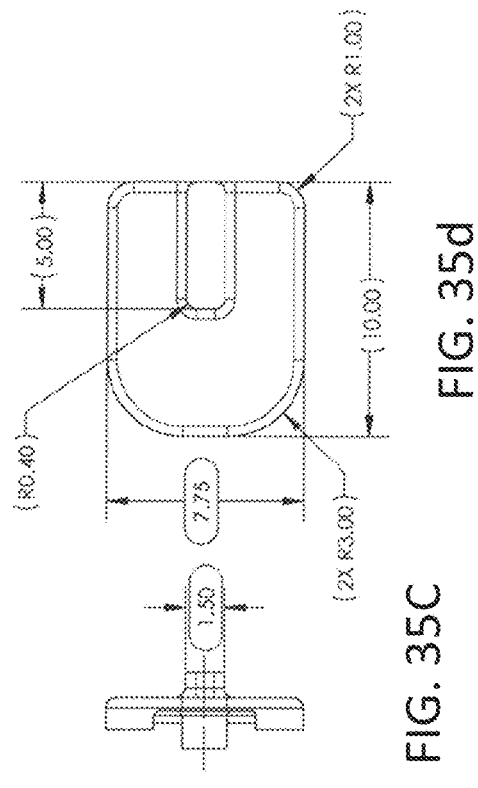
FIG. 35A
FIG. 35B
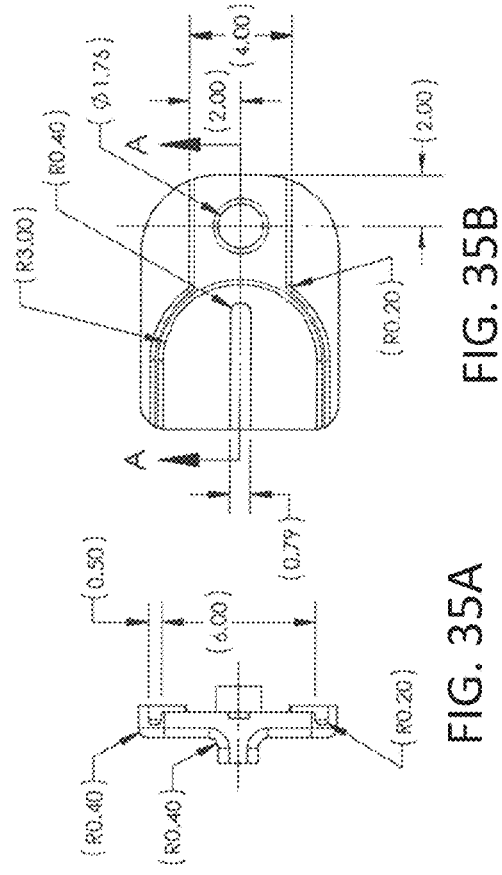
FIG. 35C
FIG. 35d
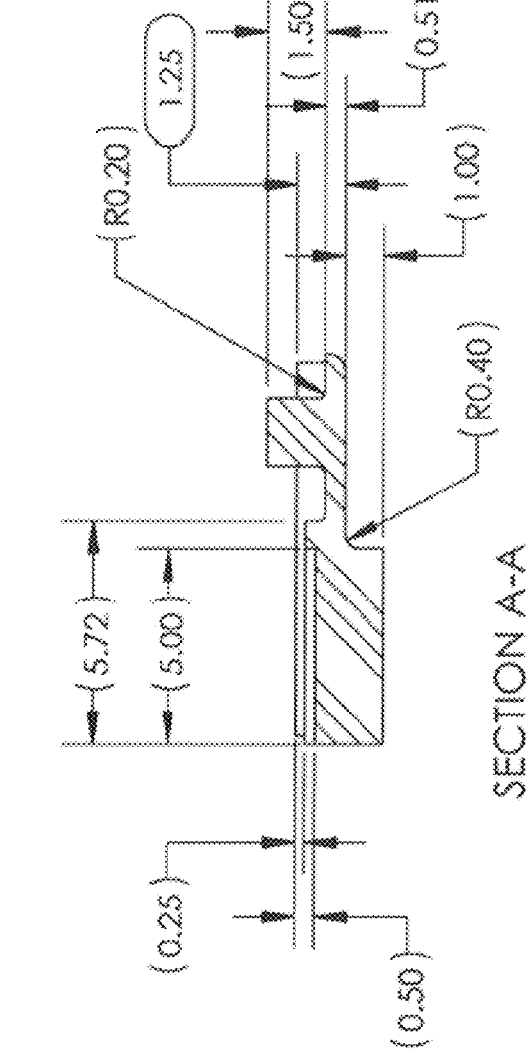
SECTION A-A
FIG. 35E

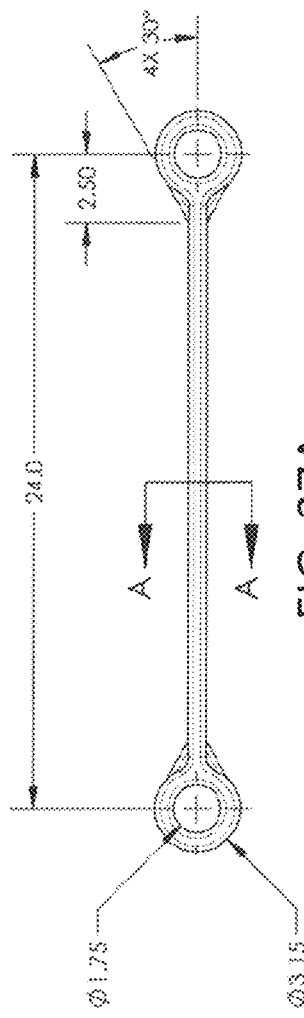
FIG. 37A
FIG. 37B
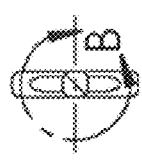
FIG. 37C
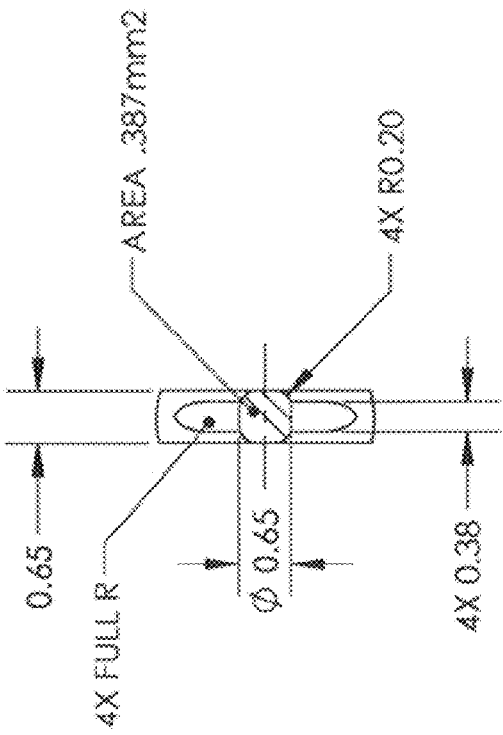
FIG. 37D

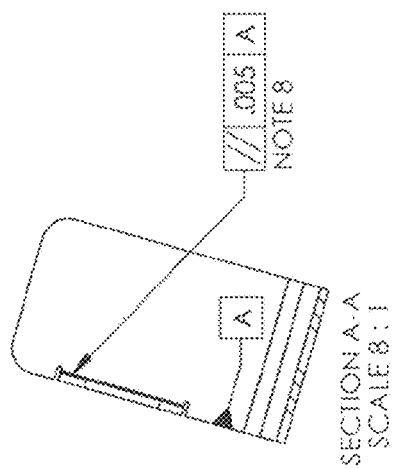
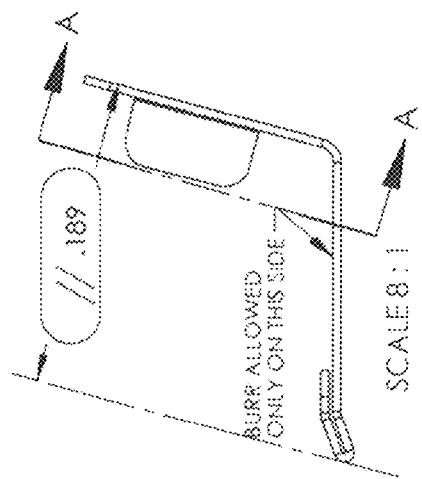
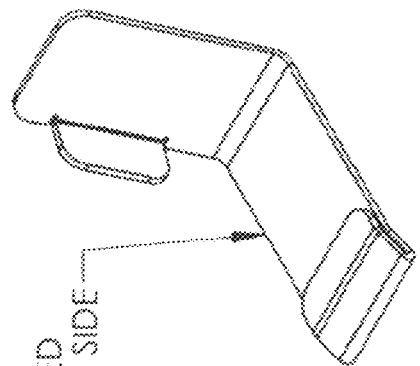
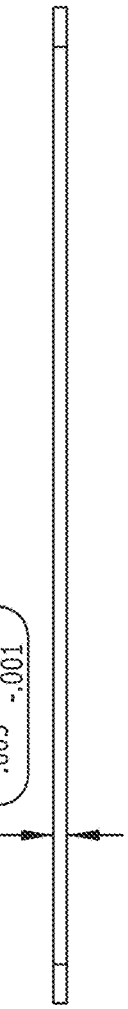
FIG. 38A
FIG. 38B
FIG. 38C
FIG. 38D

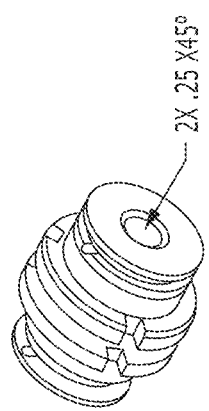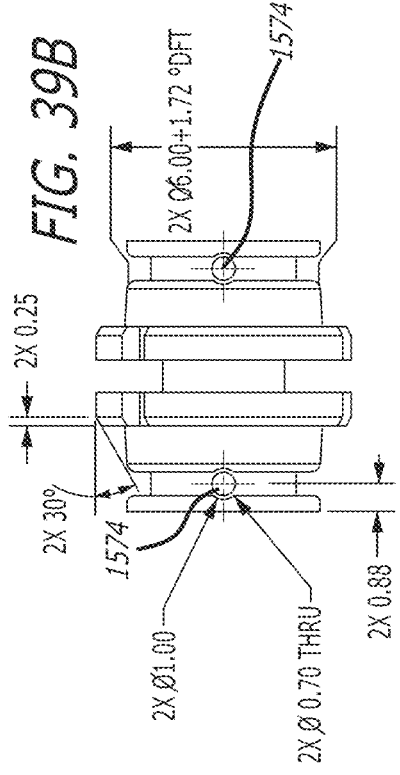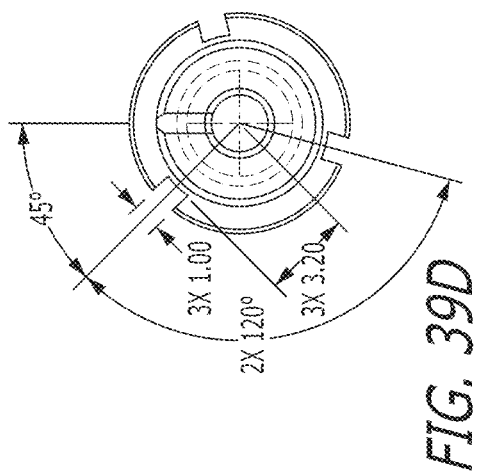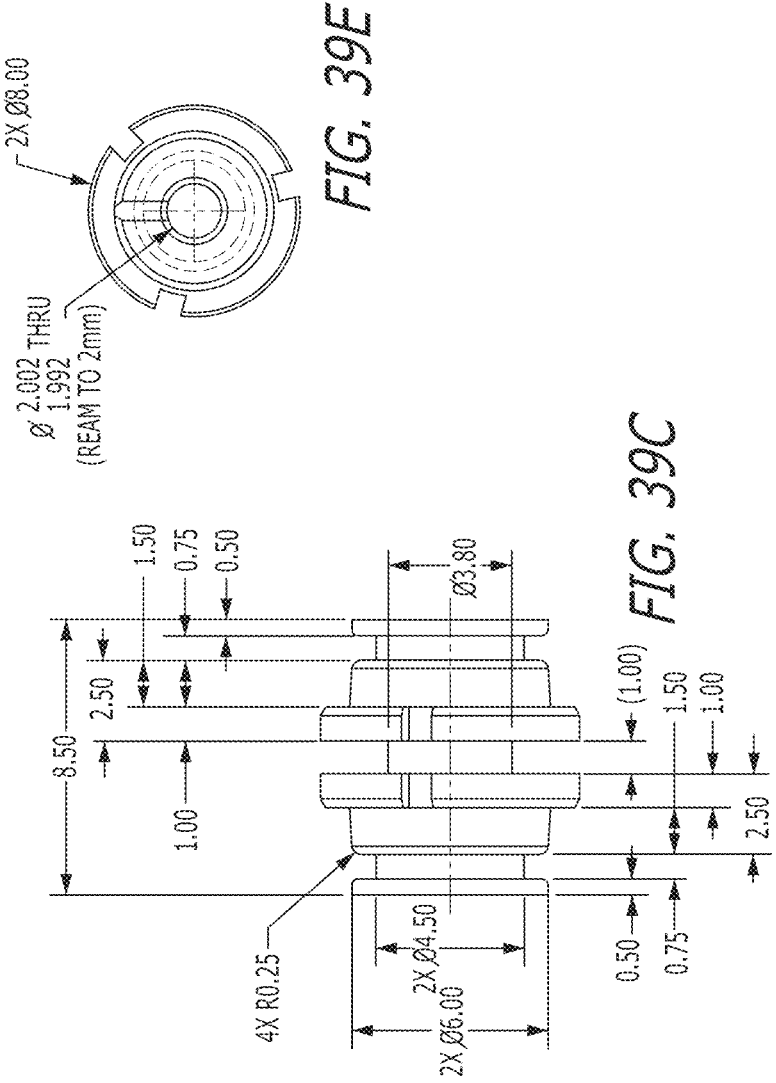

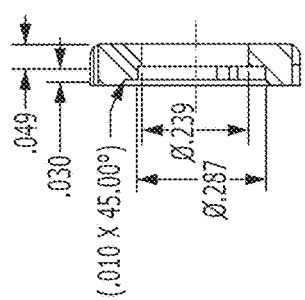
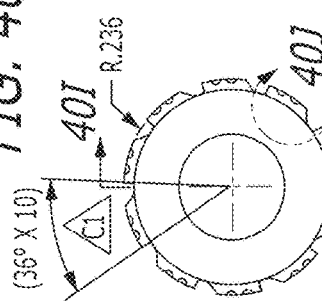
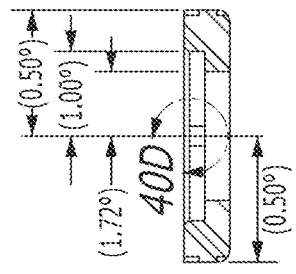
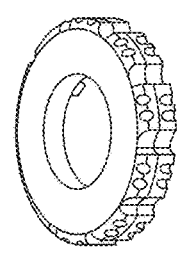
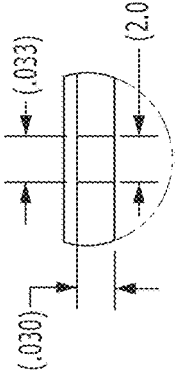
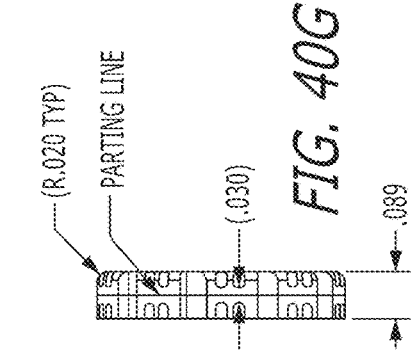
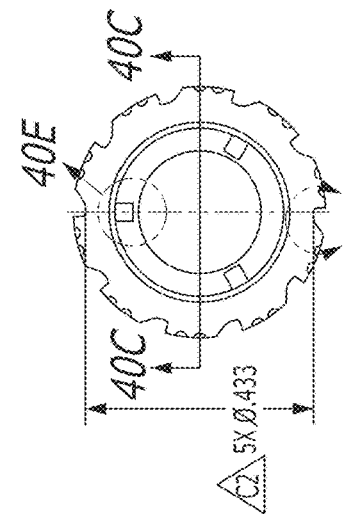
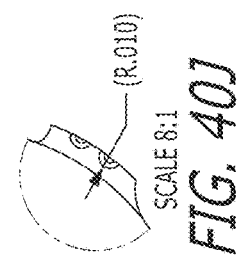
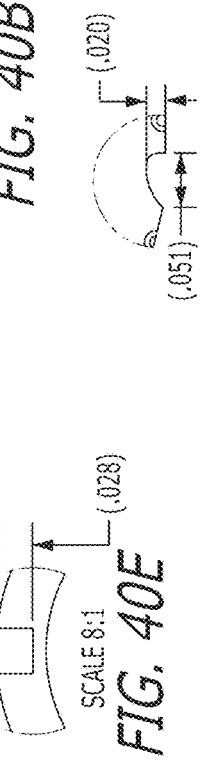
FIG. 40A  FIG. 40B  FIG. 40C  FIG. 40D  FIG. 40E  FIG. 40F  FIG. 40G  FIG. 40H  FIG. 40I  FIG. 40J

FIG. 42A
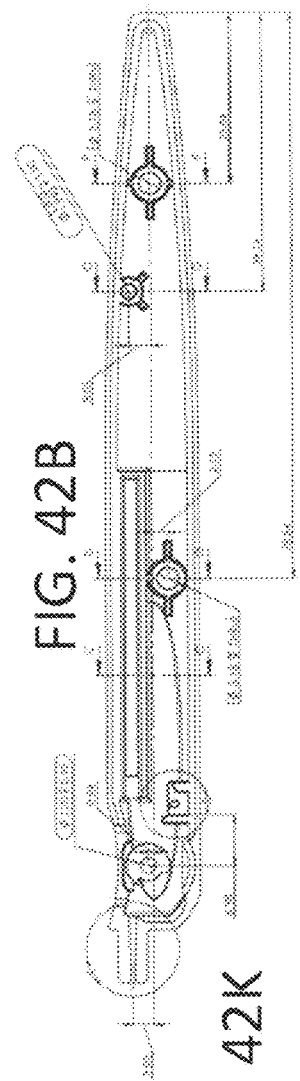
FIG. 42B
FIG. 42K
FIG. 42C
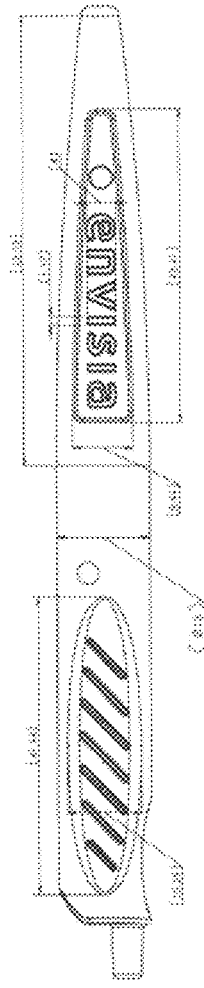
FIG. 42D
FIG. 42L

DETAIL A
SCALE 6:1

DETAIL B
SCALE 10:1

SECTION C-C
SCALE 5:1

SECTION D-D
SCALE 5:1

SECTION O-O
SCALE 5:1

SECTION P-P
SCALE 5:1

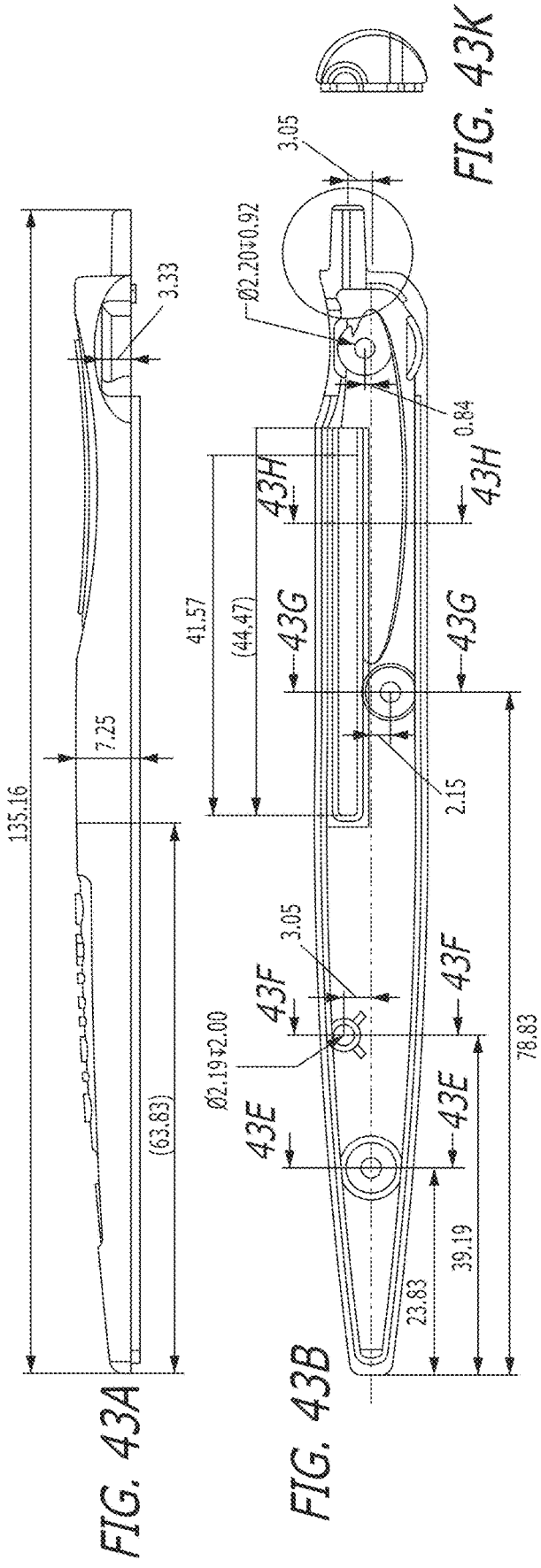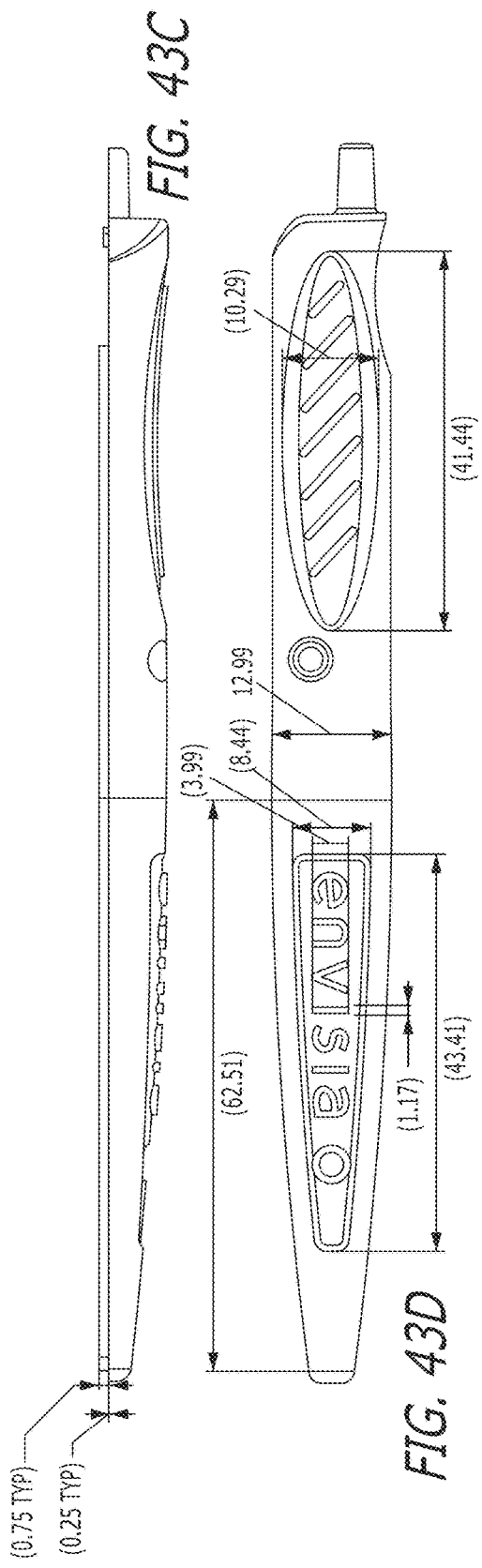

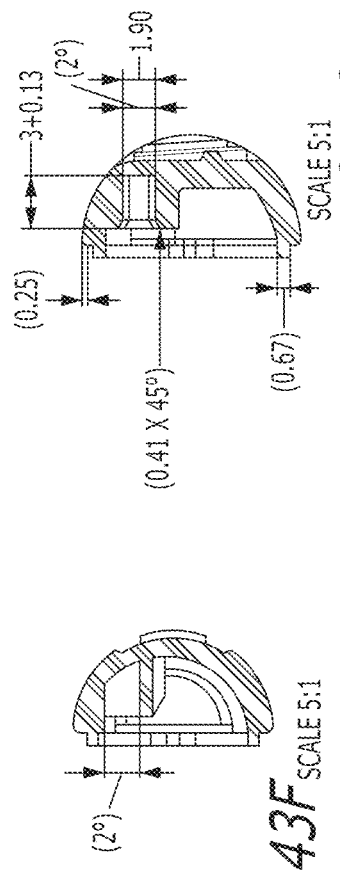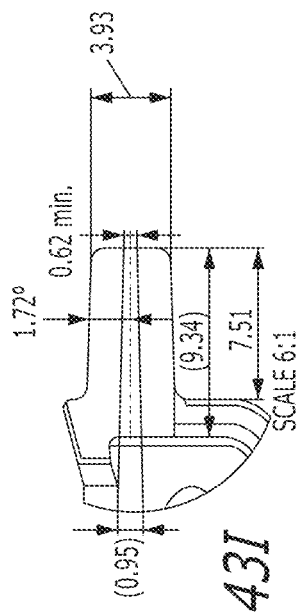

SECTION B-B
SCALE 5:1

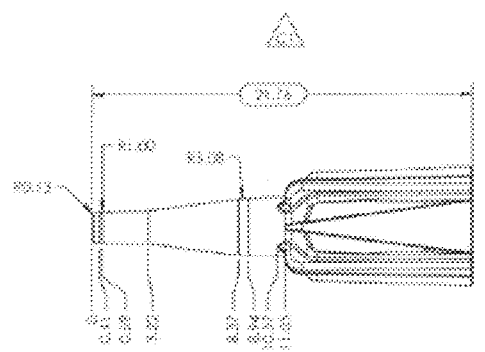
FIG. 48B
FIG. 48D
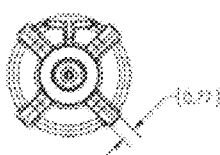
FIG. 48C
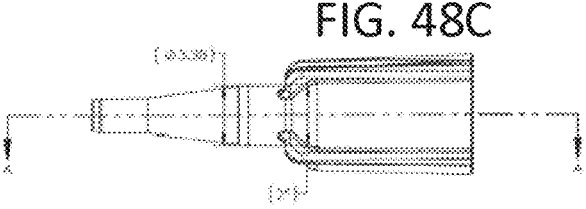
FIG. 48E
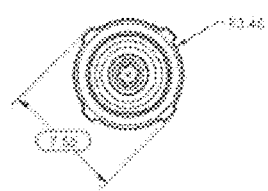
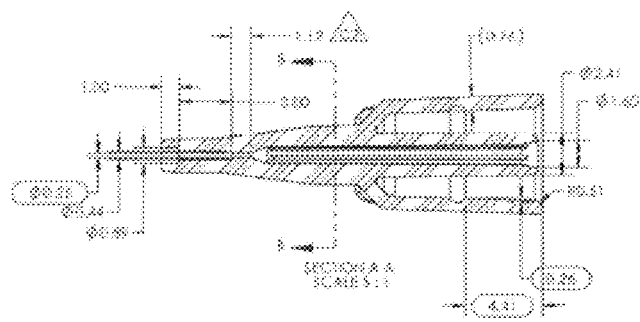
FIG. 48F

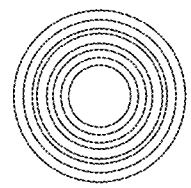
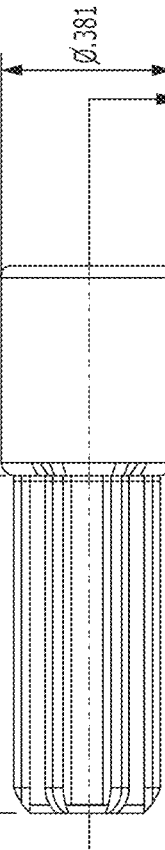
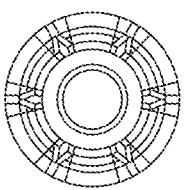
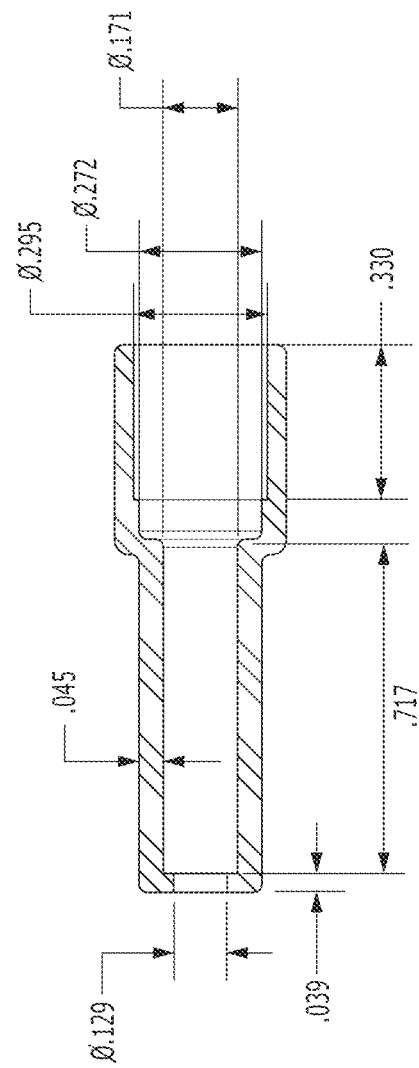
FIG. 49C
FIG. 49A
FIG. 49D
FIG. 49B

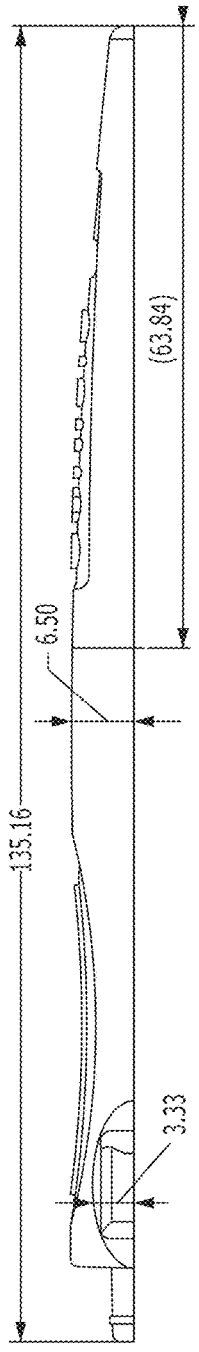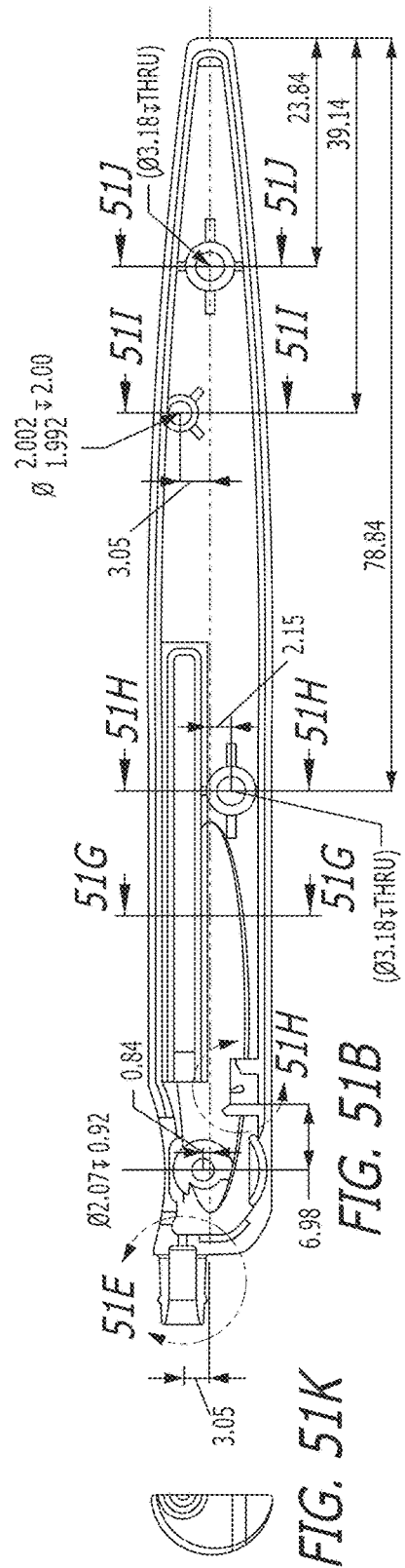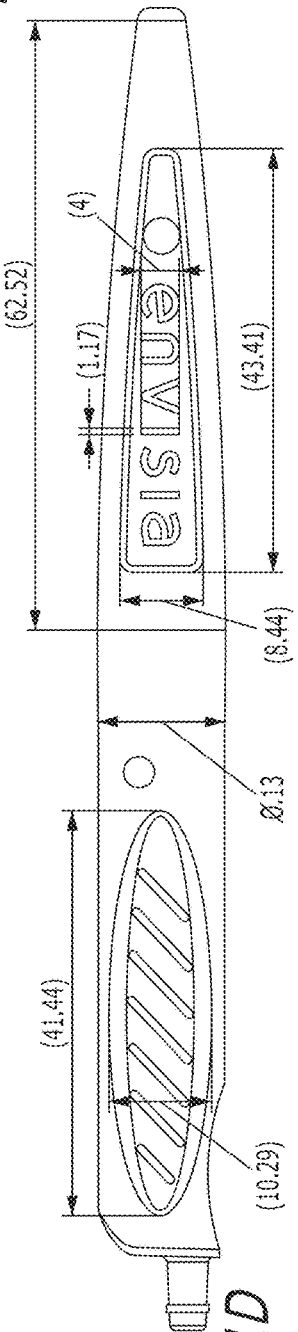
FIG. 51A  FIG. 51K  FIG. 51B  FIG. 51C  FIG. 51D  FIG. 51L

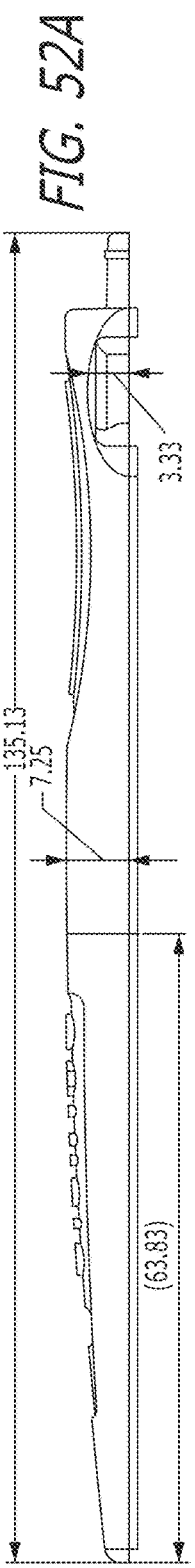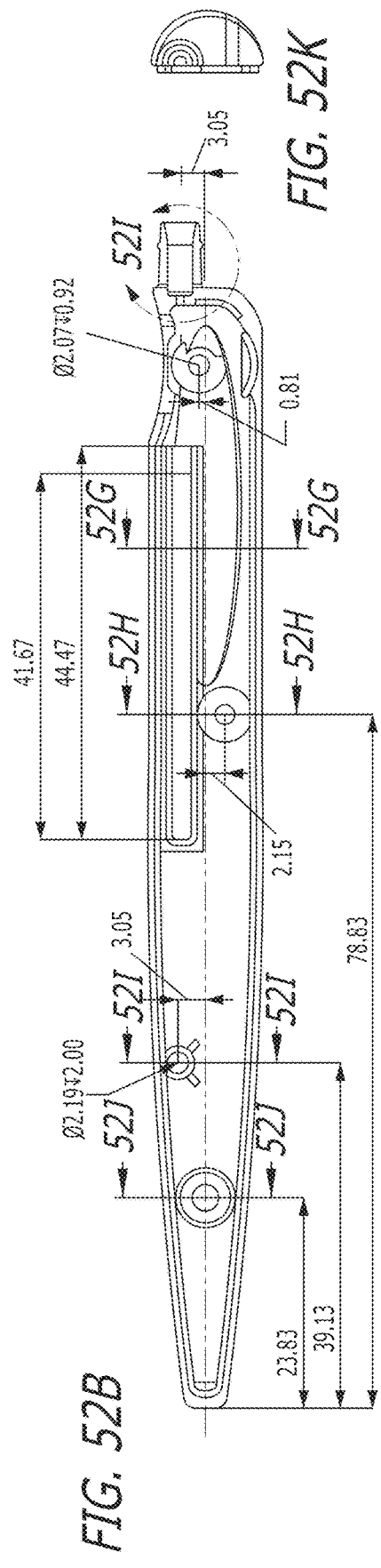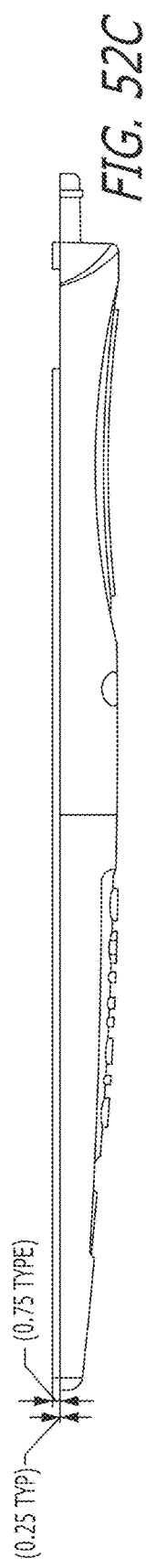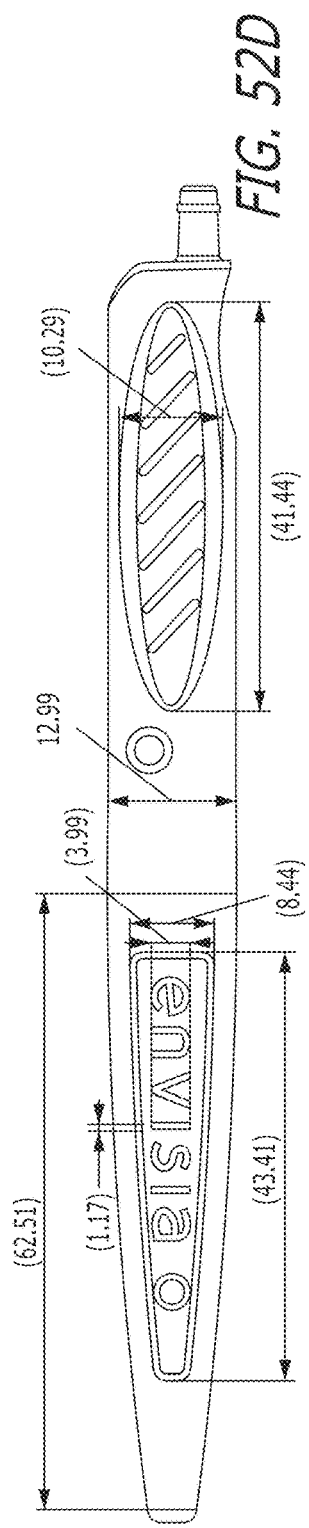

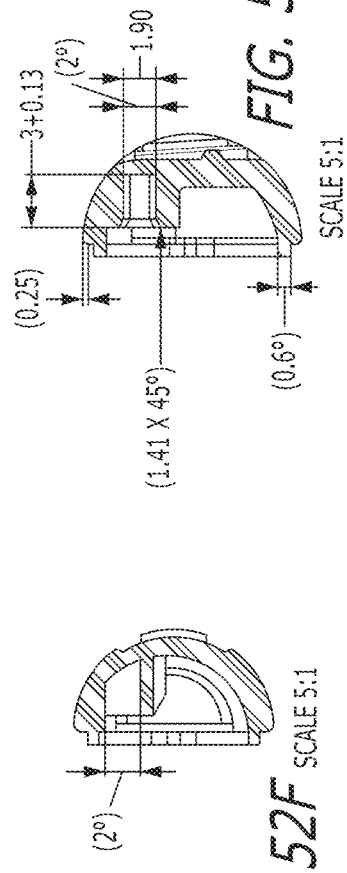
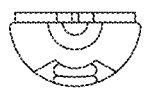
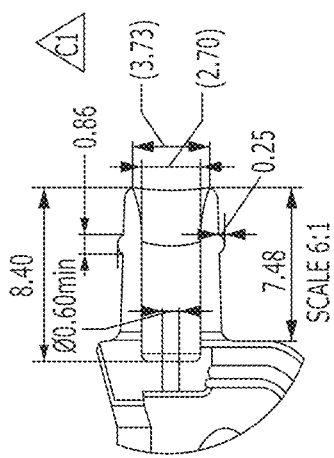

IMPLANT APPLICATORS AND METHODS OF ADMINISTERING IMPLANTS

CROSS-REFERENCE TO RELATED APPLICATIONS

This application is a continuation of International Application No. PCT/US2016/21081, filed Mar. 4, 2016 entitled "Implant Applicators and Methods of Administering Implants," hereby incorporated herein by reference in its entirety and which in turn claims priority to and benefit from each of: U.S. Provisional Application No. 62/129,737, filed Mar. 6, 2015 and titled "Implant Applicators and Methods, Systems and Devices Thereof"; U.S. Provisional Application No. 62/263,373, filed Dec. 4, 2015 and titled "Implant Applicators and Methods of Administering Implants"; and U.S. Provisional Application No. 62/263,396, filed Dec. 4, 2015 and titled "Implant Applicators and Methods of Administering Implants"; the entire contents of each of the aforementioned applications hereby expressly incorporated by reference for all purposes.

BACKGROUND

In the field of medicine, implantation methods exist for the delivery prostheses and/or medications to anatomical regions of medical patients. Drawbacks of implantation methods can include imprecise placement of the prosthesis and/or medicament within the host patient and/or complex/difficult steps for administering the implant. Drawbacks can also include complex assembly of the delivery instrument, in some cases requiring manual installation of implants into the delivery instrument.

SUMMARY

Embodiments described herein relate generally to medical implant delivery apparatuses and methods. In some embodiments, an apparatus comprises a first cap, a needle hub connected to the first cap, a pusher wire and a pusher wire connector disposed within the needle hub, a needle and a second cap. The first cap includes a proximal end, a distal end, and a longitudinal axis. The needle includes a first, beveled end configured to receive an implant, and a second end disposed within a hub pocket of the needle hub. The second cap is connected to the needle hub and disposed at a proximal end of the first cap. The pusher wire, the pusher wire connector, and the needle are substantially aligned with one another along the longitudinal axis of the first cap and/or a longitudinal axis of the first cap and the second cap. In some embodiments, the pusher wire is sized to be received in the bore of the needle. The pusher wire can be configured to engage, upon attachment to an applicator and during use, with an actuator of the applicator. In some embodiments, an applicator comprises a wheel and is configured to receive an apparatus of the present disclosure and to advance, during use, a single implant through the beveled end of the needle upon a predetermined partial rotation of the wheel.

BRIEF DESCRIPTION OF THE DRAWINGS

FIG. 5A shows a side view of a first cap, according to an embodiment.

FIG. 5B shows a first end view of the first cap of FIG. 5A.

FIG. 7 shows a pusher wire, according to an embodiment.

FIG. 18A shows the insertion sequence of a load tool into a needle hub subassembly, according to an embodiment.

FIG. 18B shows the insertion sequence of a load tool into a needle hub subassembly, according to an embodiment.

FIG. 18C shows the insertion sequence of a load tool into a needle hub subassembly, according to an embodiment.

FIG. 19A shows a process sequence for the loading of a bristle into a needle hub subassembly, according to an embodiment.

FIG. 19B shows a process sequence for the loading of a bristle into a needle hub subassembly, according to an embodiment.

FIG. 19C shows a process sequence for the loading of a bristle into a needle hub subassembly, according to an embodiment.

FIG. 19D shows a process sequence for the loading of a bristle into a needle hub subassembly, according to an embodiment.

FIG. 20A shows a bristle disposed within a bristle retainer, according to an embodiment.

FIG. 20B shows a bristle disposed within a bristle retainer, according to an embodiment.

FIG. 20C shows a bristle disposed within a bristle retainer, according to an embodiment.

FIG. 27A shows a process sequence for the insertion of a pusher subassembly after insertion of implants, and after removal of the loading fixture, according to an embodiment.

FIG. 27B shows a process sequence for the insertion of a pusher subassembly after insertion of implants, and after removal of the loading fixture, according to an embodiment.

FIG. 27C shows a process sequence for the insertion of a pusher subassembly after insertion of implants, and after removal of the loading fixture, according to an embodiment.

FIG. 27D shows a process sequence for the insertion of a pusher subassembly after insertion of implants, and after removal of the loading fixture, according to an embodiment.

FIG. 30 is a cross-sectional side view of an applicator of the injector assembly of FIG. 29, according to an embodiment.

FIG. 32A is a side view of the needle of FIG. 29, according to an embodiment.

FIG. 32B is a top view of the needle of FIG. 32A.

FIG. 32C is a perspective view of the needle of FIG. 32A.

FIG. 33B is a side view of an alternative pusher wire, according to an embodiment.

FIG. 35A is a side view of the shuttle base of FIG. 29, according to an embodiment.

FIG. 35B is a top view of the shuttle base of FIG. 35A.

FIG. 35C is an alternative side view of the shuttle base of FIG. 35A.

FIG. 35D is a bottom view of the shuttle base of FIG. 35A.

FIG. 35E is a cross-sectional view of the shuttle base of FIG. 35A taken along line A-A in FIG. 35B.

FIG. 37A is a top view of the dog bone spring of FIG. 29, according to an embodiment.

FIG. 37B is a side view of the dog bone spring of FIG. 37A.

FIG. 37C is a cross-sectional view taken along line A-A in FIG. 37A.

FIG. 37D is an enlarged view of Detail B in FIG. 37C.

FIG. 38B is a side view of the pawl of FIG. 38A.

FIG. 38C is a cross-sectional view of the pawl of FIG. 38A taken along line A-A in FIG. 38B.

FIG. 38D is a side view of the pawl of FIG. 38A in a pre-bent configuration.

FIG. 38E is a top view of the pawl of FIG. 38A in a pre-bent configuration.

FIG. 39A is a perspective view of the wheel hub of FIG. 29, according to an embodiment.

FIG. 39B is a side view of the wheel hub of FIG. 39A.

FIG. 39C is a side view of the wheel hub of FIG. 39A from the opposite side as FIG. 39B.

FIG. 39D is a proximal end view of the wheel hub of FIG. 39A. FIG. 39E is a distal end view of the wheel hub of FIG. 39A.

FIG. 40A is a perspective view of the first wheel rim of FIG. 29, according to an embodiment.

FIG. 40B is a side view of the first wheel rim of FIG. 40A.

FIG. 40C is a cross-sectional view of the first wheel rim of FIG. 40A taken along line A-A in FIG. 40B.

FIG. 40D is an enlarged view of Detail C in FIG. 40C.

FIG. 40E is an enlarged view of Detail D in FIG. 40B.

FIG. 40F is an enlarged view of Detail E in FIG. 40B.

FIG. 40G is a front view of the first wheel rim of FIG. 40A.

FIG. 40H is a side view of the first wheel rim of FIG. 40A from the opposite side of FIG. 40B.

FIG. 40I is a cross-sectional view taken along line B-B in FIG. 40H.

FIG. 40J is an enlarged view of Detail F in FIG. 40H.

Figure 41:
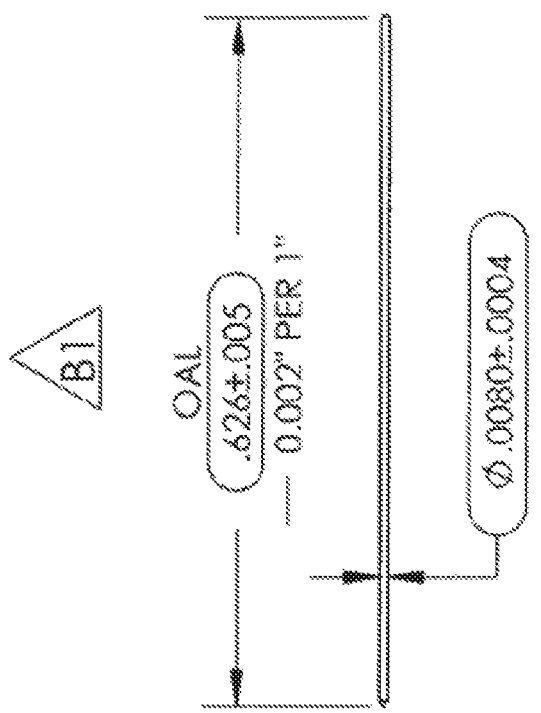

FIG. 41 is a side view of a secondary pusher wire, according to an embodiment.

Figure 29:
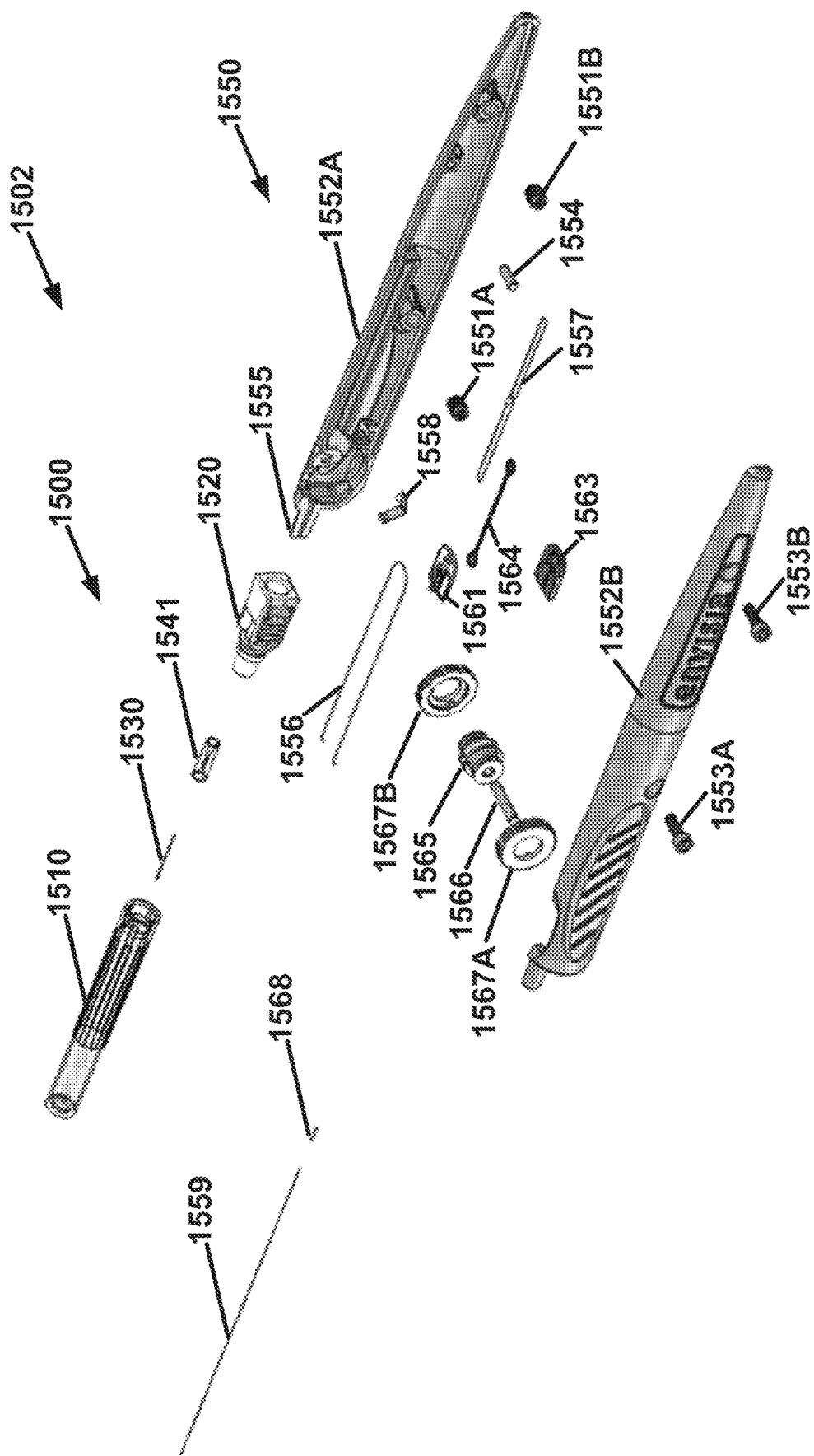
FIG. 29 is an exploded perspective view of an injector assembly, according to an embodiment.

FIG. 42A is a top view of the first housing portion of FIG. 29, according to an embodiment.

FIG. 42B is a side view of the first housing portion of FIG. 42A.

FIG. 42C is a bottom view of the first housing portion of FIG. 42A.

FIG. 42D is a side view of the first housing portion of FIG. 42A from the opposite side of FIG. 42B.

Figure 42E:
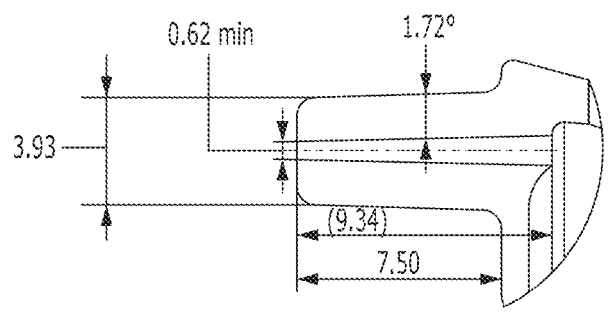

FIG. 42E is an enlarged view of Detail A in FIG. 42B.

Figure 42F:
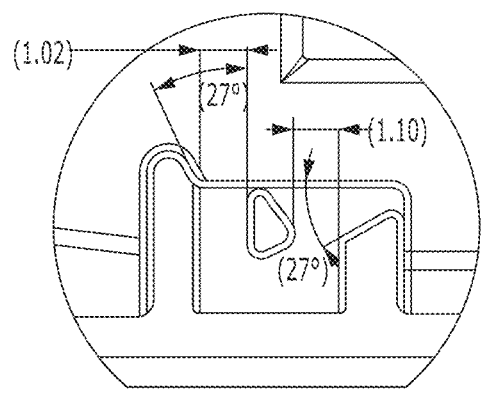

FIG. 42F is an enlarged view of Detail B in FIG. 42B.

Figure 42G:
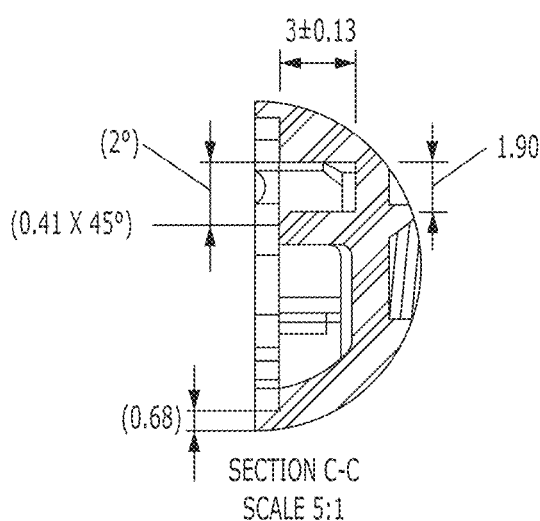

FIG. 42G is a cross-sectional view of the first housing portion of FIG. 42A taken along line C-C in FIG. 42B.

Figure 42H:
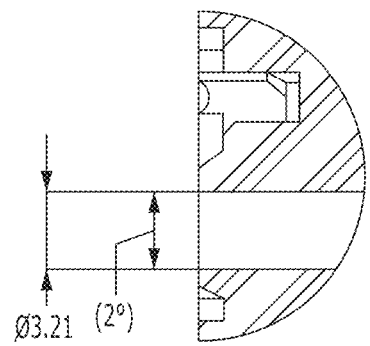

FIG. 42H is a cross-sectional view of the first housing portion of FIG. 42A taken along line D-D in FIG. 42B.

Figure 42I:
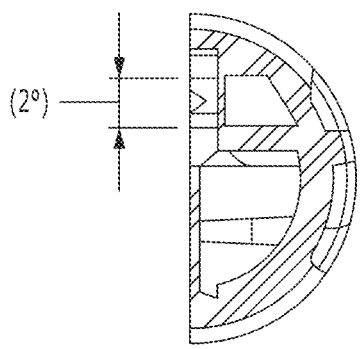

FIG. 42I is a cross-sectional view of the first housing portion of FIG. 42A taken along line O-O in FIG. 42B.

Figure 42J:
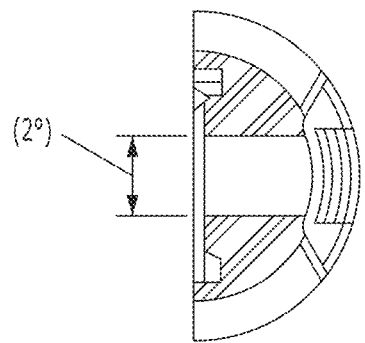

FIG. 42J is a cross-sectional view of the first housing portion of FIG. 42A taken along line P-P in FIG. 42B.

FIG. 42K is a distal end view of the first housing portion of FIG. 42A. FIG. 42L is a proximal end view of the first housing portion of FIG. 42A.

FIG. 43A is a top view of the second housing portion of FIG. 29, according to an embodiment.

FIG. 43B is a side view of the second housing portion of FIG. 43A.

FIG. 43C is a bottom view of the second housing portion FIG. 43A.

FIG. 43D is a side view of the second housing portion FIG. 43A from the opposite side of FIG. 43B.

FIG. 43E is a cross-sectional view of the second housing portion FIG. 43A taken along line A-A in FIG. 43B.

FIG. 43F is a cross-sectional view of the second housing portion FIG. 43A taken along line B-B in FIG. 43B.

FIG. 43G is a cross-sectional view of the second housing portion FIG. 43A taken along line C-C in FIG. 43B.

FIG. 43H is a cross-sectional view of the second housing portion FIG. 43A taken along line D-D in FIG. 43B.

FIG. 43I is an enlarged view of Detail E in FIG. 43B.

FIG. 43J is a distal end view of the second housing portion FIG. 43A.

FIG. 43K is a proximal end view of the second housing portion FIG. 43A.

Figure 44:
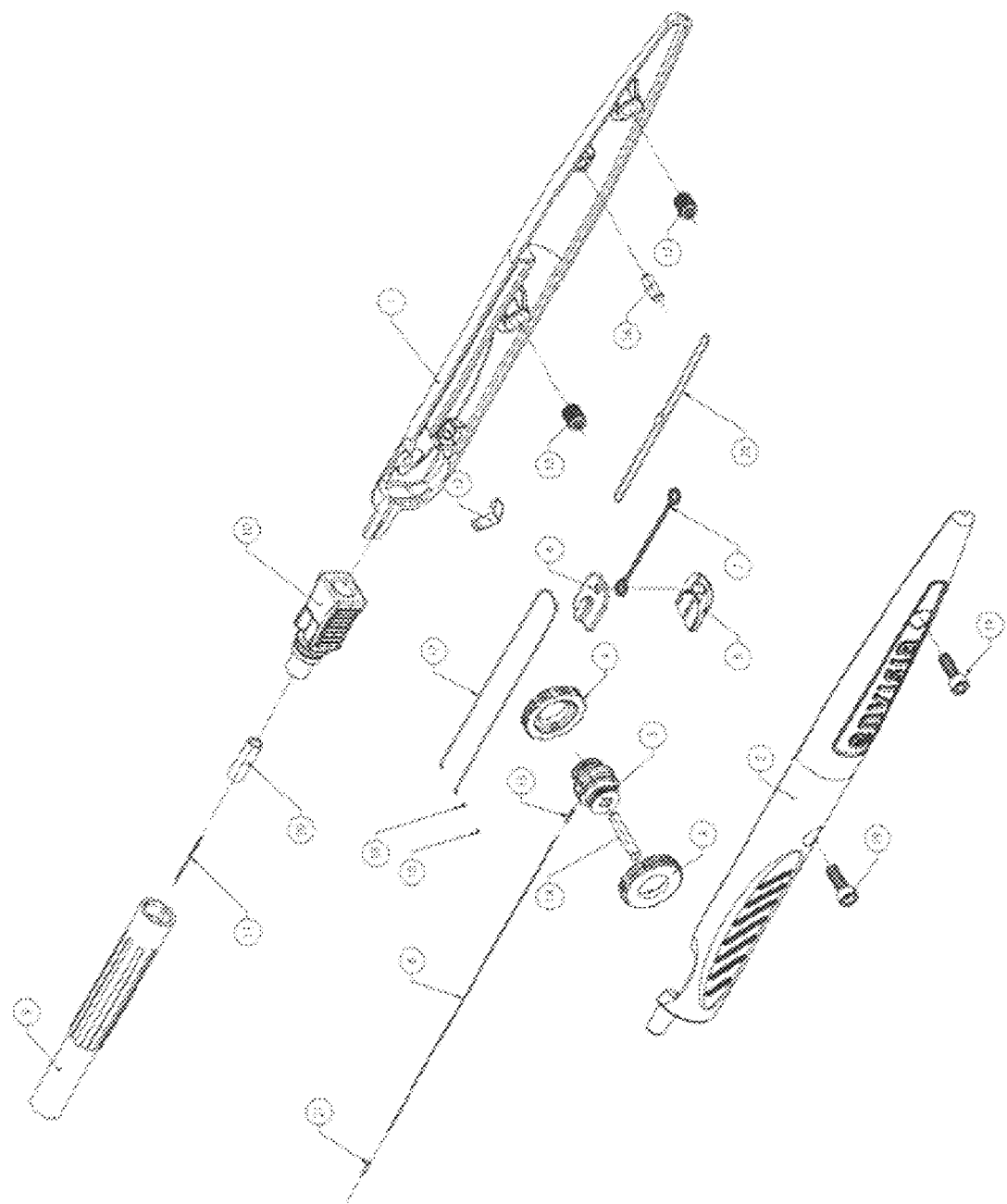

FIG. 44 is an exploded perspective view of an injector assembly, according to an embodiment.

Figure 45A:
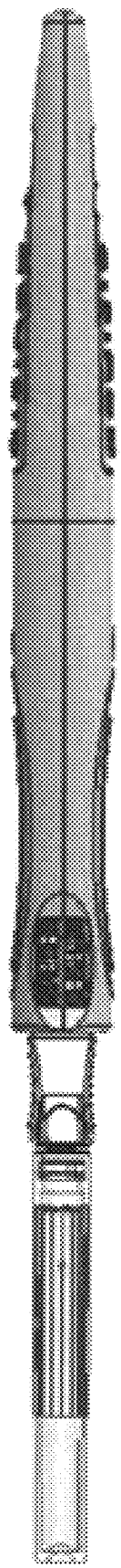

FIG. 45A is a top view of the injector assembly of FIG. 44.

Figure 45B:
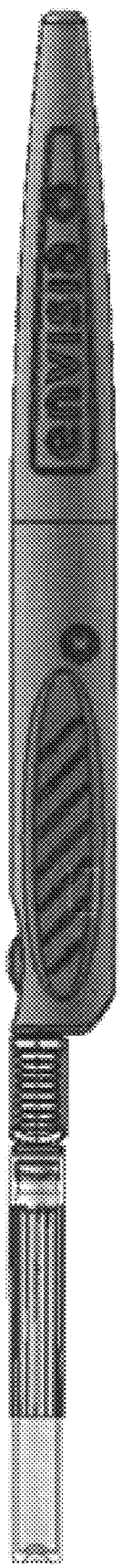

FIG. 45B is a side view of the injector assembly of FIG. 44.

Figure 46:
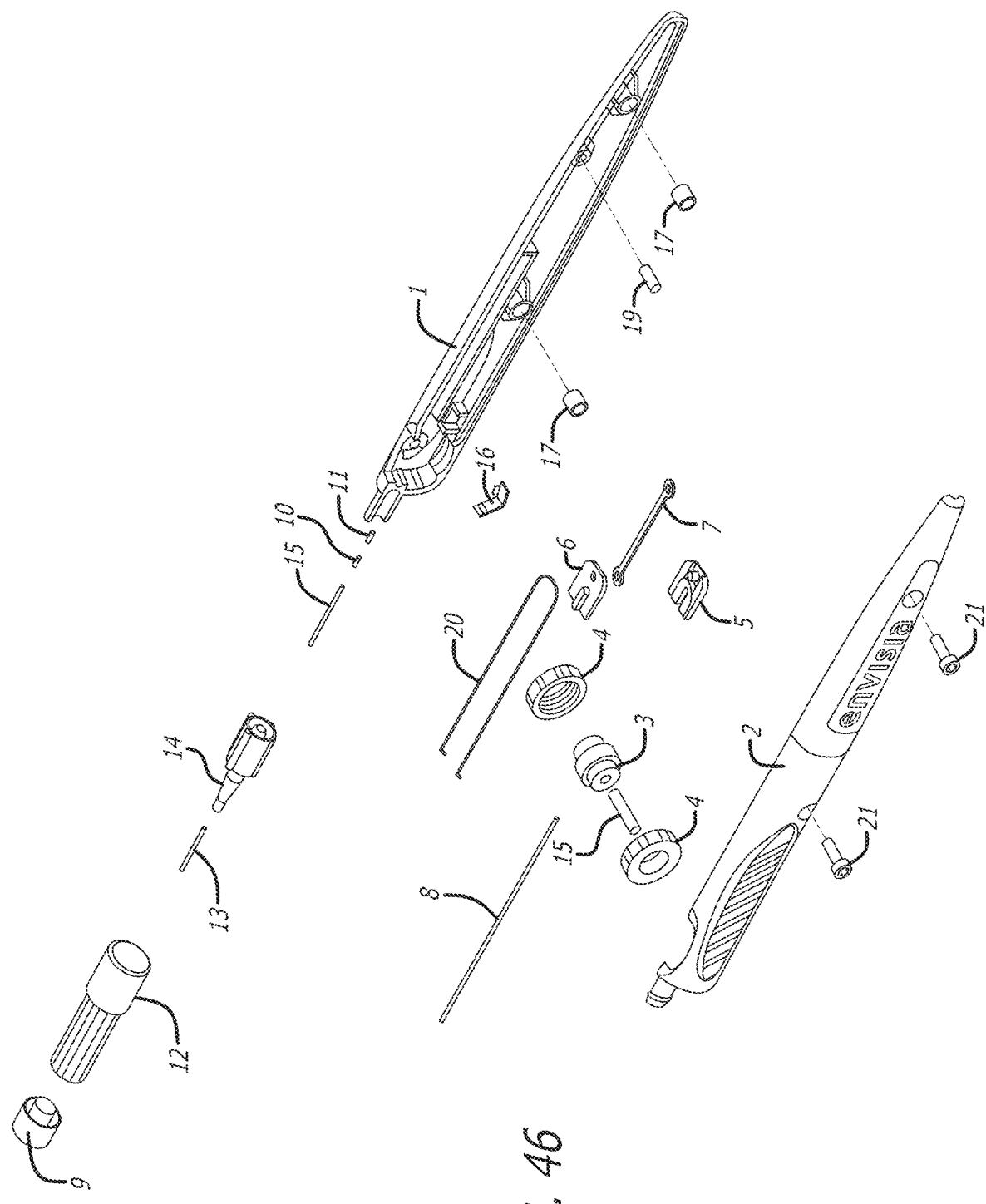

FIG. 46 is an exploded perspective view of an injector assembly, according to an embodiment.

Figure 47A:
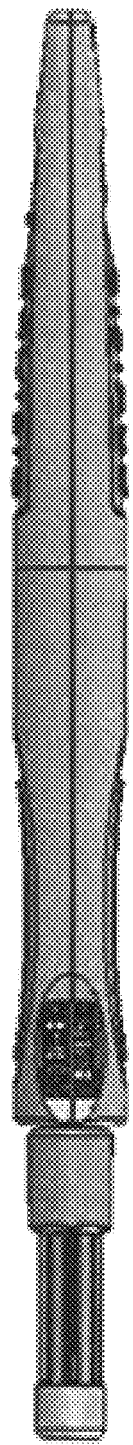

FIG. 47A is a top view of the injector assembly of FIG. 46.

Figure 47B:
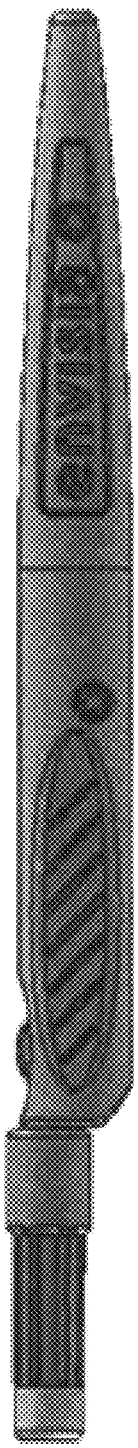

FIG. 47B is a side view of the injector assembly of FIG. 46.

Figure 48A:
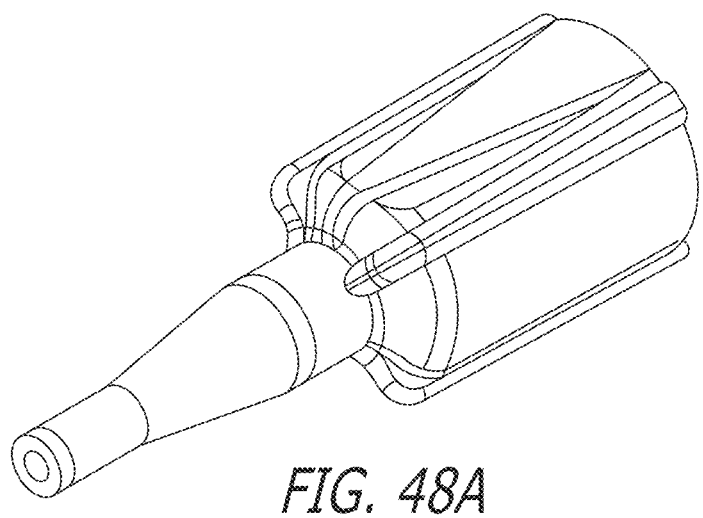

FIG. 48A is a perspective view of the needle hub of FIG. 46, according to an embodiment.

FIG. 48B is a top view of the needle hub of FIG. 48A.

FIG. 48C is a side view of the needle hub of FIG. 48A.

FIG. 48D is a distal end view of the needle hub of FIG. 48A.

FIG. 48E is a proximal end view of the needle hub of FIG. 48A.

FIG. 48F is a cross-sectional view taken along line A-A in of FIG. 48A.

Figure 48G:
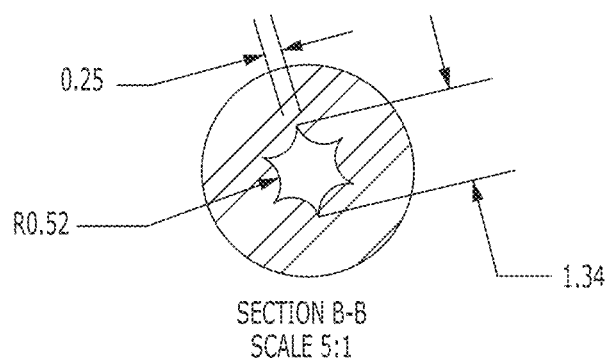

FIG. 48G is a cross-sectional view of the needle hub of FIG. 48A taken along line B-B in FIG. 48F.

FIG. 49A is a side view of the open-ended cap of FIG. 46, according to an embodiment.

FIG. 49B is a distal end view of the open-ended cap of FIG. 49A.

FIG. 48C is a proximal end view of the open-ended cap of FIG. 49A.

FIG. 48D is a cross-sectional view of the open-ended cap of FIG. 49A taken along line A-A in FIG. 49A.

Figure 50C:
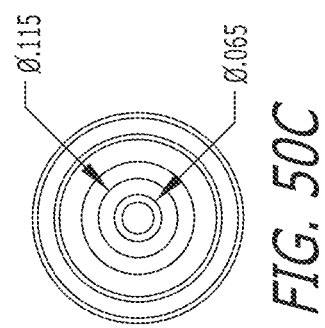
Figure 50A:
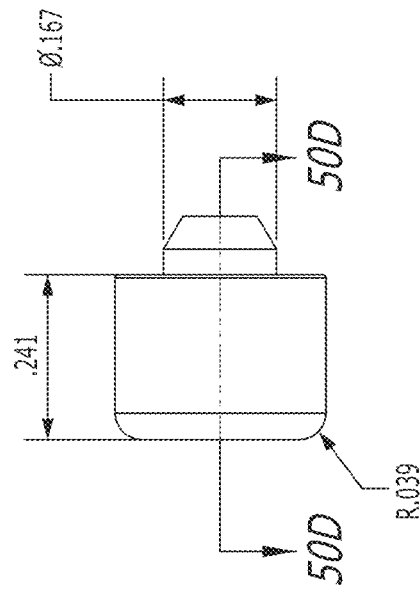

FIG. 50A is a side view of the open-ended cap plug of FIG. 46, according to an embodiment.

Figure 50D:
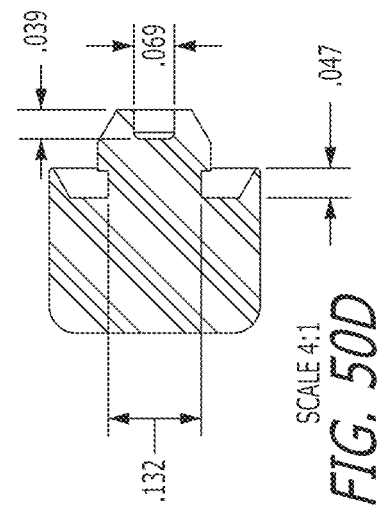
Figure 50B:
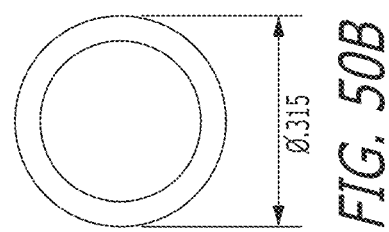

FIG. 50B is a distal end view of the open-ended cap plug of FIG. 50A.

FIG. 50C is a proximal end view of the open-ended cap plug of FIG. 50A.

FIG. 50D is a cross-sectional view of the open-ended cap plug of FIG. 50A taken along line A-A in FIG. 50A.

FIG. 51A is a top view of the first housing portion of FIG. 46, according to an embodiment.

FIG. 51B is a side view of the first housing portion of FIG. 51A.

FIG. 51C is a bottom view of the first housing portion of FIG. 51A.

FIG. 51D is a side view of the first housing portion of FIG. 51A from the opposite side of FIG. 51B.

Figure 51E:
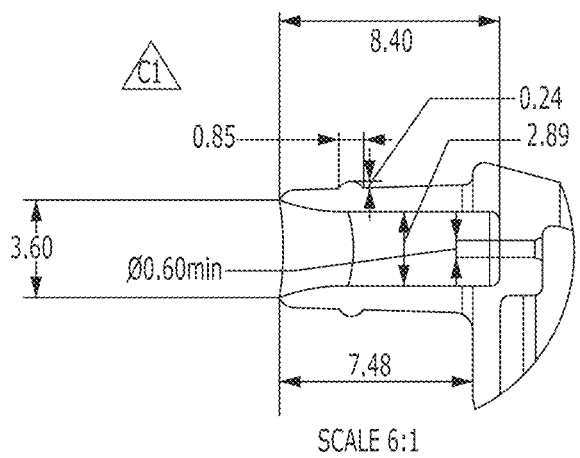

FIG. 51E is an enlarged view of Detail A in FIG. 51B.

Figure 51F:
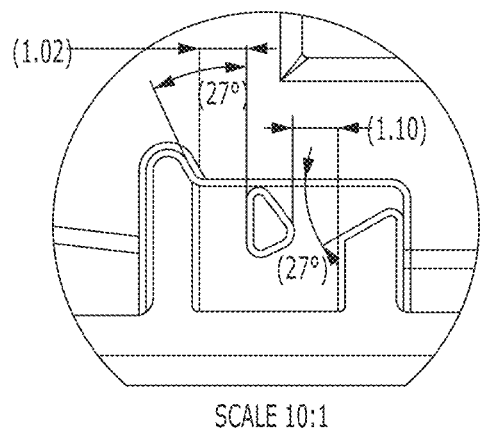

FIG. 51F is an enlarged view of Detail B in FIG. 51B.

Figure 51G:
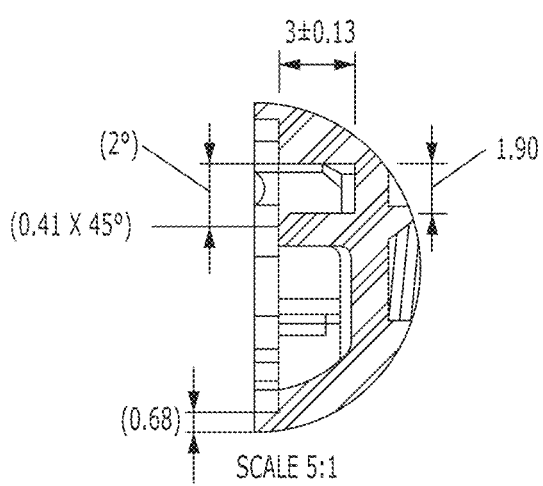

FIG. 51G is a cross-sectional view of the first housing portion of FIG. 51A taken along line C-C in FIG. 51B.

Figure 51H:
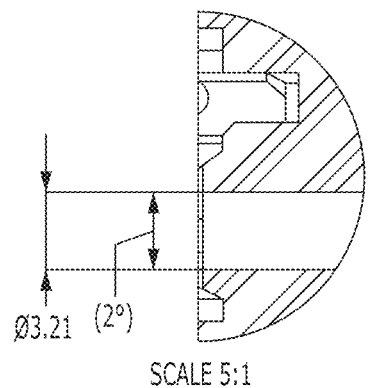

FIG. 51H is a cross-sectional view of the first housing portion of FIG. 51A taken along line D-D in FIG. 51B.

Figure 51I:
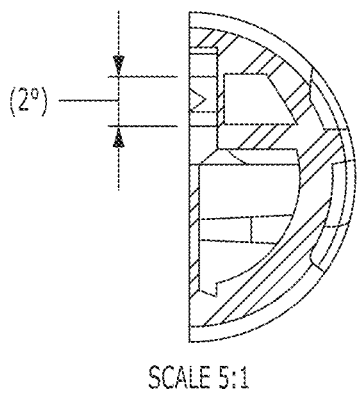

FIG. 51I is a cross-sectional view of the first housing portion of FIG. 51A taken along line O-O in FIG. 51B.

Figure 51J:
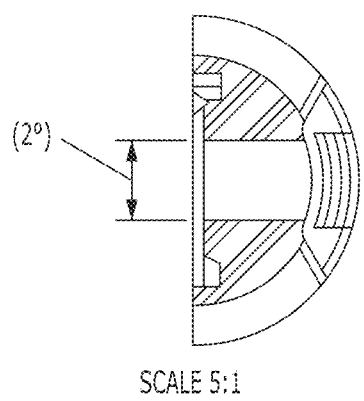

FIG. 51J is a cross-sectional view of the first housing portion of FIG. 51A taken along line P-P in FIG. 51B.

FIG. 51K is a distal end view of the first housing portion of FIG. 51A.

FIG. 51L is a proximal end view of the first housing portion of FIG. 51A.

FIG. 52A is a top view of the second housing portion of FIG. 46, according to an embodiment.

FIG. 52B is a side view of the second housing portion of FIG. 52A.

FIG. 52C is a bottom view of the second housing portion of FIG. 52A.

FIG. 52D is a side view of the second housing portion of FIG. 52A from the opposite side of FIG. 52B.

FIG. 52E is a cross-sectional view of the second housing portion of FIG. 52A taken along line A-A in FIG. 52B.

FIG. 52F is a cross-sectional view of the second housing portion of FIG. 52A taken along line B-B in FIG. 52B.

FIG. 52G is a cross-sectional view of the second housing portion of FIG. 52A taken along line C-C in FIG. 52B.

FIG. 52H is a cross-sectional view of the second housing portion of FIG. 52A taken along line D-D in FIG. 52B.

FIG. 52I is an enlarged view of Detail E in FIG. 52B.

FIG. 52J is a distal end view of the second housing portion of FIG. 52A.

FIG. 52K is a proximal end view of the second housing portion of FIG. 52A.

DETAILED DESCRIPTION

Implantation methods exist for the delivery of prostheses and/or medications to anatomical regions of medical patients. Drawbacks of implantation methods can include imprecise placement of the prosthesis and/or medicament within the host patient, cumbersome assembly of the delivery instrument, and/or complex/difficult steps for administering the implant. In the present disclosure, medical implantation devices and methods are disclosed that have improved functionality over existing implantation techniques. For example, implant delivery apparatuses of the present disclosure can include a needle that can be manually loaded by a physician (e.g., a surgeon) via a beveled end of the needle prior to surgery. Additionally, in some embodiments, implant delivery apparatuses of the present disclosure can also include a needle hub assembly that can be preloaded via a proximal end of the hub. The preloaded needle hub assembly can be preloaded, for, example, immediately prior to use in a procedure or prior to distribution to a user (e.g., a surgeon) for use in a procedure. In some embodiments, the preloaded needle hub assembly can be attached to a device handle assembly and distributed to a user (e.g., a surgeon) as a unit. Implant delivery apparatuses described herein can also include a "push pin" or "pusher wire" that, during use, engages with one or more implants disposed within the bore of the needle. The pusher wire can also be configured to interface with an applicator so as to exhibit a "zero prime" feature, in that with each actuation of the applicator (e.g., with each predetermined angular rotation of a knob having multiple spaced detents or projections), a single implant (e.g., an ocular implant) is linearly advanced, either through direct or indirect contact with the pusher wire, out of the implant delivery apparatus.

Embodiments described herein relate generally to medical implant delivery apparatuses and methods. In some embodiments, an apparatus comprises a first cap, a needle hub connected to the first cap, a pusher wire and a pusher wire connector disposed within the needle hub, a needle, and a second cap. The first cap includes a proximal end, a distal end, and a longitudinal axis. The needle includes a first, beveled end configured to receive an implant, and a second end disposed within a hub pocket of the needle hub. The second cap is connected to the needle hub and disposed at a proximal end of the first cap. The pusher wire, the pusher wire connector, and the needle are substantially aligned with one another along the longitudinal axis of the first cap. In some embodiments, the pusher wire is sized to be received in the bore of the needle. The pusher wire can be configured to engage, upon attachment to an applicator and during use, with an actuator of the applicator. In some embodiments, an applicator comprises a wheel and is configured to receive an apparatus of the present disclosure and to advance, during use, a single implant through the beveled end of the needle upon a predetermined partial rotation of the wheel.

Figure 1:
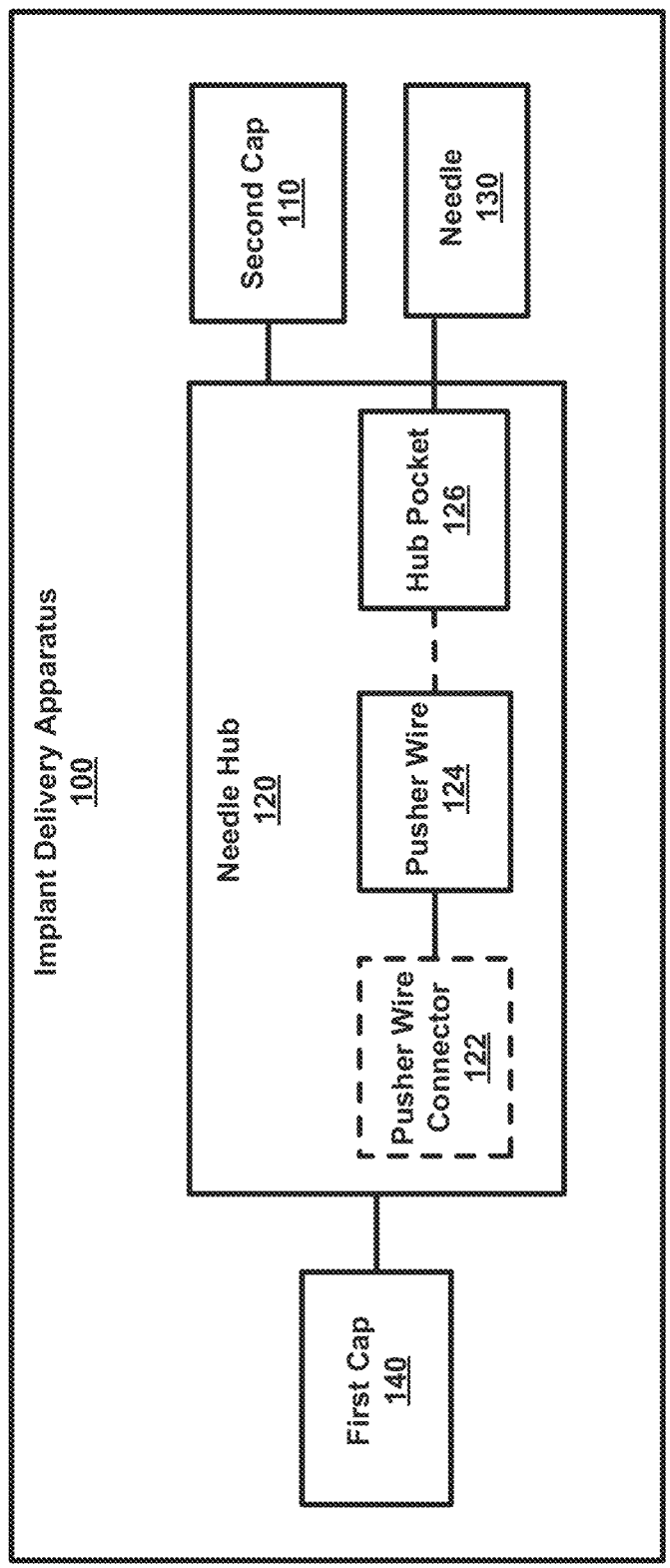
FIG. 1 is a schematic block diagram of an implant delivery apparatus, according to an embodiment.

Turning now to FIG. 1, an implant delivery apparatus 100 includes a first cap 140, a needle hub 120, a second cap 110 and a needle 130. The needle 130 can include a beveled distal end and a non-beveled proximal end. A distal end of the needle hub 120, which is closer to the beveled end of the needle 130 compared to a proximal end of the needle hub 120, is connected to the second cap 110, for example via a push-fit configuration, as shown and described below. The proximal end of the needle hub 120, which is opposite the distal end of the needle hub 120, can be configured for attachment to an applicator, as shown and described below. The needle hub 120 includes a pusher wire 124 that can optionally include a pusher wire connector 122 at a proximal end of the pusher wire 124. The pusher wire 124 can be adjacent to and axially aligned with, or at least partially received within, a hub pocket 126 of the needle hub 120. In some embodiments, the needle hub 120 is partially or substantially fully received within the second cap 110 via a first proximal end of the second cap 110. In some embodiments, a distal end of the second cap 110 can define an opening through which a portion of the needle 130 can project. In some embodiments an opening is defined for implant loading. The proximal end of the needle hub 120 is connected to a distal end of the first cap 140. For example, the needle hub 120 may be received at least partially within the first cap 140. A proximal end of the first cap 140 can be closed or open. The needle 130 is partially received in the hub pocket 126 of the needle hub 120. In some embodiments, an adhesive (e.g., Loctite® or any other suitable adhesive) is used to secure the needle hub 120 to the needle 130, and/or to secure the pusher wire connector 122 to the pusher wire 124.

Figure 2:
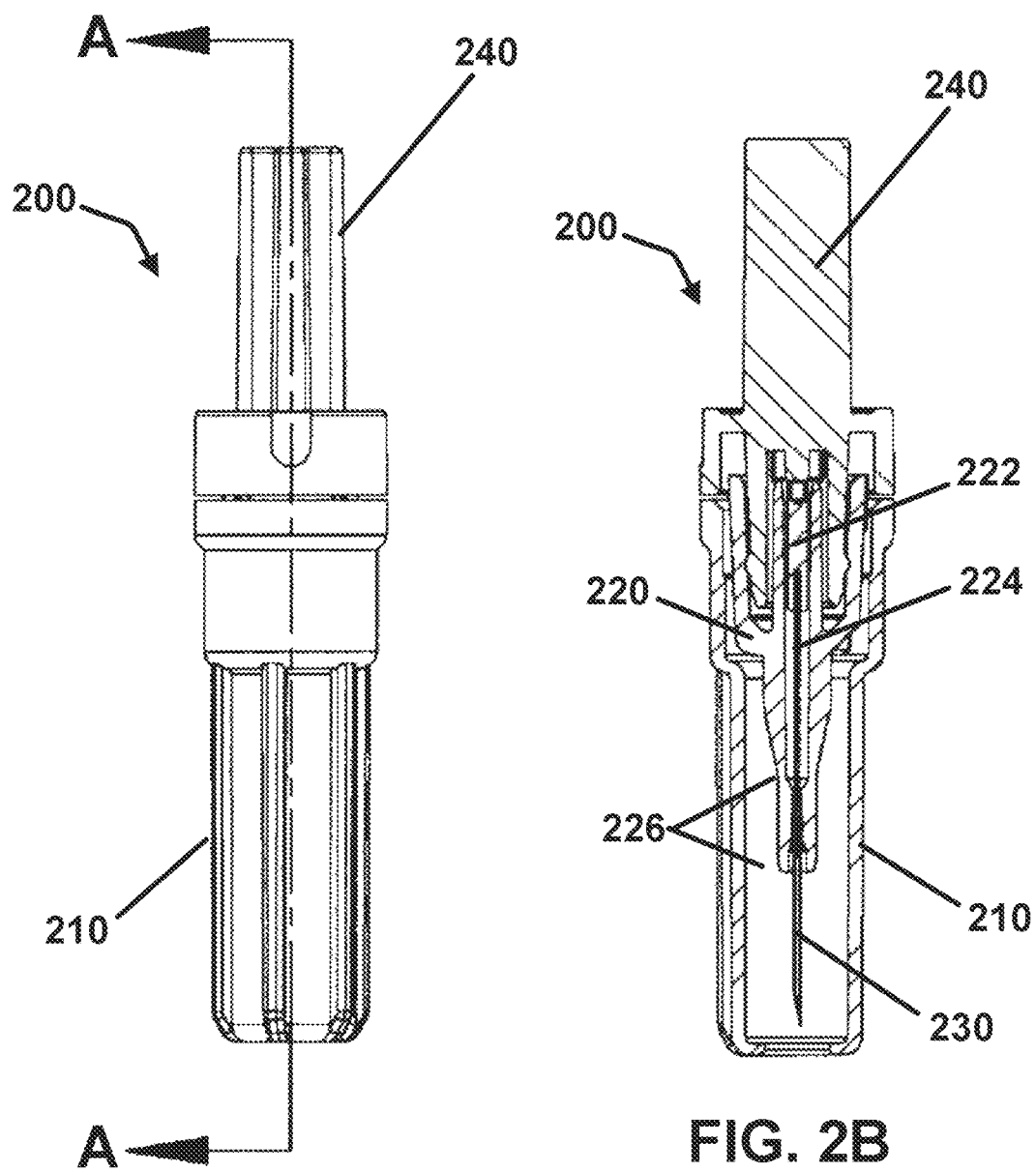
FIG. 2A shows a side view of an assembled implant delivery apparatus, according to an embodiment.
FIG. 2B shows a further side view of the implant delivery apparatus of FIG. 2A, in cross-section (taken along section line A-A of FIG. 2A).

FIG. 2A shows an external side view of an assembled implant delivery apparatus, according to an embodiment. As shown in FIG. 2A, an implant delivery apparatus 200 includes a first cap 240 joined with a second cap 210. The first cap 240 is closer to a non-beveled proximal end of a needle 230 (shown in FIG. 2B) than to a beveled distal end of the needle 230. The second cap 210 is closer to a beveled distal end of the needle 230 compared to the first cap 240. FIG. 2B shows a further side view of the implant delivery apparatus of FIG. 2A, in cross-section (taken along section line A-A of FIG. 2A). Visible in the cross-section of FIG. 2B are the first cap 240, the second cap 210, and all intervening components. As shown, a pusher wire 224 is partially received within a distal end of a pusher wire connector 222, and a needle 230 is partially received within a hub pocket 226 of a needle hub 220. The needle hub 220 is substantially fully disposed within the second cap 210, and the first cap 240 is cooperatively engaged with the needle hub 220 (i.e., each of the first cap 240 and the needle hub 220 has a male and a female connection that mate with corresponding female and male connections, respectively). Each of the needle 230, the pusher wire 224, and the pusher wire connector 222 are disposed along a common axis corresponding to a longitudinal axis of the implant delivery apparatus 200. The implant delivery apparatus 200 can be the same or similar in structure and function to any of the delivery apparatuses described herein, such as, for example, the implant delivery apparatus 100 described above.

Figure 3:
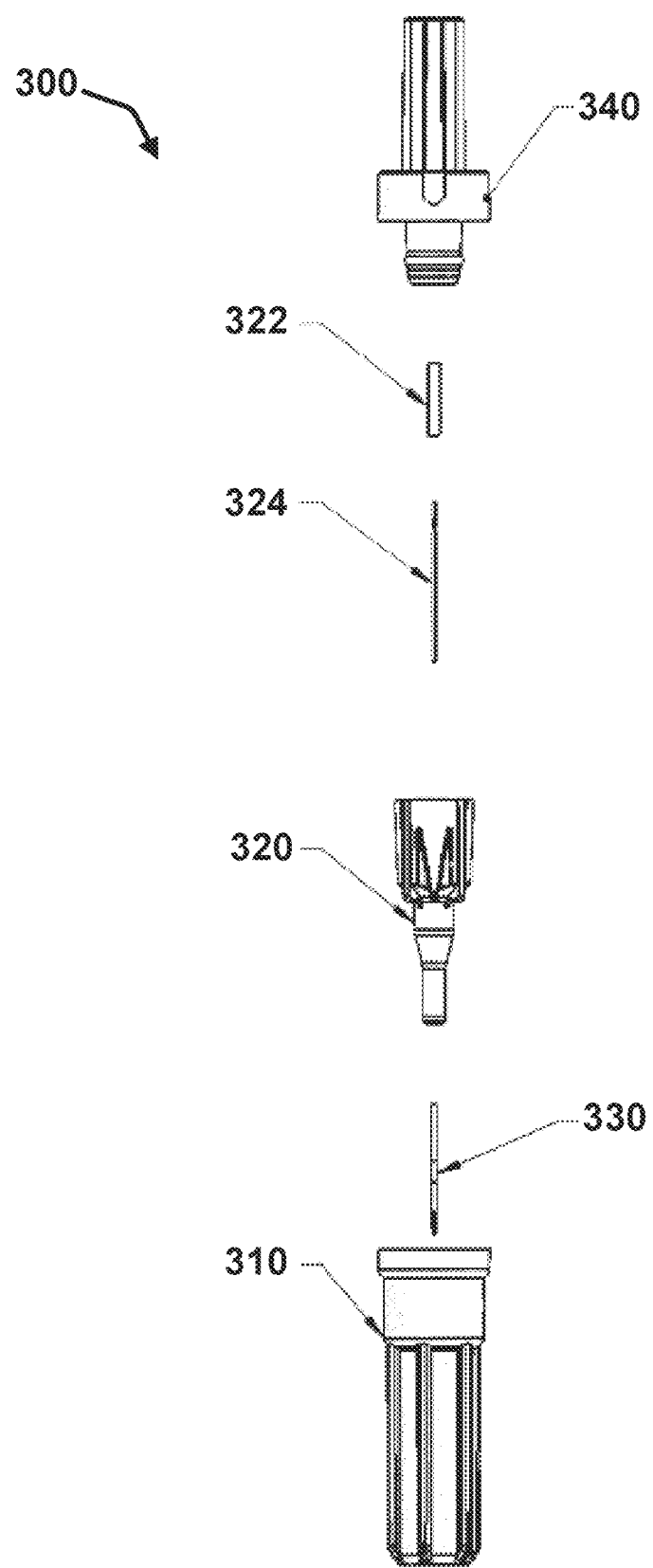
FIG. 3 shows an exploded view of an implant delivery apparatus, showing internal components thereof, according to an embodiment.

FIG. 3 shows an exploded view of an implant delivery apparatus, showing internal components thereof, according to an embodiment. As shown in FIG. 3, components of an implant delivery apparatus 300 include a first cap 340, a pusher wire connector 322, a pusher wire 324, a needle hub 320, a needle 330, and a second cap 310. The implant delivery apparatus 300 can be the same or similar in structure and function to any of the delivery apparatuses described herein, such as, for example, the implant delivery apparatuses 100 and 200 described above.

Figure 4A:
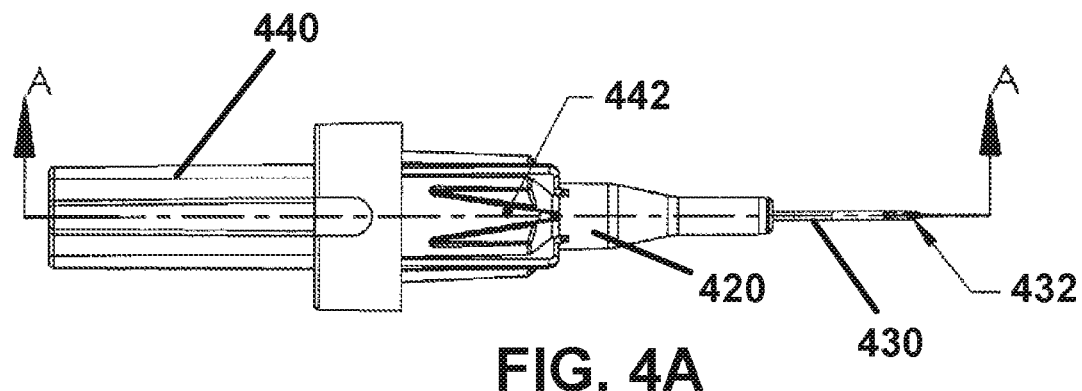
FIG. 4A shows a side view of a partially assembled implant delivery apparatus, according to an embodiment.
Figure 4B:
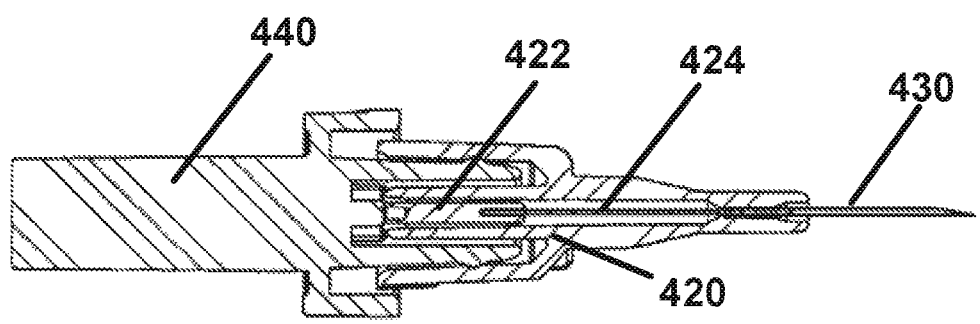
FIG. 4B shows a further side view of the partially assembled implant delivery apparatus of FIG. 4A, in cross-section (taken along section line A-A of FIG. 4A).

FIG. 4A shows a side view of a partially assembled implant delivery apparatus, according to an embodiment. As shown in FIG. 4A, a first cap 440 and a needle hub 420 are mechanically connected, and a needle 430 is partially disposed within the needle hub 420. The needle hub 420 includes a v-shaped bevel indicator 442. The v-shaped bevel indicator 442 is visible and corresponds with a needle bevel 432 of the needle 430. FIG. 4B shows a further side view of the partially assembled implant delivery apparatus of FIG. 4A, in cross-section (taken along section line A-A of FIG. 4A). As shown in FIG. 4B, the first cap 440 and the needle hub 420 are mechanically connected, and the needle 430 is partially disposed within the hub pocket of the needle hub 420. A pusher wire 424 is partially received in a corresponding pusher wire connector 422. The first cap 440, the needle hub 420, the needle 430, the pusher wire 424, and the pusher wire connector 422 can be the same or similar in structure and function to any of the first cap, the needle hub, the needle, the pusher wire, and the pusher wire connector described in any of the delivery apparatuses described herein, such as, for example, the implant delivery apparatuses 100, 200, and 300 described above.

Figure 5E:
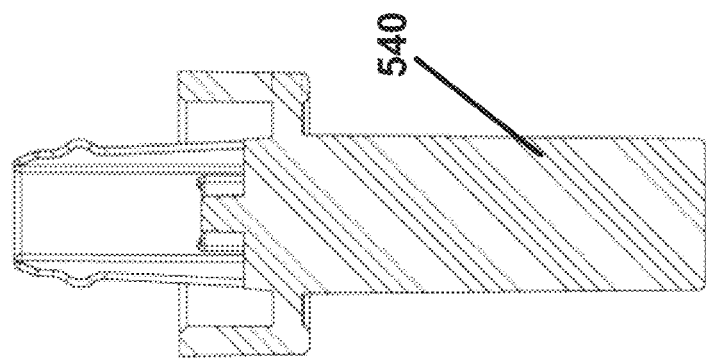
FIG. 5E shows a further side view of the first cap of FIG. 5A, in cross-section (taken along section line B-B of FIG. 5C).
Figure 5D:
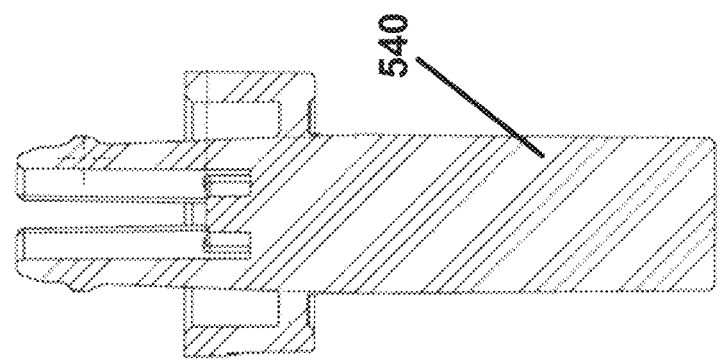
FIG. 5D shows a further side view of the first cap of FIG. 5A, in cross-section (taken along section line A-A of FIG. 5C).
Figure 5C:
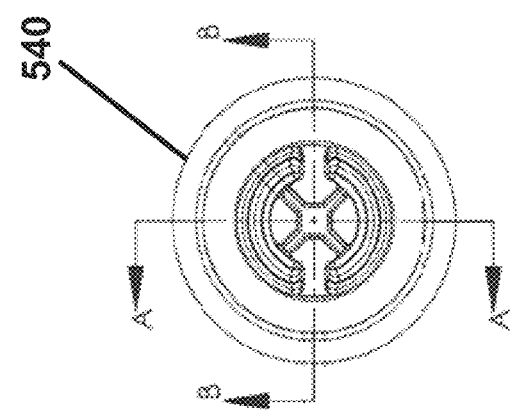
FIG. 5C shows a second end view of the first cap of FIG. 5A.

FIG. 5A shows a side view of a first cap 540, according to an embodiment. The first cap 540 has a proximal end 544 and distal end 546. In use, the distal end 546 of the first cap 540, which has both male and female connections, interfaces with a needle hub. FIG. 5B shows a first (proximal) end view of the first cap 540 of FIG. 5A, and FIG. 5C shows a second (distal) end view of the first cap 540 of FIG. 5A. FIG. 5D shows a further side view of the first cap 540 of FIG. 5A, in cross-section (taken along section line A-A of FIG. 5C). FIG. 5E shows a further side view of the first cap 540 of FIG. 5A, in cross-section (taken along section line B-B of FIG. 5C). The first cap 540 can be the same or similar in structure and function to any of the first caps described herein, such as, for example, the first caps 140, 240, 340, and 440 described above.

Figure 6A:
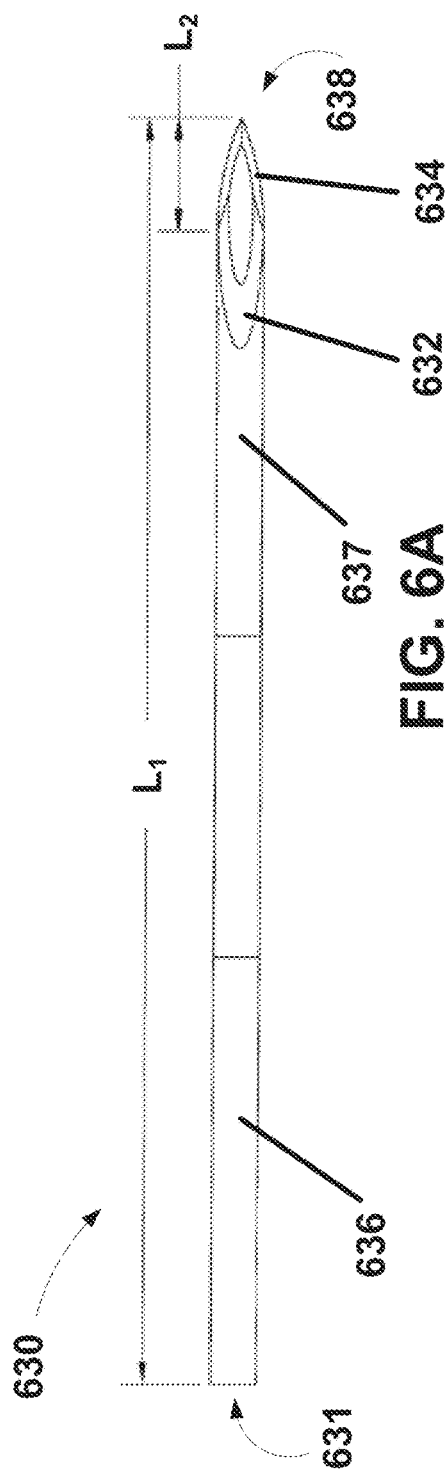
FIG. 6A shows a top view of a needle, according to an embodiment.
Figure 6B:
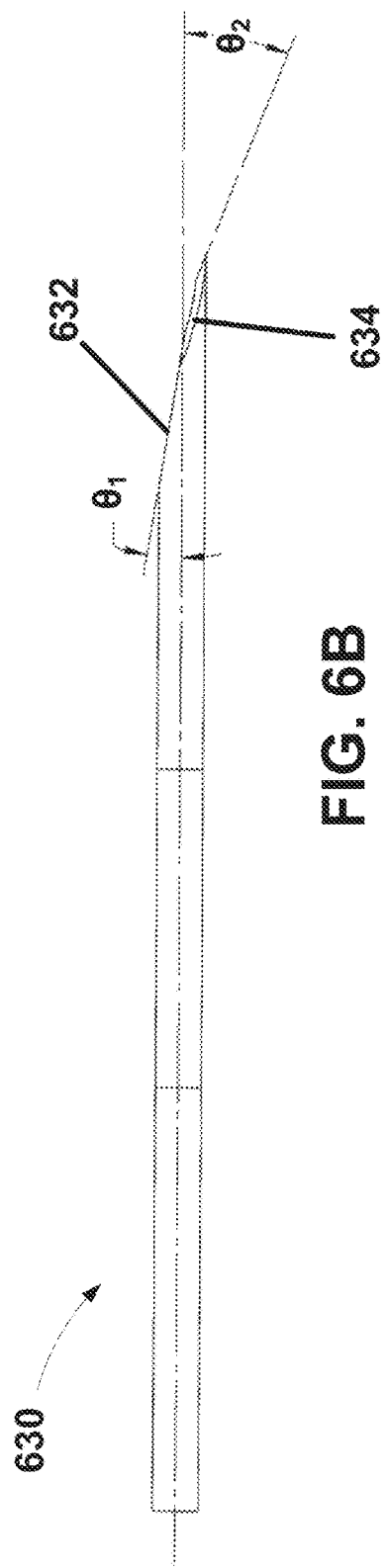
FIG. 6B shows a side view of the needle of FIG. 6A.
Figure 6C:
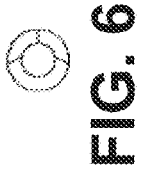
FIG. 6C shows an end view, from the beveled end, of the needle of FIG. 6A.

FIG. 6A shows a top view of a needle, according to an embodiment. In some embodiments, a needle 630 includes a non-beveled, proximal end 631 and a beveled, distal end 638. In some embodiments, the needle 630 includes a roughened portion 636 extending from the non-beveled end 631. The roughened portion 636 is etched or otherwise roughened, for example, to improve adhesion (e.g., to the hub pocket of a needle hub). In some embodiments, the needle 630 includes a coated portion 637 extending from the beveled end 638. The coated portion 637 is coated with a material such as silicone (i.e., "siliconized") or other biocompatible non-stick substance, e.g., for ease of insertion into the eye of a patient. The needle 630 can be a hypodermic medical grade needle, and can comprise stainless steel (e.g., 304 SS). Machined surfaces of the needle 630 are burr-free or substantially burr-free. The overall length $L_1$ of the needle can be, for example, less than one inch. In some embodiments, for example, the overall length $L_1$ can be about 0.466"+/−0.010". Additionally, the needle size can range, for example, from 16 to 35 gauge. The overall length $L_1$ and gauge of the needle 630 can be selected such that a desired number and/or size of implants can be loaded into the needle 630 for implantation. The lancet length $L_2$ can be substantially less than the overall length $L_1$ of the needle (e.g., about 0.042"). In some embodiments, the beveled end 638 includes a needle bevel 632 and a lancet portion 634. FIG. 6B shows a side view of the needle of FIG. 6A, illustrating the primary grind angle $\theta_1$ of the needle bevel 632 and the piercing angle $\theta_2$ of the lancet portion 634. In some embodiments, the primary grind angle $\theta_1$ is about 9 degrees, +/−2 degrees. In some embodiments, the piercing angle $\theta_2$ is about 22 degrees, +/−2 degrees. FIG. 6C shows an end view, from the beveled end 638, of the needle of FIG. 6A. The needle 630 can be the same or similar in structure and function to any of the needles described herein, such as, for example, the needles 130, 230, 330, and 430 described above.

In some embodiments, the beveled, distal end 638 of the needle 630 can be configured to receive one or more implants such that the one or more implants can be loaded into the needle 630 via the beveled, distal end 638. In other embodiments, the non-beveled, proximal end 638 of the needle 630 can be configured to receive one or more implants such that the one or more implants can be loaded into the needle 630 via the non-beveled, proximal end 638.

In some embodiments, an apparatus comprises a first cap, a needle hub connected to the first cap, a pusher wire and a pusher wire connector disposed within the needle hub, a needle, and a second cap. The first cap includes a proximal end closer to beveled end of the needle, a distal end closer to the non-beveled end of the needle, and a longitudinal axis. The needle includes a first, beveled end configured to receive an implant if implants are loaded from the beveled end of the needle, and a second end disposed within a hub pocket of the needle hub configured to receive an implant if implants are loaded from the non-beveled end of the needle. The second cap is connected to the needle hub and covering the beveled end of the needle, and disposed at a proximal end of the first cap. The pusher wire, the pusher wire connector, and the needle are substantially aligned with one another along the longitudinal axis of the first cap. In some embodiments, the pusher wire is sized to be received in the bore of the needle. The pusher wire can be configured to engage, upon attachment to an applicator and during use, with an actuator of the applicator. In some embodiments, an applicator comprises a wheel and is configured to receive an apparatus of the present disclosure and to advance, during use, a single implant through the beveled end of the needle upon a predetermined partial rotation of the wheel.

FIG. 7 shows a pusher wire, according to an embodiment. A pusher wire 724 includes a proximal end 721 and a distal end 727. In some embodiments, the overall length of the pusher wire 724 is greater than two inches, for example, the overall length can be about 2.146"+/−0.020". As shown in FIG. 7, the distal end 727 of the pusher wire 724 can be rounded (e.g., hemispherical) such that the pusher wire 724 can move through a needle bore smoothly, damage to the implant can be prevented, and damage to the tissue of a patient's eye can be prevented. In some embodiments, the pusher wire 724 includes a roughened portion 723 extending from a proximal end of the pusher wire 724. The roughened portion 723 is roughened (e.g., etched, sanded, machined, etc.), for example, for adhesive bonding (e.g., when partially received in a pusher wire connector, as described herein). The length and gauge of the pusher wire 724 can be any suitable length and gauge. For example, different lengths and/or gauges may be selected depending on the number and/or size of the implants to be delivered. The pusher wire 724 can be the same or similar in structure and function to any of the pusher wires described herein, such as, for example, the pusher wires 124, 224, 324, and 424 described above.

Figure 8A:
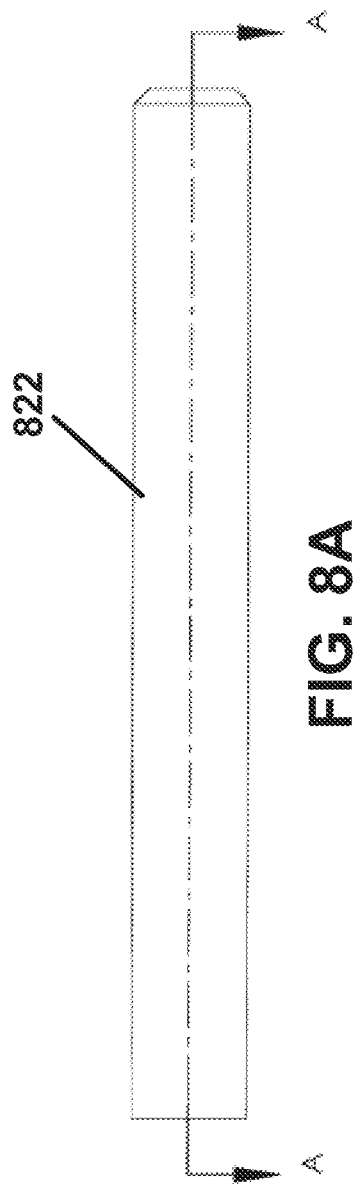
FIG. 8A shows a side view of a pusher wire connector, according to an embodiment.

FIG. 8A shows a side view of a pusher wire connector, according to an embodiment. As shown in FIG. 8A, the pusher wire connector 822 includes a flat proximal end (leftmost extent of the pusher wire connector 822 in FIG. 8A) and a distal end having a truncated taper or bevel (rightmost extent of the pusher wire connector 822 in FIG. 8A). In some embodiments, the overall length of the pusher wire connector is less than 0.5 inches, for example about 0.352". In some embodiments, the outer diameter of the pusher wire connector 822 is less than 0.05", for example about 0.039". In some embodiments, the truncated taper is about 45 degrees. The pusher wire connector 822 can comprise Absylux® or any other suitable material. The length and other dimensions (e.g., the inner diameters of recesses defined by the pusher wire connector 822) of the pusher wire connector 822 can be any suitable length and/or other dimensions. For example, different lengths and other dimensions may be selected depending on the number and/or size of the implants to be delivered. The pusher wire connector 822 can be the same or similar in structure and function to any of the pusher wire connectors described herein, such as, for example, the pusher wire connectors 122, 222, 322, and 422 described above.

Figure 8B:
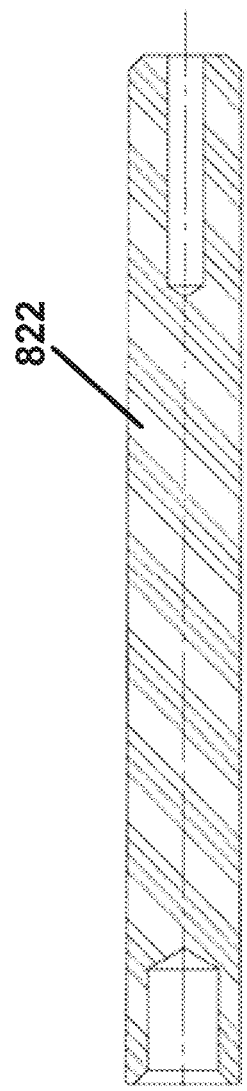
FIG. 8B shows a further side view of the pusher wire connector of FIG. 8A, in cross-section (taken along section line A-A of FIG. 8A).

FIG. 8B shows a further side view of the pusher wire connector of FIG. 8A, in cross-section (taken along section line A-A of FIG. 8A). A first recess is defined in the proximal (leftmost) end of the pusher wire connector 822, and includes a cone-shaped surface opposite its proximal end opening. The proximal end opening of the first recess has a truncated taper or bevel (e.g., 45 degrees) that begins at, or is spaced from, the circumferential outer surface of the pusher wire connector 822. In some embodiments, the first recess is configured to be coupled to an applicator device for actuation and delivery of one or more implants during use. A second recess is defined in the distal (rightmost) end of the pusher wire connector 822, and includes a cone-shaped surface opposite its distal end opening. The second recess is configured to be coupled to a pusher wire for delivery of one or more implants during use.

Figure 8D:
FIG. 8D shows a second end view of the pusher wire connector of FIG. 8 that is opposite the first end.
Figure 8C:
FIG. 8C shows a first end view of the pusher wire connector of FIG. 8.

FIG. 8C shows a first (proximal) end view of the pusher wire connector of FIG. 8. In some embodiments, the inner diameter of the first recess at the proximal end of the pusher wire connector 822 is less than 0.05", for example about 0.024"+/−0.001".

FIG. 8D shows a second (distal) end view of the pusher wire connector of FIG. 8 that is opposite the first end. In some embodiments, the inner diameter of the second recess at the distal end of the pusher wire connector 822 is less than 0.025", for example about 0.013"+/−0.001".

Figure 9A:
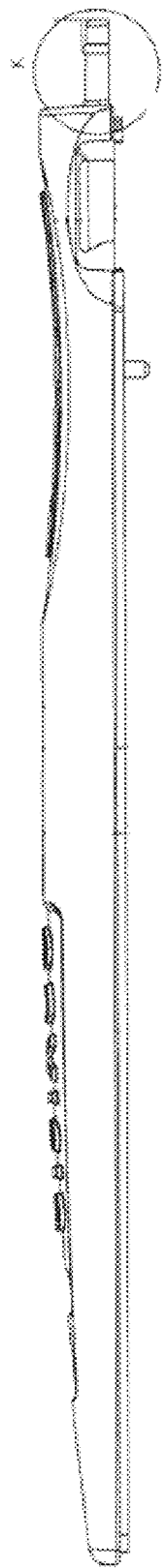
FIG. 9A shows a top view of a first outer portion of an applicator, or "handle," according to an embodiment.
Figure 9B:
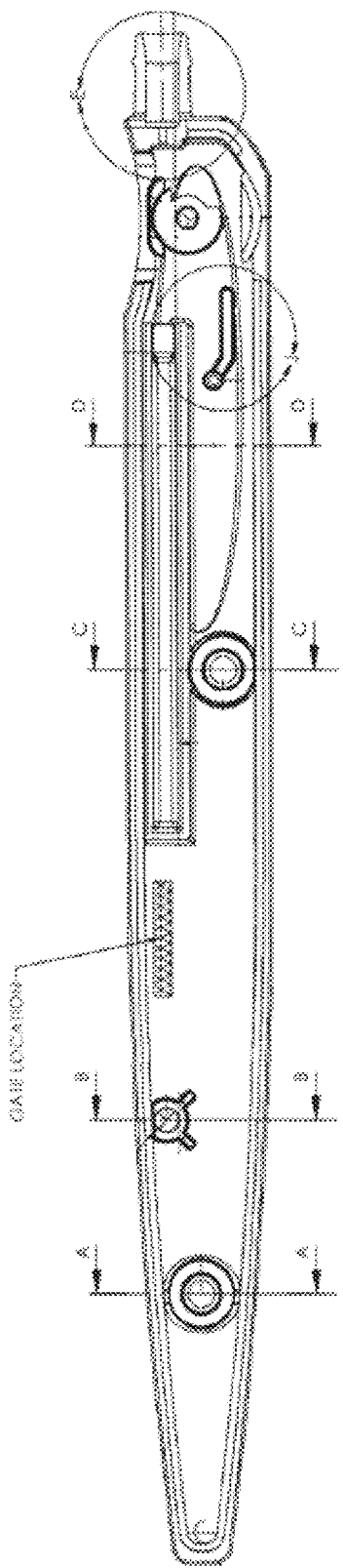
FIG. 9B shows a left side view of the applicator of FIG. 9A.
Figure 9C:
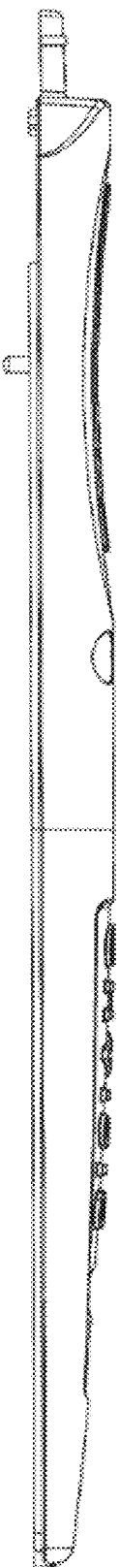
FIG. 9C shows a top view of a second outer portion of the applicator of FIG. 9A.
Figure 9D:
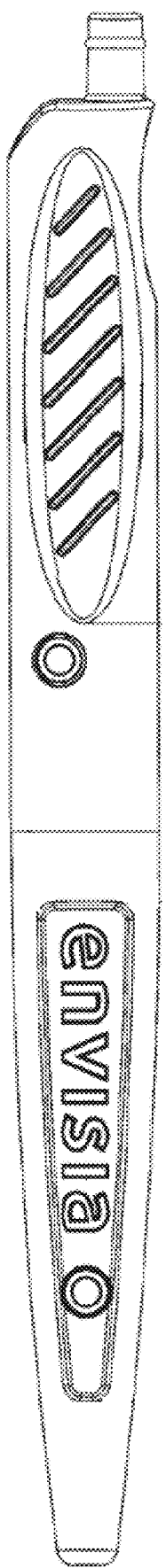
FIG. 9D shows a side view of the applicator of FIG. 9A.
Figure 9H:
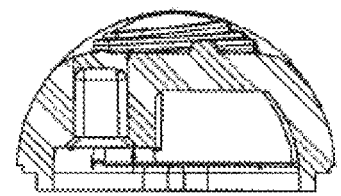
FIG. 9H shows a cross-sectional view of the applicator of FIG. 9A, taken along the section line D-D in FIG. 9B.
Figure 9G:
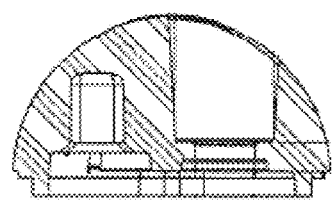
FIG. 9G shows a cross-sectional view of the applicator of FIG. 9A, taken along the section line C-C in FIG. 9B.
Figure 9F:
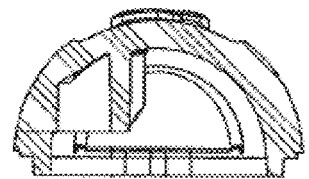
FIG. 9F shows a cross-sectional view of the applicator of FIG. 9A, taken along the section line B-B in FIG. 9B.
Figure 9E:
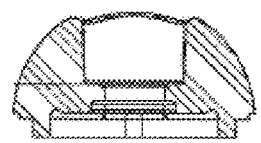
FIG. 9E shows a cross-sectional view of the applicator of FIG. 9A, taken along the section line A-A in FIG. 9B.
Figure 9K:
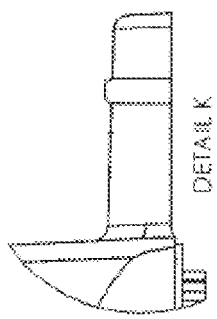
FIG. 9K shows a detail view of the applicator of FIG. 9A, within the circular section marked "DETAIL K" in FIG. 9A.
Figure 9J:
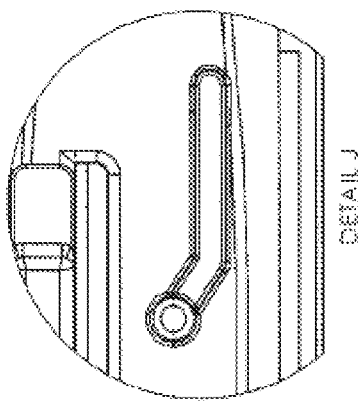
FIG. 9J shows a detail view of the applicator of FIG. 9A, within the circular section marked "DETAIL J" in FIG. 9B.
Figure 9I:
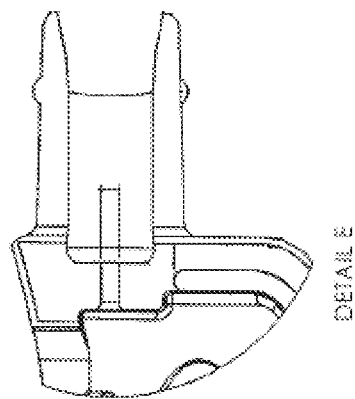
FIG. 9I shows a detail view of the applicator of FIG. 9A, within the circular section marked "DETAIL E" in FIG. 9B.

FIG. 9A shows a top view of a first outer portion of an exemplary applicator, or "handle," according to an embodiment. FIG. 9B shows a left side view of the applicator of FIG. 9A. FIG. 9C shows a top view of a second outer portion of the applicator of FIG. 9A. FIG. 9D shows a side view of the applicator of FIG. 9A. FIG. 9E shows a cross-sectional view of the applicator of FIG. 9A, taken along the section line A-A in FIG. 9B. FIG. 9F shows a cross-sectional view of the applicator of FIG. 9A, taken along the section line B-B in FIG. 9B. FIG. 9G shows a cross-sectional view of the applicator of FIG. 9A, taken along the section line C-C in FIG. 9B. FIG. 9H shows a cross-sectional view of the applicator of FIG. 9A, taken along the section line D-D in FIG. 9B. FIG. 9I shows a detail view of the applicator of FIG. 9A, within the circular section marked "DETAIL E" in FIG. 9B. FIG. 9J shows a detail view of the applicator of FIG. 9A, within the circular section marked "DETAIL J" in FIG. 9B. FIG. 9K shows a detail view of the applicator of FIG. 9A, within the circular section marked "DETAIL K" in FIG. 9A. The projection shown in FIGS. 9I and 9K includes male and female connections for connection with a needle hub of an implant delivery device, such as any of the implant delivery devices described herein.

Figure 10A:
FIG. 10A shows a top view of a first outer portion of an applicator, or "handle," according to an embodiment.
Figure 10B:
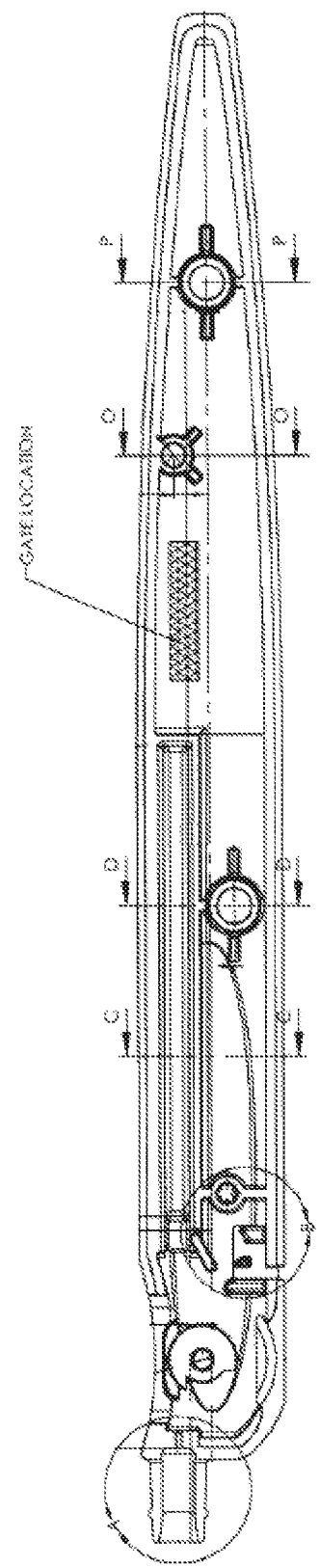
FIG. 10B shows a right side view of the applicator of FIG. 10A.
Figure 10C:
FIG. 10C shows a bottom view of a first outer portion of the applicator of FIG. 10A.
Figure 10D:
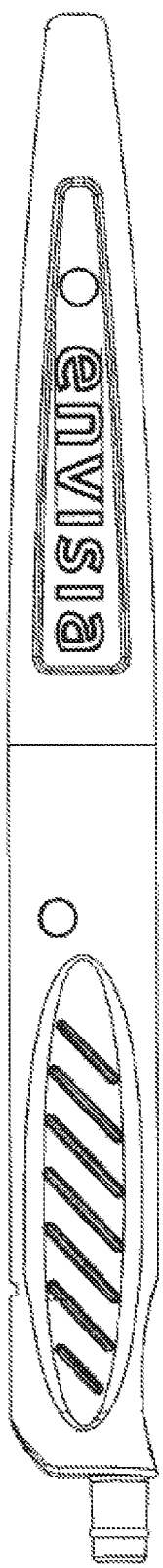
FIG. 10D shows a side view of the applicator of FIG. 10A.
Figure 10H:
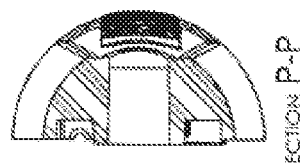
FIG. 10H shows a cross-sectional view of the applicator of FIG. 10A, taken along the section line P-P in FIG. 10B.
Figure 10G:
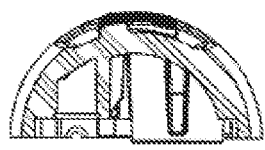
FIG. 10G shows a cross-sectional view of the applicator of FIG. 10A, taken along the section line O-O in FIG. 10B.
Figure 10F:
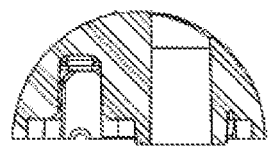
FIG. 10F shows a cross-sectional view of the applicator of FIG. 10A, taken along the section line D-D in FIG. 10B.
Figure 10E:
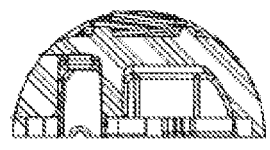
FIG. 10E shows a cross-sectional view of the applicator of FIG. 10A, taken along the section line C-C in FIG. 10B.
Figure 10K:
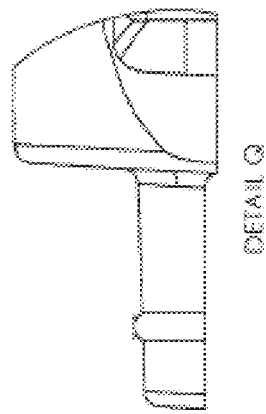
FIG. 10K shows a detail view of the applicator of FIG. 10A, within the circular section marked "DETAIL Q" in FIG. 10A.
Figure 10J:
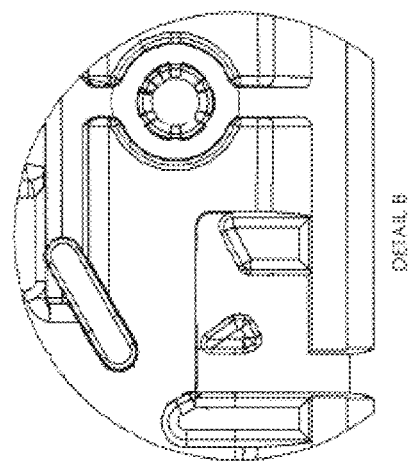
FIG. 10J shows a detail view of the applicator of FIG. 10A, within the circular section marked "DETAIL B" in FIG. 10B.
Figure 10I:
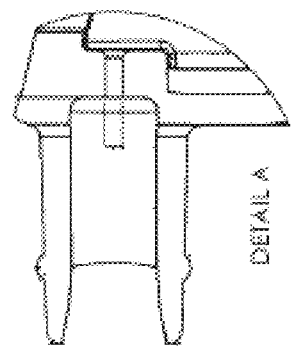
FIG. 10I shows a detail view of the applicator of FIG. 10A, within the circular section marked "DETAIL A" in FIG. 10B.

FIG. 10A shows a top view of a first outer portion of an applicator, or "handle," according to an embodiment. FIG. 10B shows a right side view of the applicator of FIG. 10A. FIG. 10C shows a top view of a second outer portion of the applicator of FIG. 10A. FIG. 10D shows a side view of the applicator of FIG. 10A. FIG. 10E shows a cross-sectional view of the applicator of FIG. 10A, taken along the section line C-C in FIG. 10B. FIG. 10F shows a cross-sectional view of the applicator of FIG. 10A, taken along the section line D-D in FIG. 10B. FIG. 10G shows a cross-sectional view of the applicator of FIG. 10A, taken along the section line O-O in FIG. 10B. FIG. 10H shows a cross-sectional view of the applicator of FIG. 10A, taken along the section line P-P in FIG. 10B. FIG. 10I shows a detail view of the applicator of FIG. 10A, within the circular section marked "DETAIL A" in FIG. 10B. FIG. 10J shows a detail view of the applicator of FIG. 10A, within the circular section marked "DETAIL B" in FIG. 10B. FIG. 10K shows a detail view of the applicator of FIG. 10A, within the circular section marked "DETAIL Q" in FIG. 10A. The projection shown in FIGS. 10I and 10K includes male and female connections for connection with a needle hub of an implant delivery device, such as some embodiments of the implant delivery devices described herein.

Figure 11:
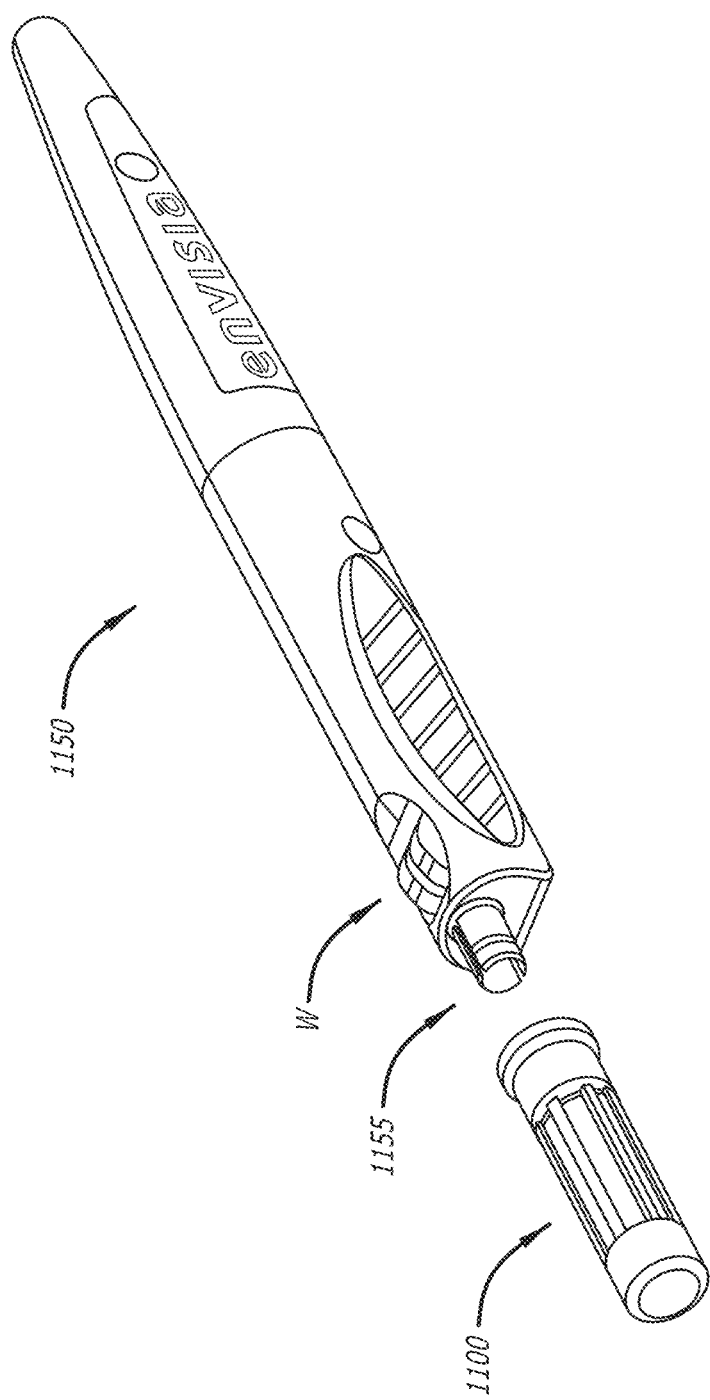
FIG. 11 shows a perspective view of an applicator and implant delivery apparatus prior to connection, according to some embodiments.
Figure 12:
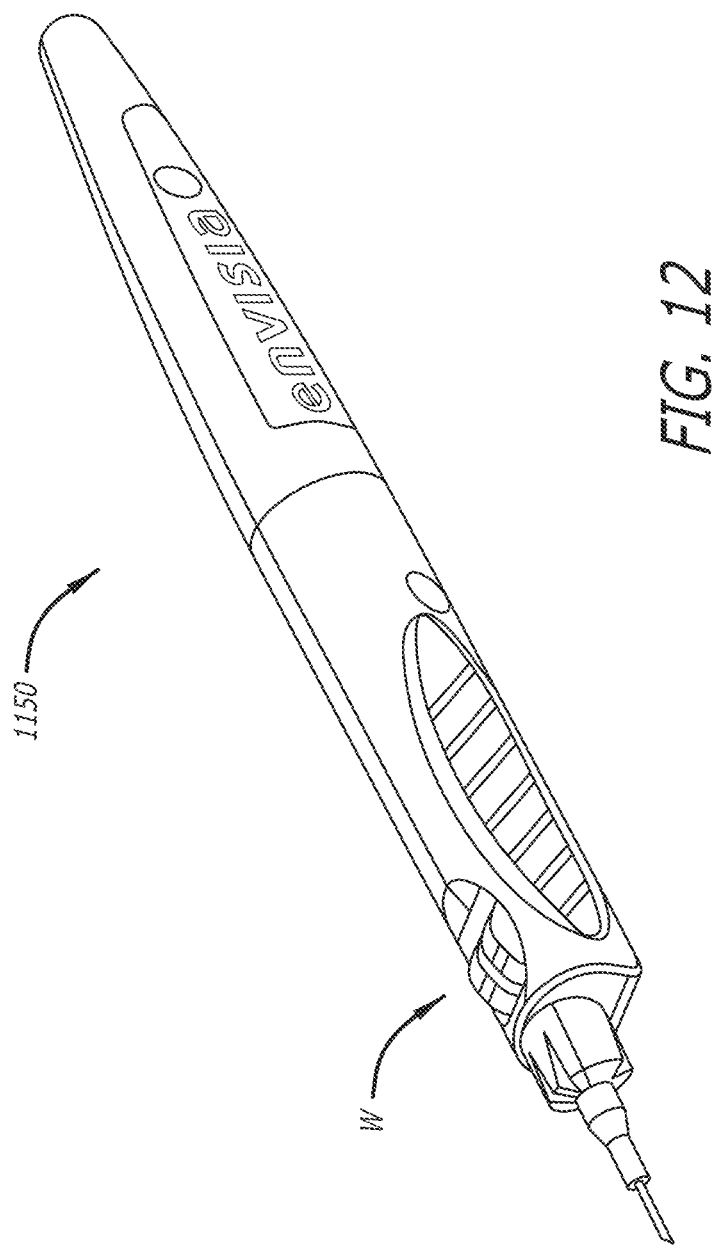
FIG. 12 shows the applicator of FIG. 11 with the implant delivery apparatus attached but with both the first cap and the second cap removed.

FIG. 11 shows a perspective view of an applicator and implant delivery apparatus prior to connection, according to some embodiments. As shown, the implant delivery apparatus 1100 is axially aligned with the applicator 1150 (which includes actuation wheel "W") prior to attachment. To load the implant delivery apparatus 1100, a physician manually inserts one or more implants into the needle of the implant delivery apparatus 1100 either after mounting the implant delivery apparatus 1100 onto the applicator 1150, or prior to mounting the implant delivery apparatus 1100 onto the applicator 1150 (e.g., by removing the first cap to expose the beveled end of the needle and, optionally, replacing the first cap once the implant(s) have been loaded). In some embodiments, the implant delivery apparatus 1100 (with or without the applicator 1150 and the first cap) must be inverted (i.e., held such that the needle tip is vertical and the bevel faces up) until use such that the implant does not prematurely dispense or fall out. Prior to delivering the one or more implants, the implant delivery apparatus 1100 is mechanically coupled to the connection region 1155 of the applicator 1150 via corresponding complementary male and female connections. FIG. 12 shows the applicator of FIG. 11 with the implant delivery apparatus attached but with the first cap and the second cap removed. During use, for each advancement of the wheel "W," a single implant is dispensed from the tapered end of the needle. It is to be understood that in some embodiments, the needle may not be beveled or may have a different configuration. However, it is to be understood that the reference to the beveled end of the needle is for the purposes of illustration and to indicate the portion of the needle configured to be applied to a tissue for treatment.

In some embodiments, needle hub subassemblies and needle hub assemblies (NHAs) of the present disclosure can include a needle that is preloaded, e.g., within an aseptic core, with implants that are retained within a needle bore prior to use. NHAs described herein can include a bristle disposed within (and, optionally, attached or secured to) a bristle retainer (e.g., via an adhesive or the like), as well as a "push pin" or "pusher wire" that, during use, engages with one or more implants disposed within the bore of the needle.

The pusher wire can also be configured to interface with an applicator so as to exhibit a "zero prime" feature, in that with each actuation of the applicator (e.g., with each predetermined angular rotation of a knob having multiple spaced detents or projections), a single implant (e.g., an ocular implant) is linearly advanced, either through direct or indirect contact with the pusher wire, out of the implant delivery apparatus.

Embodiments described herein relate generally to medical implant delivery apparatuses and methods. In some embodiments, an apparatus (e.g., an NHA) comprises a first cap, a second cap, a needle hub at least partially disposed within the second cap, and a needle including at least one implant disposed therewithin. The second cap has a proximal end, a distal end, and a longitudinal axis, and includes a bristle retainer at least partially disposed therewithin at the distal end thereof. The bristle retainer has a bristle at least partially disposed therewithin. The needle includes a first distal end and a second proximal end. The first end of the needle can be beveled, and the second end is disposed within a hub pocket of the needle hub. The first cap is connected to the needle hub, and is disposed at a proximal end of the first cap. The needle and the at least one implant are substantially aligned with one another along the longitudinal axis of the first cap.

In some embodiments, the apparatus further comprises a pusher wire that is disposed within the needle hub and is configured to engage, upon attachment to an applicator and during use, with an actuator of the applicator. The bristle retainer can include a bristle retainer hub having one or more ribs on an exterior surface thereof. The one or more ribs of the bristle retainer can be configured to interference fit with the second cap. The needle hub can include one or more ribs on an exterior surface thereof. The one or more ribs of the needle hub can be configured for interference fit with the first cap. In some embodiments, the needle and the needle hub are attached, connected or fixed to one another, such as with an adhesive or the like. In some embodiments, the bristle is partially fixed within the bristle retainer (e.g., via an adhesive).

In some embodiments, a method comprises inserting an elongate portion of a load tool into a needle subassembly such that the elongate portion of the load tool substantially aligns with a longitudinal axis of the needle subassembly. The method also includes inserting an implant in a first opening of the load tool, inserting an elongate portion of a pusher tool into the first opening of the load tool such that the implant is at least partially received within a bore of a needle of the needle subassembly, and removing the load tool from the needle subassembly. The elongate portion of the load tool can be inserted into the needle subassembly at a proximal end of the needle subassembly. In some embodiments, the method further comprises connecting a cap to the proximal end of the needle subassembly after removing the load tool from the needle subassembly.

Figure 13A:
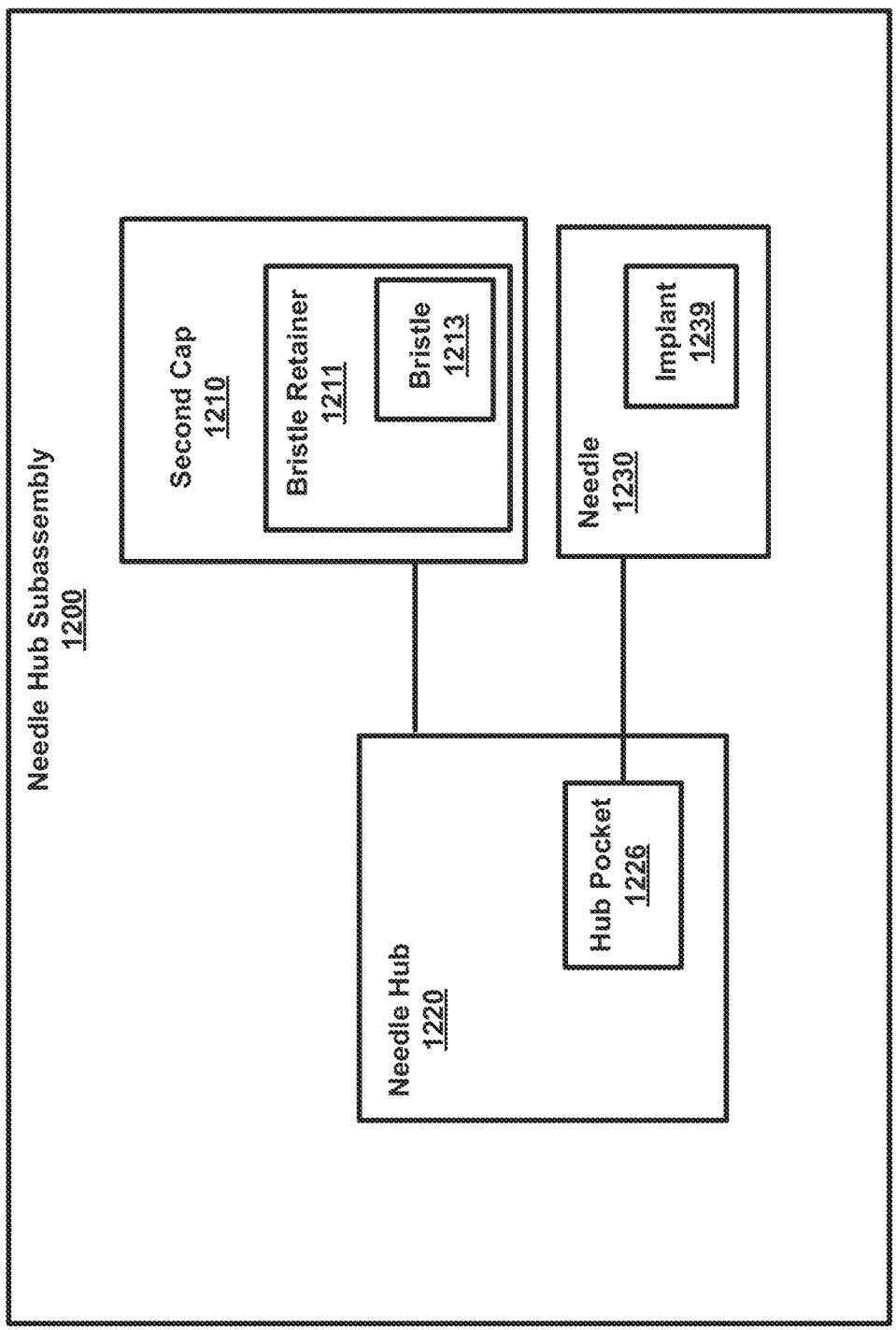
FIG. 13A is a schematic block diagram of a needle hub subassembly, according to an embodiment.

Turning now to FIG. 13A, a schematic block diagram of a needle hub subassembly, according to an embodiment, is shown. The needle hub subassembly 1200 includes a second cap 1210 having a bristle retainer 1211 disposed at least partially therein (e.g., protruding therefrom, as shown and discussed below). The bristle retainer 1211 can include a bristle 1213 disposed therewithin. The second cap 1210 is connected to a needle hub 1220 (e.g., the needle hub 1220 is at least partially received within the second cap 1210, and/or the needle hub 1220 is mechanically fastened to the second cap 1210). The needle hub 1220 includes a hub pocket 1226, such as a recess or orifice defined in the needle hub 1220. A needle 1230 is connected to the needle hub 1220 via the hub pocket 1226. For example, the needle 1230 is connected to the needle hub 1220 by virtue of being partially disposed within the hub pocket 1226. The needle 1230 includes one or more implants 1239 disposed within a central bore. In some embodiments, the implants 1239 can be loaded into the needle 1230 in an aseptic or sterile environment prior to use, shipping, packaging, etc.

Figure 13B:
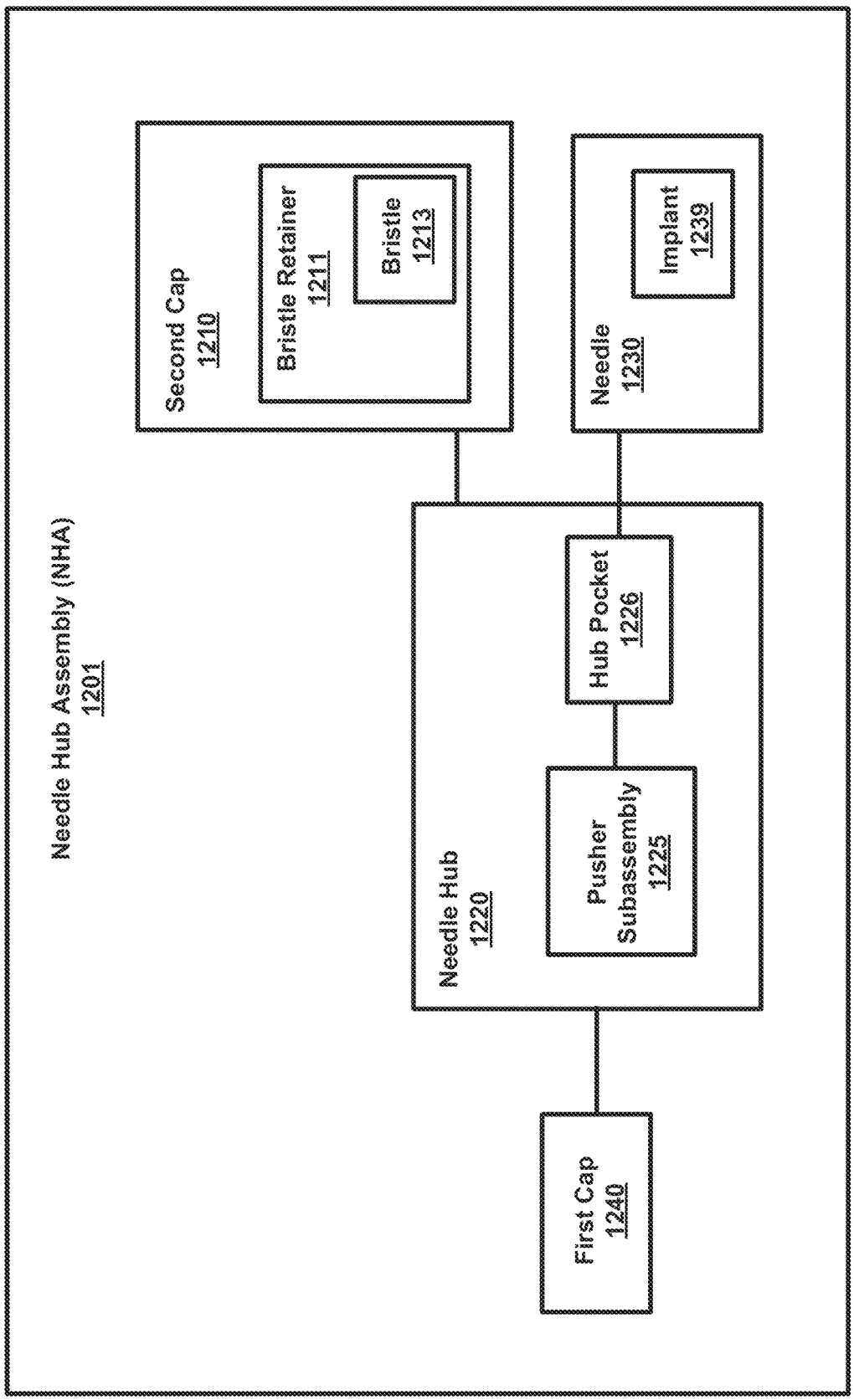
FIG. 13B is a schematic block diagram of a needle hub assembly (NHA), according to an embodiment.

FIG. 13B is a schematic block diagram of a needle hub assembly (NHA), also referred to herein as an implant delivery apparatus, according to an embodiment. The NHA 1201 includes the components of FIG. 13A, but further includes a pusher subassembly 1225, which in some embodiments includes a pusher wire connector (not shown) and a pusher wire (not shown). The NHA also includes a first cap 1240 that is mechanically connected to the needle hub 1220. For example, the needle hub 1220 may be received at least partially within the first cap 1240. In some embodiments, the first cap 1240 is not present and the needle hub assembly 1201 can be pre-loaded with one or more implants. In such embodiments, the needle hub assembly 1201 can be connected directly to a handle of an applicator device, such as one of the applicator devices shown in FIGS. 9A-11.

Figure 14:
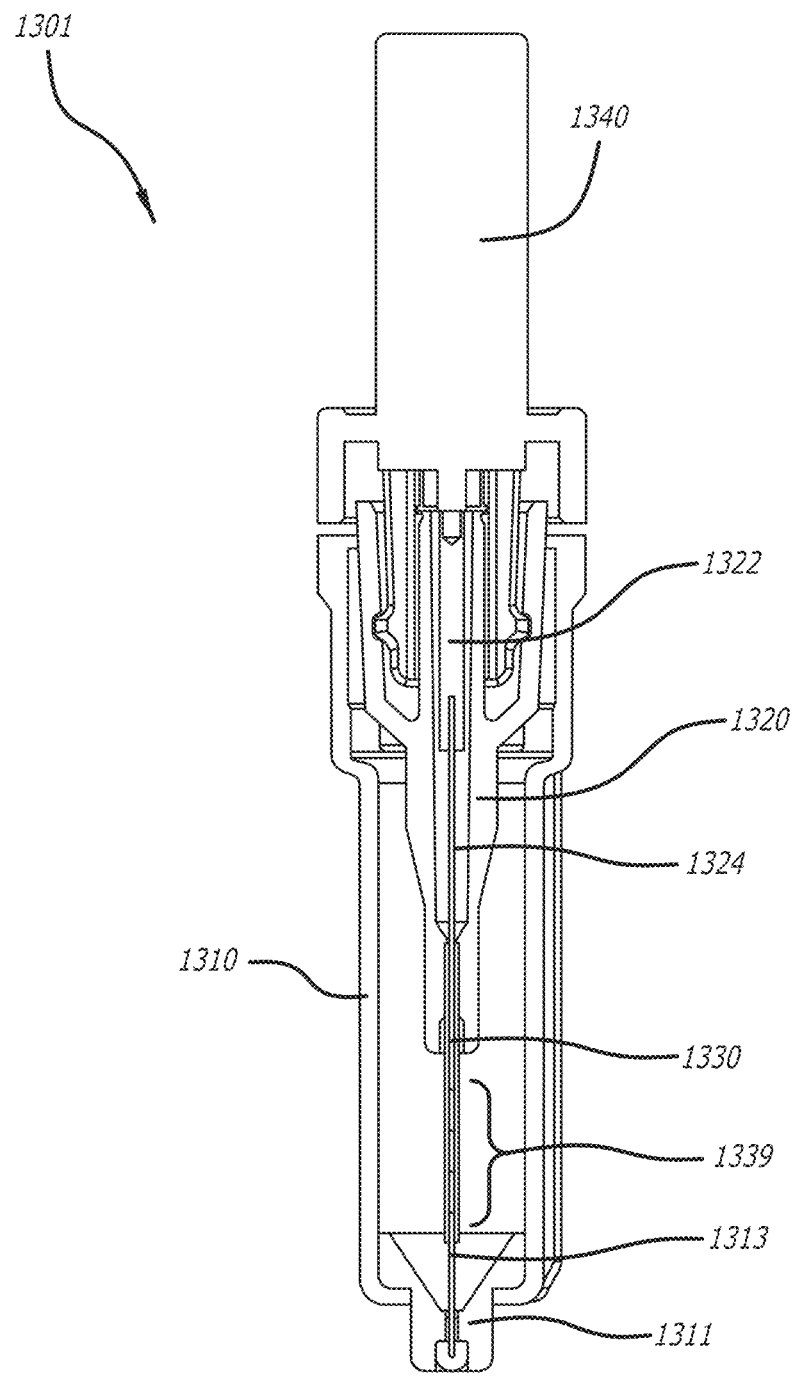
FIG. 14 shows a cross-sectional side view of an assembled NHA, according to an embodiment.

FIG. 14 shows a cross-sectional side view of a completely assembled NHA, according to an embodiment. As shown in FIG. 14, an NHA 1301 includes a second cap 1310. The second cap 1310 includes a bristle retainer 1311 disposed partially within the first cap 1310, but protruding through an opening in the second cap 1310 at a distal end thereof. The bristle retainer 1311 houses a bristle 1313, and the bristle 1313 is optionally held in place within an orifice of the bristle retainer 1311, for example, via a bead of adhesive within a recess of the distal end of the bristle retainer 1311. A needle hub 1320 is disposed substantially wholly within the second cap 1310 (i.e., the needle hub 1320 protrudes slightly at the proximal end opening of the second cap 1310), and a first cap 1340 is mechanically connected to the needle hub 1320 via corresponding complementary male and female connections. Within a central axial orifice of the needle hub 1320 is a pusher wire connector 1322 and a pusher wire 1324 that is partially disposed within a distal recess or channel defined within the pusher wire connector 1322. A needle 1330 is partially received in a hub pocket (not identified) of the needle hub 1320, and a plurality of implants 1339 (in this exemplary case, three) are disposed within the central bore of the needle 1330. In some embodiments, the bristle 1313 (and, optionally, also the glue that secures the bristle 1313 within the bristle retainer 1311) serves as a distal stop for the implants 1339, such that they do not fall out of the needle 1330 during transport and/or handling, and can keep the implants 1339 sterile up until the moment of use.

Figure 15C:
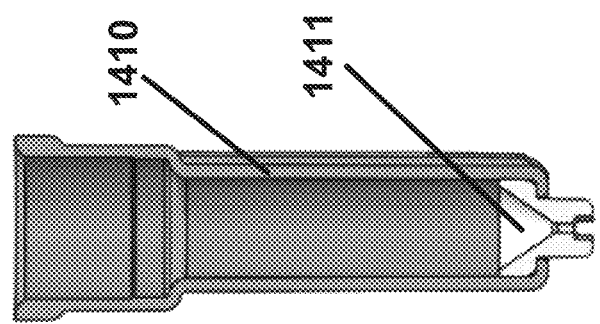
FIG. 15C shows an assembly sequence for a second cap and a bristle retainer, according to an embodiment.
Figure 15B:
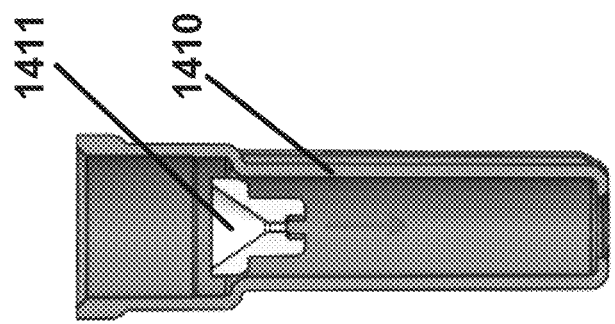
FIG. 15B shows an assembly sequence for a second cap and a bristle retainer, according to an embodiment.
Figure 15A:
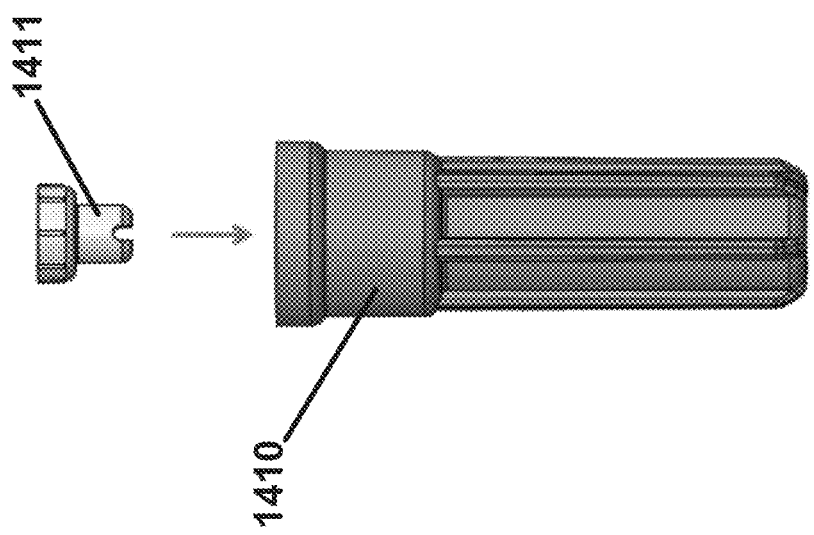
FIG. 15A shows an assembly sequence for a second cap and a bristle retainer, according to an embodiment.

FIGS. 15A-15C show an assembly sequence for a second cap and a bristle retainer, according to an embodiment. FIG. 15A shows as external view of the components, while FIGS. 15B and 15C show cross-sectional views thereof. As shown, a bristle retainer 1411 is first inserted into an open, proximal end of a second cap 1410. The bristle retainer 1411 is then moved (by gravity or by manually pushing it) down to a distal end of the second cap 1410, the distal end being opposite the proximal end. The distal end of the second cap 1410, as shown in FIGS. 15B and 15C, defines an opening through which a portion of the bristle retainer 1411 projects. In some embodiments, interference "ribs" on the bristle retainer 1411 (also referred to as a "hub") engage the second cap 1410 (also referred to as an "open ended cap") to secure it in place.

Figure 16D:
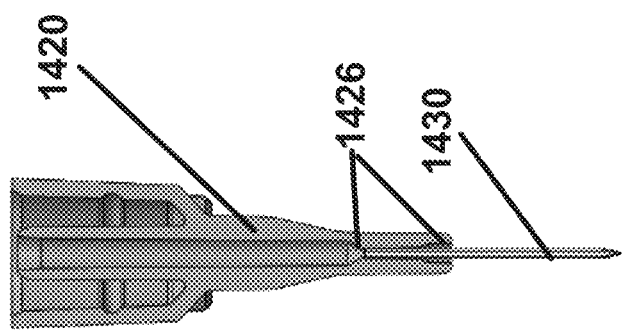
FIG. 16D shows an assembly sequence for a needle hub and a needle, according to an embodiment.
Figure 16C:
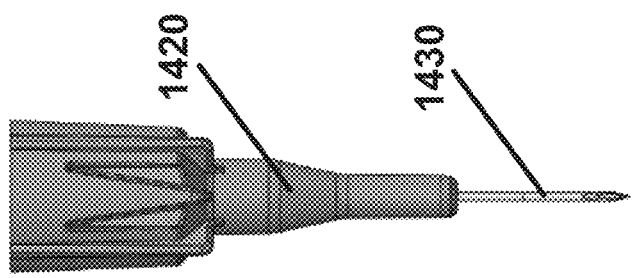
FIG. 16C shows an assembly sequence for a needle hub and a needle, according to an embodiment.
Figure 16B:
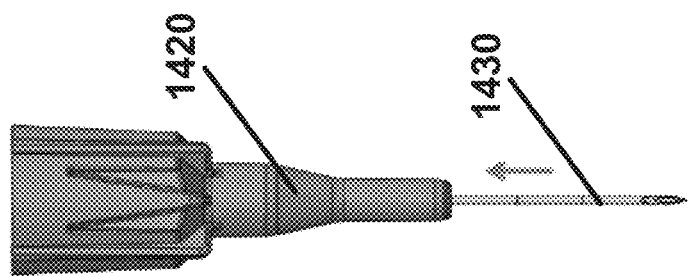
FIG. 16B shows an assembly sequence for a needle hub and a needle, according to an embodiment.
Figure 16A:
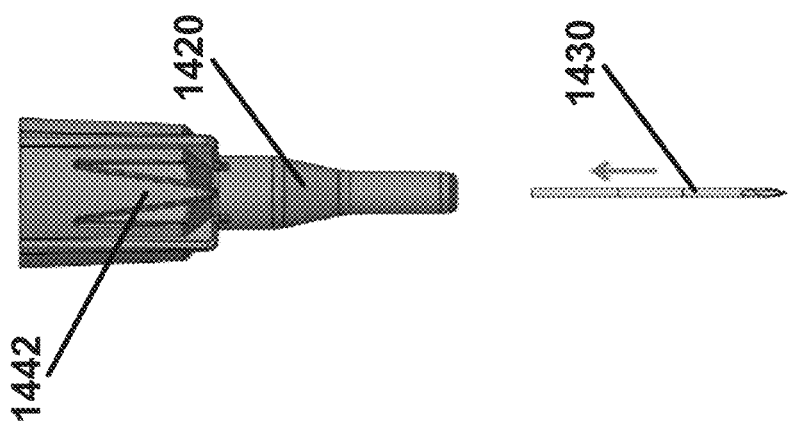
FIG. 16A shows an assembly sequence for a needle hub and a needle, according to an embodiment.

FIGS. 16A-16D show an assembly sequence for a needle hub and a needle, according to an embodiment. FIGS. 16A-16C show external views of the components, while FIG. 16D shows a cross-sectional view thereof. As shown, a needle 1430 is moved upwardly towards a needle hub 1420 until it is received within a hub pocket 1426 of the needle hub 1420. In some embodiments, an adhesive (e.g., a UV-curable adhesive) is used to secure the needle 1430 within the hub pocket 1426. In some embodiments, the needle 1430 "bottoms out" in the hub pocket 1426. In other words, the needle 1430 is inserted into the hub pocket 1426 until it reaches a mechanical stop. In some embodiments, the bevel of the needle 1430 and the indicator arrow 1442 on the needle hub 1420 are aligned during assembly to ensure proper orientation of the needle.

Figure 17C:
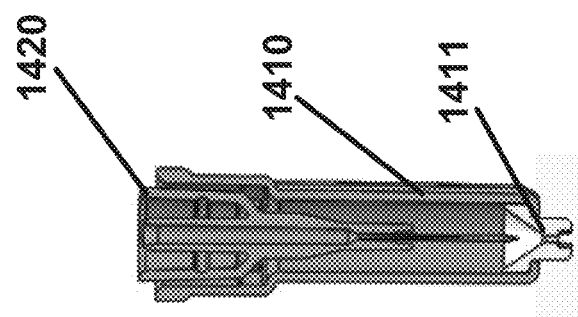
FIG. 17C shows an assembly sequence for the needle hub/needle combination of FIG. 16D and the second cap/bristle retainer of FIG. 15C, according to an embodiment.
Figure 17B:
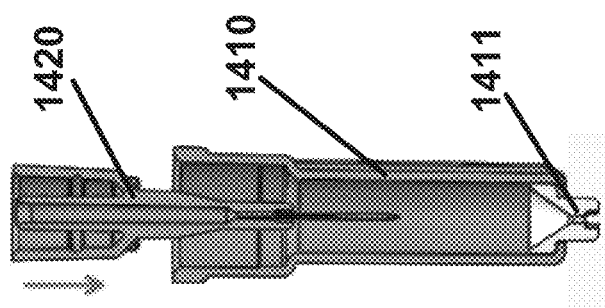
FIG. 17B shows an assembly sequence for the needle hub/needle combination of FIG. 16D and the second cap/bristle retainer of FIG. 15C, according to an embodiment.
Figure 17A:
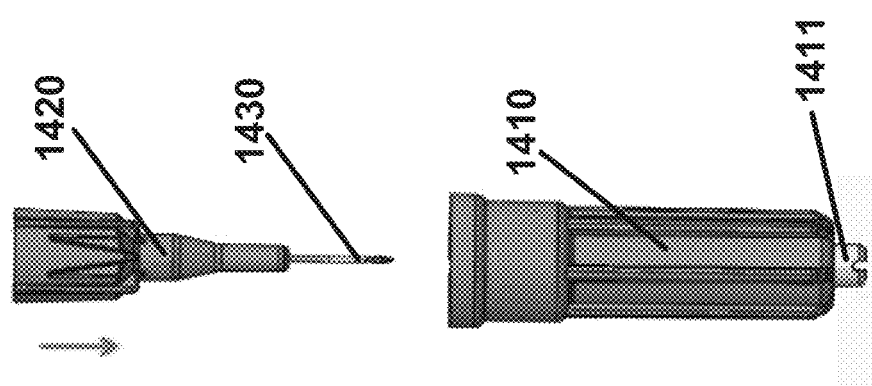
FIG. 17A shows an assembly sequence for the needle hub/needle combination of FIG. 16D and the second cap/bristle retainer of FIG. 15C, according to an embodiment.

FIGS. 17A-17C show an assembly sequence for the needle hub/needle combination of FIG. 16D and the second cap/bristle retainer of FIG. 15C, according to an embodiment. As shown, the needle hub 1420, with needle 1430 already installed, is inserted into the proximal open end of the second cap 1410, which already includes the bristle retainer 1411 at a distal end thereof, as discussed above. In some embodiments, interference ribs on the needle hub 1420 engage the second cap 1410 to secure the components in place.

The sequence of FIGS. 18A-18C shows the insertion of a load tool or "fixture" into a needle hub subassembly, according to an embodiment. As shown, a load fixture 1460 (also referred to as a loading tool, loading fixture, or load tool), which itself includes a centrally-disposed longitudinal orifice and a funnel-shaped proximal/top end, is inserted into an orifice in the needle hub 1420. The load fixture 1460 can be designed to bottom out at the top of the needle hub subassembly (i.e., at the top of the needle hub 1420 in FIGS. 18A-18C). The funneled top of the load fixture 1460 can facilitate ease of loading of bristles and/or implants into the needle hub subassembly. The load fixture 1460 can be configured to be self-centering within the needle hub subassembly.

FIGS. 19A-19D show a process sequence for the loading of a bristle into a needle hub subassembly, according to an embodiment. As shown, a bristle 1413 is inserted into the load fixture 1460 (which is connected to a needle hub subassembly, as shown and described with reference to FIGS. 18A-18C) and travels down a series of axially-aligned orifices in the load fixture 1460, the needle hub 1420, and the bristle retainer 1411, until the bristle is disposed within a distal end of the needle hub subassembly, and its distal tip is substantially aligned with the distal end of the projecting portion of the bristle retainer 1411. In some embodiments, the distal end of the bristle is secured in place, e.g., secured in place with an adhesive. In some embodiments, a pusher wire is inserted into the load fixture 1460 after the bristle 1413 and pushed through the sequence of orifices to assist in the advancement and/or positioning of the bristle 1413. In some embodiments, the needle hub assembly is configured such that the sequence of orifices are axially aligned with one another along a longitudinal axis of the needle hub subassembly (e.g., the central longitudinal axis thereof). FIGS. 20A and 20B show cross-sectional and exterior views, respectively, of the bristle 1413 disposed within the bristle retainer 1411. As shown in FIGS. 20A and 20B, an adhesive 1415 can secure the distal end of the bristle 1413 in place relative to the bristle retainer 1411. FIG. 20C shows an exterior view of the needle hub subassembly, including the bristle retainer 1411, with the load fixture 1460 removed.

Figure 21:
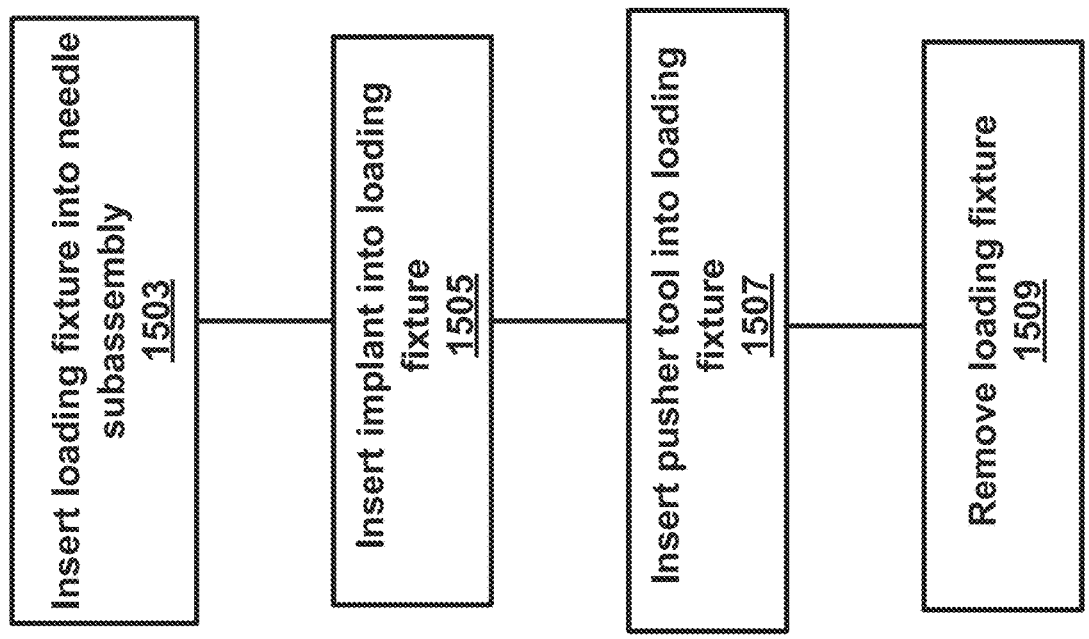
FIG. 21 shows a flow diagram of a method for introducing implants into a needle hub subassembly, according to an embodiment.

FIG. 21 shows a flow diagram of a method for introducing implants into a needle hub subassembly, according to an embodiment. As previously described, a loading fixture (also referred to as a loading tool, load fixture, or load tool) is inserted into a needle subassembly (1503). One or more implants are then inserted, at 1505, into the loading fixture, and a pusher tool (e.g., a pusher wire) is inserted into the loading fixture (1507) to advance the one or more implants to a desired location within the needle hub subassembly. The loading fixture is then removed (1509).

Figure 22A:
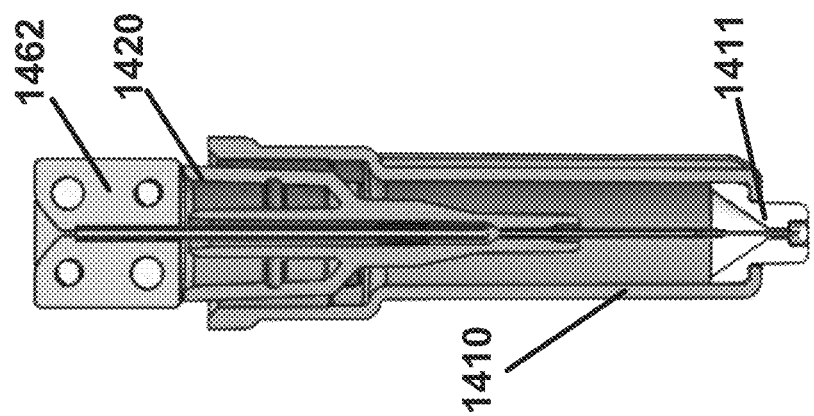
FIG. 22A shows the insertion of a loading fixture into a needle hub subassembly, according to an embodiment.
Figure 22B:
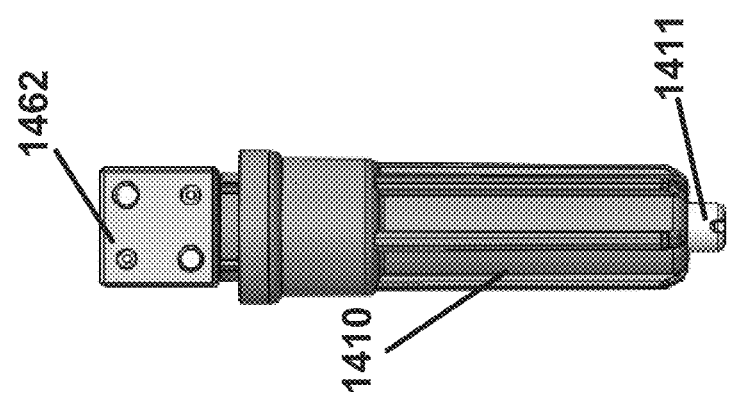
FIG. 22B shows the insertion of a loading fixture into a needle hub subassembly, according to an embodiment.
Figure 22C:
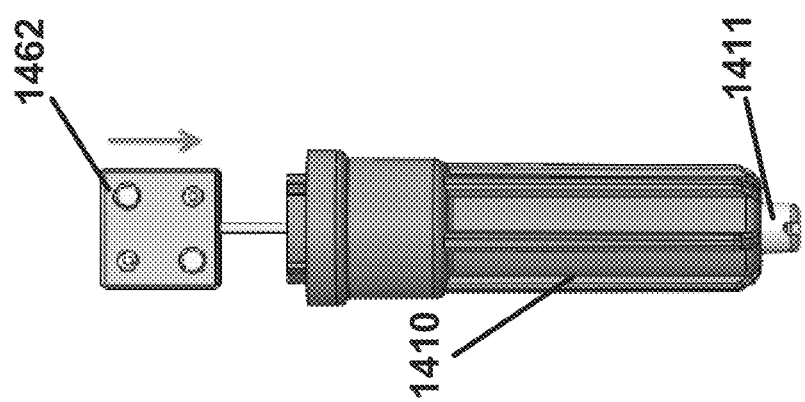
FIG. 22C shows the insertion of a loading fixture into a needle hub subassembly, according to an embodiment.
Figure 22D:
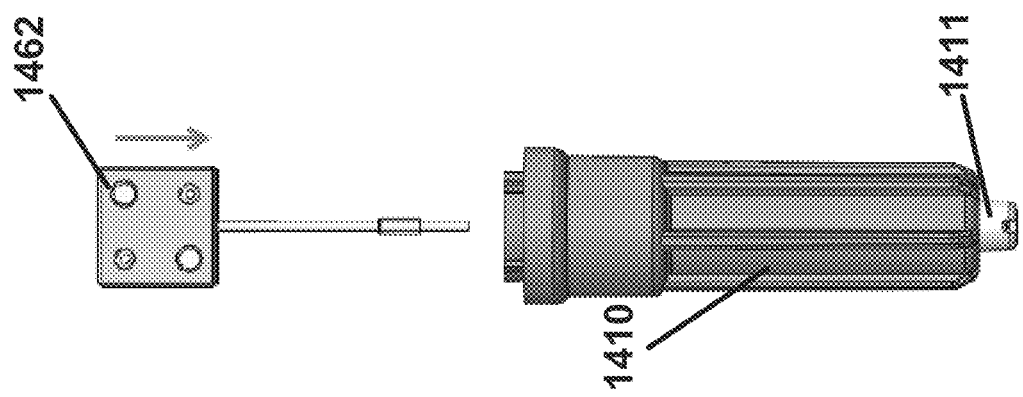
FIG. 22D shows the insertion of a loading fixture into a needle hub subassembly, according to an embodiment.
Figure 23C:
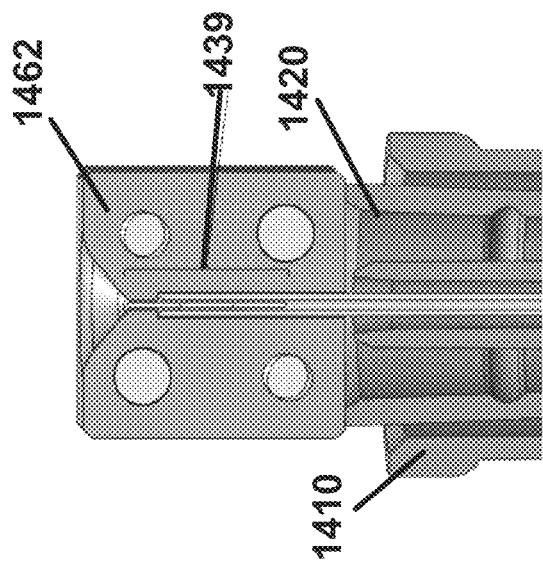
FIG. 23C shows a process sequence for the loading of implants into a needle hub subassembly, according to an embodiment.
Figure 23B:
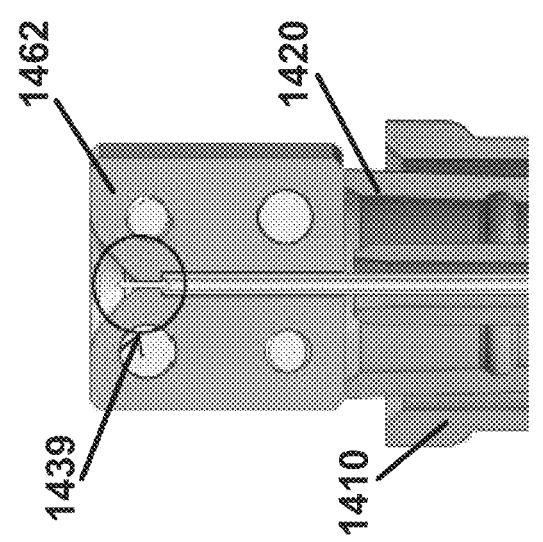
FIG. 23B shows a process sequence for the loading of implants into a needle hub subassembly, according to an embodiment.
Figure 23A:
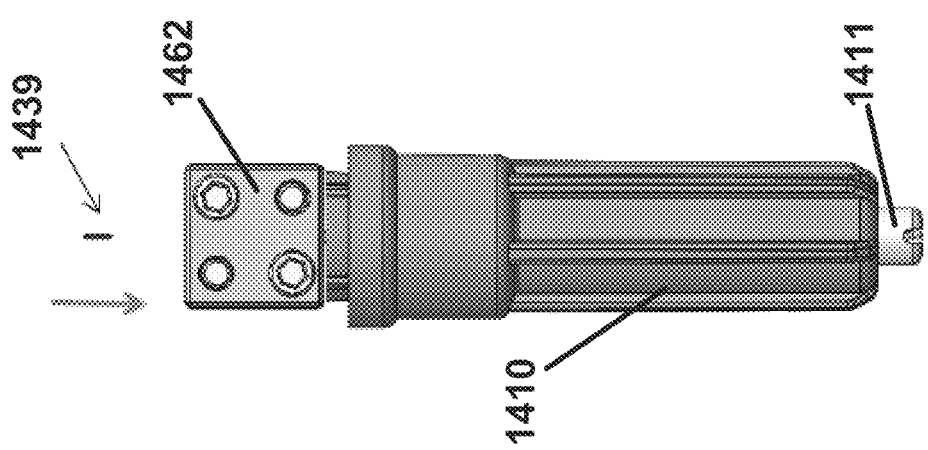
FIG. 23A shows a process sequence for the loading of implants into a needle hub subassembly, according to an embodiment.

FIGS. 22A-22D show the insertion of a loading fixture 1462 into a needle hub subassembly (including second cap 1410, bristle retainer 1411, and needle hub 1420), according to an embodiment. FIGS. 22A-22C show external views of the components, while FIG. 22D shows a cross-sectional view thereof. FIGS. 23A-23C show a process sequence for the loading of implants into a needle hub subassembly, according to an embodiment. FIG. 23A shows an external view of the components, while FIGS. 23B and 23C show cross-sectional views thereof. In some embodiments, the implants 1439 are placed into the proximal, funnel-shaped end of the loading fixture 1462 (also referred to as a loading tool, load fixture, or load tool). In some cases, implants can travel through the sequence of orifices in the needle hub subassembly with the assistance of neighbor/adjacent implants (i.e., they can "push" each other through the orifices). FIG. 23B shows a single implant 1439 entering the proximal funnel-end of the loading fixture 1462, and FIG. 23C shows a sequence of three implants 1439 abutting one another within the loading fixture 1462.

Figure 24C:
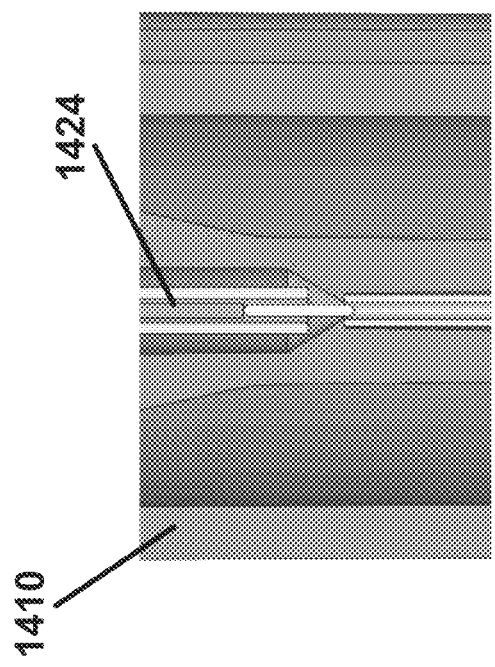
FIG. 24C shows a process sequence for the insertion of a pusher wire, according to an embodiment.
Figure 24B:
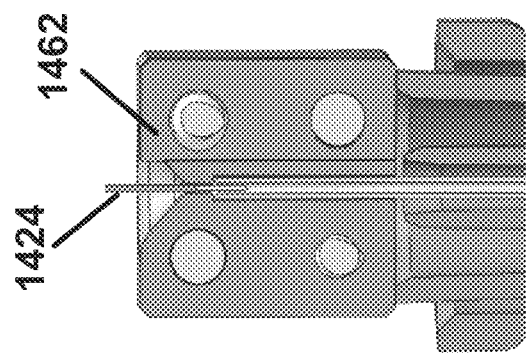
FIG. 24B shows a process sequence for the insertion of a pusher wire, according to an embodiment.
Figure 24A:
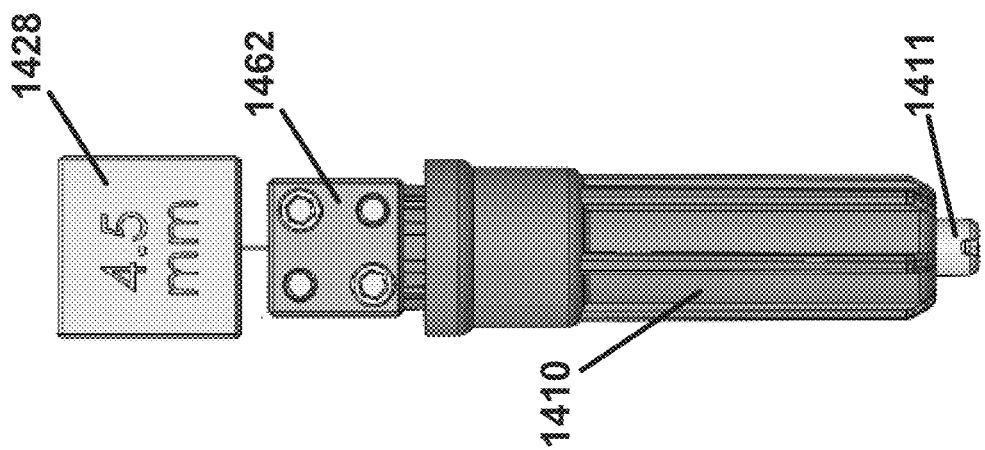
FIG. 24A shows a process sequence for the insertion of a pusher wire, according to an embodiment.
Figure 25B:
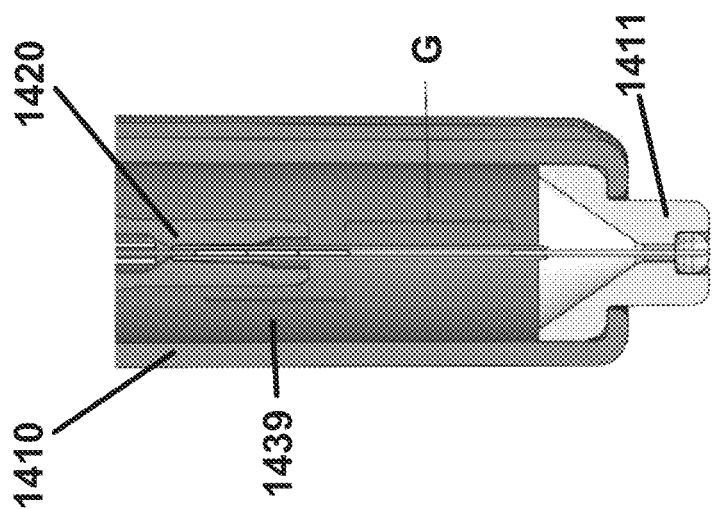
FIG. 25B shows a cross-sectional view of the partially assembled needle hub subassembly of FIG. 25A.
Figure 25A:
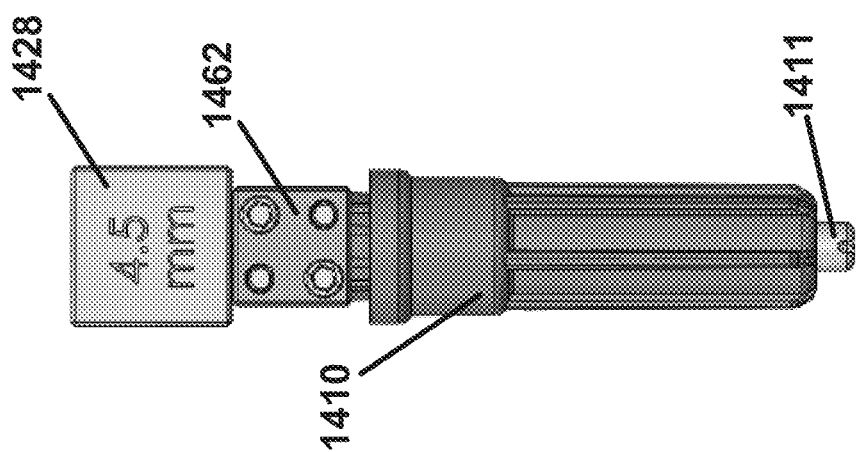
FIG. 25A shows an outer view of a partially assembled needle hub subassembly with the load tool installed, according to an embodiment.
Figure 26B:
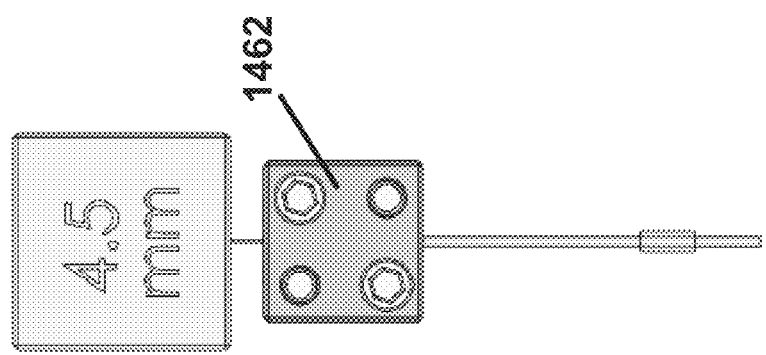
FIG. 26B shows the load tool of the needle hub subassembly of FIG. 25A.
Figure 26A:
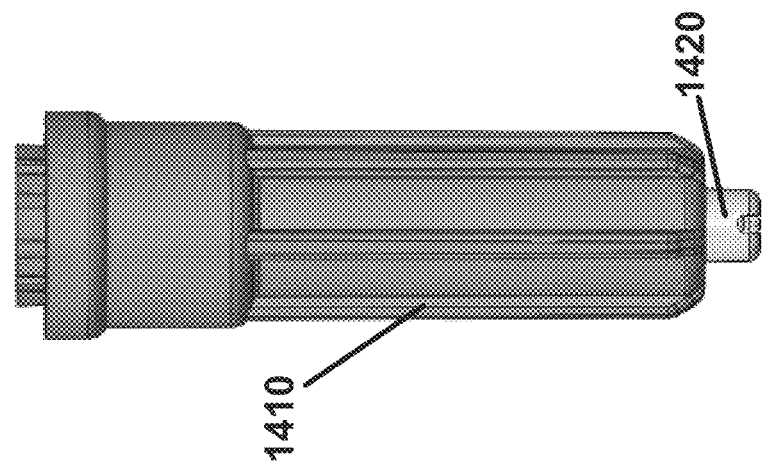
FIG. 26A shows an outer view of the needle hub subassembly of FIG. 25A, but with the load tool (shown in FIG. 26B) removed.
Figure 28A:
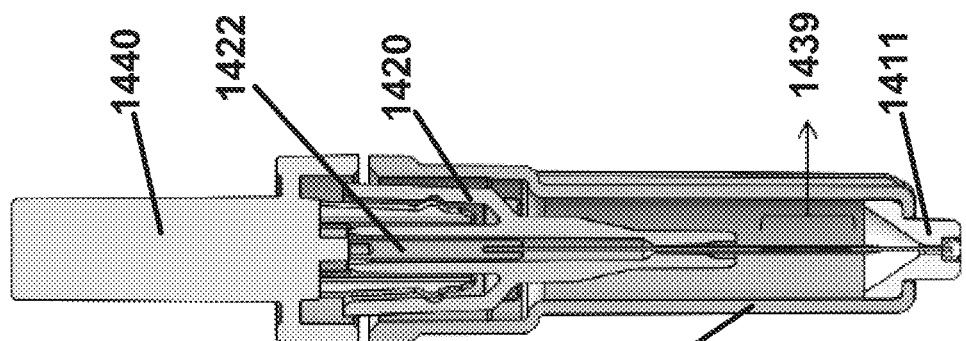
FIG. 28A shows a process sequence for the attachment of a first cap, according to an embodiment.
Figure 28B:
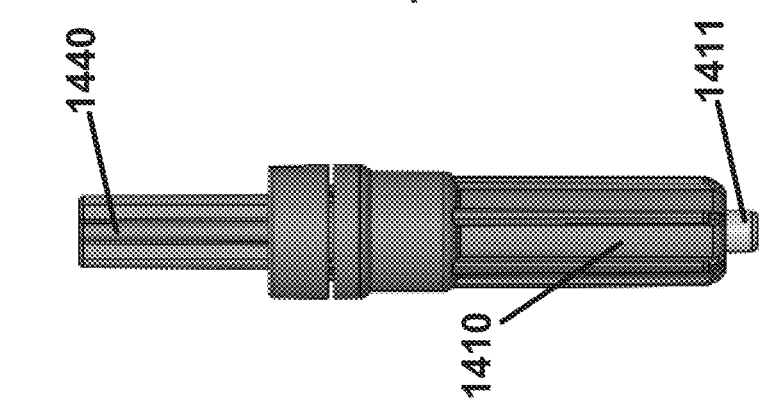
FIG. 28B shows a process sequence for the attachment of a first cap, according to an embodiment.
Figure 28C:
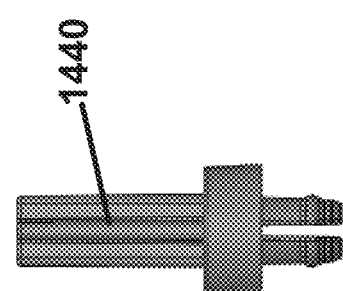
FIG. 28C shows a process sequence for the attachment of a first cap, according to an embodiment.
Figure 28D:
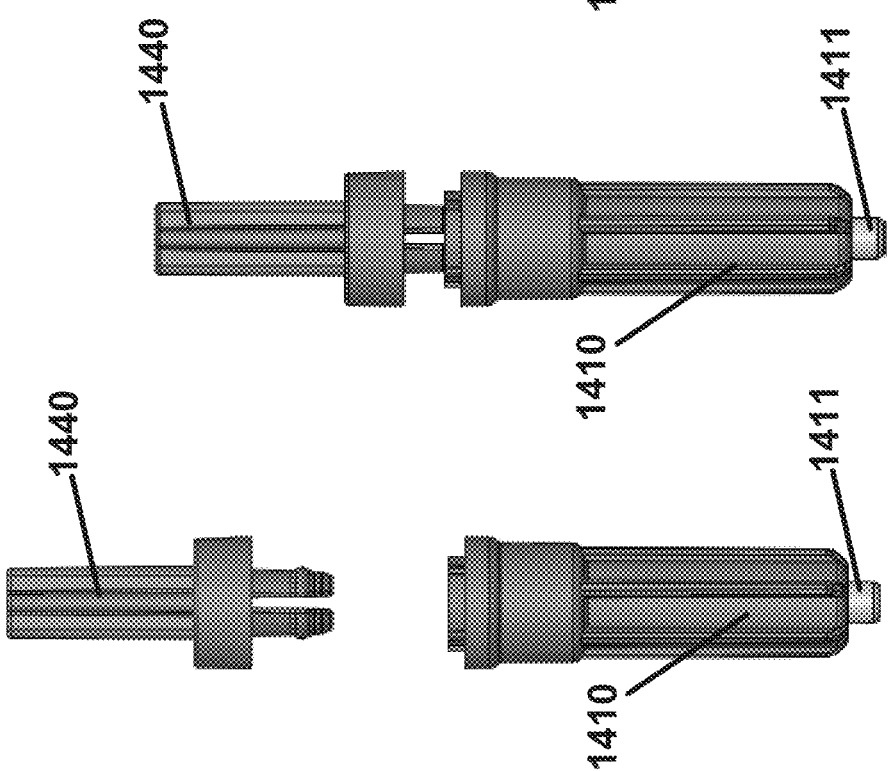
FIG. 28D shows a process sequence for the attachment of a first cap, according to an embodiment.

FIGS. 24A-24C show a process sequence for the insertion of a pusher wire, according to an embodiment. FIG. 24A shows an external view of the components, while FIGS. 24B and 24C show cross-sectional views thereof. As shown in FIG. 24B, a pusher wire 1424 (optionally connected to a pusher wire connector (not shown)) is inserted into the proximal, funnel end of the loading fixture 1462. As shown in FIG. 24A, the pusher wire 1424 can have an attached "tab" 1428 to control the depth of insertion of the pusher wire 1424. Multiple implants can be pushed simultaneously using the pusher wire 1424. FIG. 25A shows an outer view of a partially assembled needle hub subassembly with the loading fixture 1462 and the tabbed pusher wire (i.e., the tab 1428 and the pusher wire (not shown)) installed, according to some embodiments. FIG. 25B shows a cross-sectional view of the partially assembled needle hub subassembly of FIG. 25A. As can be seen in FIG. 25B, the implants 1439 have entered the needle hub 1420, and a gap G exists between the bristle retainer 1411 and the first (distalmost) implant 1439. In some embodiments, the pusher wire 1424 is not configured to seat the implants against the distal stop of the bristle, however the pusher wire 1424 ensures that the implants are within the needle bore prior to use. FIG. 26A shows an outer view of the needle hub subassembly of FIG. 25A, but with the loading fixture (shown in FIG. 26B) removed.

FIGS. 27A-27D show a process sequence for the insertion of a pusher subassembly after insertion of implants, and after removal of the loading fixture, according to an embodiment. The pusher subassembly 1425 includes the pusher wire connector 1422 and the pusher wire 1424. The pusher wire 1424 is inserted into the sequence of orifices in the needle hub subassembly to complete the placement of the implant (s) in the needle (e.g., advancing the implant(s) until they reach the bristle 1413, which acts as a distal stop).

FIGS. 28A-28D show a process sequence for the attachment of a first cap, according to an embodiment. Attachment of the first cap 1440 completes the assembly of the NHA. The first cap 1440 ensures that the pusher wire subassembly (which remains within the NHA, e.g., during shipping, packaging, etc.) is contained and in position.

FIG. 29 is an exploded perspective view of a delivery apparatus used to deliver a drug and/or implant to a patient. As shown in FIG. 29, an injector assembly 1502 includes an applicator 1550 and a needle hub subassembly 1500. The applicator 1550 can be used with any of the needle hub subassemblies described herein to deliver a drug to an eye of a patient. Said another way, the needle hub subassembly 1500 can be the same as or similar to and of the needle hub subassemblies or assemblies described herein. As shown in FIG. 29, the applicator 1550 includes a first housing portion 1552A and a second housing portion 1552B. The first housing portion 1552A and the second housing portion 1552B can be coupled together such that the first housing portion 1552A and the second housing portion 1552B form a connection region 1555. The connection region 1555 can be coupled to a proximal end of the needle hub subassembly 1500. As shown in FIG. 29, the needle hub subassembly 1500 includes an open-ended needle cap 1510, a needle 1530, a needle bushing 1541, and an implant chamber hub 1520 (also referred to as a needle hub). Although not shown, the needle hub assembly 1500 can also include a secondary push wire assembly.

The first housing portion 1552A and the second housing portion 1552B can be coupled by engaging a first fastener 1551A and a second fastener 1551B with a third fastener 1553A and a fourth fastener 1553B, respective. The first fastener 1551A and the second fastener 1551B can be, for example, a thread insert. The third fastener 1553A and the fourth fastener 1553B can be, for example, a socket head cap screw. Alternatively, the first housing portion 1552A and the second housing portion 1552B can be coupled via any suitable attachment mechanism, such as, for example, adhesive.

Additionally, the first housing portion 1552A and the second housing portion 1552B can be formed via any suitable material. For example, the first housing portion 1552A and the second housing portion 1552B can be formed of injection molding grade ABS with medium impact and high gloss.

The applicator 1550 also includes a wheel subassembly. The wheel subassembly includes a wheel axle 1566 and a wheel hub 1565. The wheel subassembly also includes a first wheel rim 1567A and a second wheel rim 1567B. The wheel axle 1566 can be disposed within a central opening of the wheel hub 1565. For example, the wheel axle 1566 can be press fit into the central opening of the wheel hub 1565. The first wheel rim 1567A and the second wheel rim 1567B can be disposed on either side of the wheel hub 1565. For example, the first wheel rim 1567A and the second wheel rim 1567B can be press fit onto the wheel hub 1565. The first wheel rim 1567A and the second wheel rim 1567B can include notches or grooves spaced evenly along the outer surface of the first wheel rim 1567A and the second wheel rim 1567B. The first housing portion 1552A and the second housing portion 1552B can each include an axle recess such that the wheel axle 1566 can be rotatably engaged with the axle recesses of the first housing portion 1552A and the second housing portion 1552B. Therefore, the wheel subassembly can rotate relative to the axle recesses of the first housing portion 1552A and the second housing portion 1552B.

The applicator 1550 can also include a shuttle including a shuttle closure 1561 and a shuttle base 1563. A thread 1556 can be looped around a groove in the shuttle closure 1561 and/or the shuttle base 1563. Each end of the thread 1556 can then be coupled to the wheel hub 1565. Specifically, each end of the thread 1556 can be coupled to a pocket formed in the wheel hub 1565. The thread 1556 can be made of, for example, Kevlar. In some embodiments, the loop pulls on 1561/1563 when the wheel is turned, urging the pusher wire to move forward.

The applicator 1550 can also include a dog bone spring 1564 with a first end and a second end. The first end of the dog bone spring 1564 can be securely coupled between the shuttle closure 1561 and the shuttle base 1563. The second end of the dog bone spring 1564 can be coupled to a dog bone anchor 1554, which is fixedly coupled to the first housing portion 1552A and/or the second housing portion 1552B. The dog bone spring 1564 can be formed of any suitable material, such as, for example, food grade rubber. Although described as a dog bone spring, any suitable spring can be used in the applicator 1550.

A pawl 1558 can be secured within the first housing portion 1552A and/or the second housing portion 1552B. The pawl 1558 can be disposed relative to the first wheel rim 1567A and the second wheel rim 1567B of the wheel subassembly such that the pawl 1558 can engage with the notches or grooves formed in the first wheel rim 1567A and the second wheel rim 1567B. The pawl 1558 can engage with the notches or grooves such that the wheel subassembly can be moved in one direction by the user (e.g., by a user's thumb), and the pawl 1558 prevents rotation in an opposite direction by engaging a notch or groove of the first wheel rim 1567A and the second wheel rim 1567B against the force of the dog bone spring 1564, which pulls the shuttle proximally.

The applicator 1550 can also include an uncoated pusher wire 1559 and a pusher stop 1568. The pusher wire 1559 has a first end and a second end. The first end of the pusher wire 1559 can be secured between the shuttle closure 1561 and the shuttle base 1563. In some embodiments, when the wheel is rotated, the shuttle is pulled distally, moving the pusher wire distally and into the needle hub to push out the implant. The second end of the pusher wire 1559 can be threaded through the connection region 1555 and into a proximal end of the needle hub subassembly 1500. The pusher wire 1559 can be formed of, for example, stainless steel. The pusher stop 1568 can be disposed at any suitable location along the length of the pusher wire 1559 depending on the length of the needle 1530. In some embodiments, a pusher stop can be used to prevent the pusher wire 1559 from extending beyond the distal end of the needle. In such embodiments, the pusher stop can be configured to engage such that when the pusher stop is reached, the pusher wire 1559 cannot move any farther distally.

FIG. 30 is a cross-sectional side view of the applicator 1550 with the first wheel rim 1567A and the second wheel rim 1567B of the wheel subassembly removed. As shown in FIG. 30, the applicator 1550 includes a thumb engagement portion 1569. The thumb engagement portion 1569 defines a recess for projection of the wheel subassembly in a fully assembled configuration such that a user can access the first wheel rim 1567A and the second wheel rim 1567B of the wheel subassembly to rotate the wheel subassembly. Additionally, a distal portion of the thumb engagement portion 1569 can have a smaller distance to a centerline of a lumen of the connection region 1555 than a proximal portion of the thumb engagement portion 1569 to ease in forward rotation of the wheel subassembly. For example, a first vertical distance $d_1$ from a centerline C of the lumen of the connection region 1555 to point D in FIG. 30 can be about 3.379, and a second vertical distance $d_2$ from the centerline C to point E in FIG. 30 can be about 3.452.

Figure 31A:
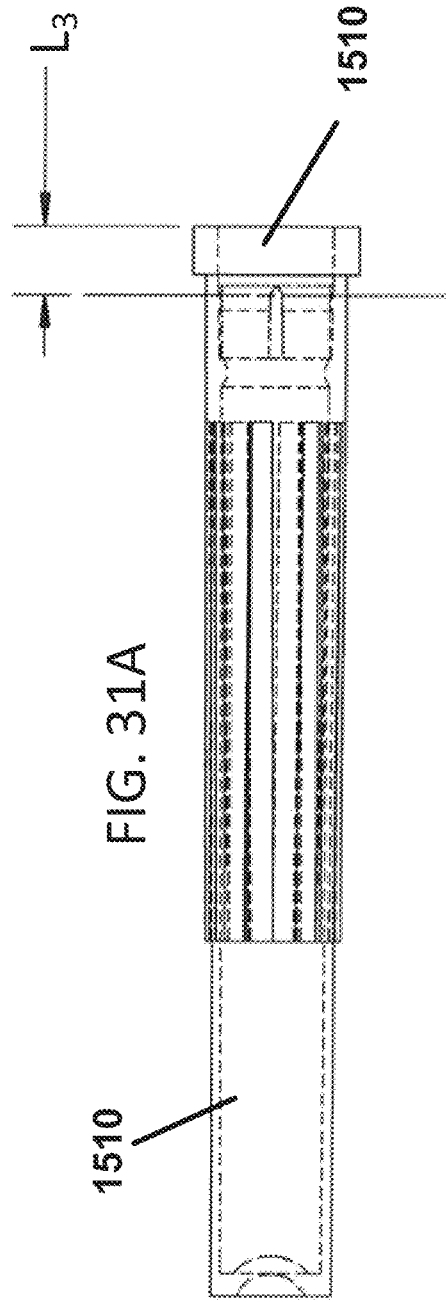
FIG. 31A is a side view of the needle cap of FIG. 29 in a first configuration, according to an embodiment.
Figure 31B:
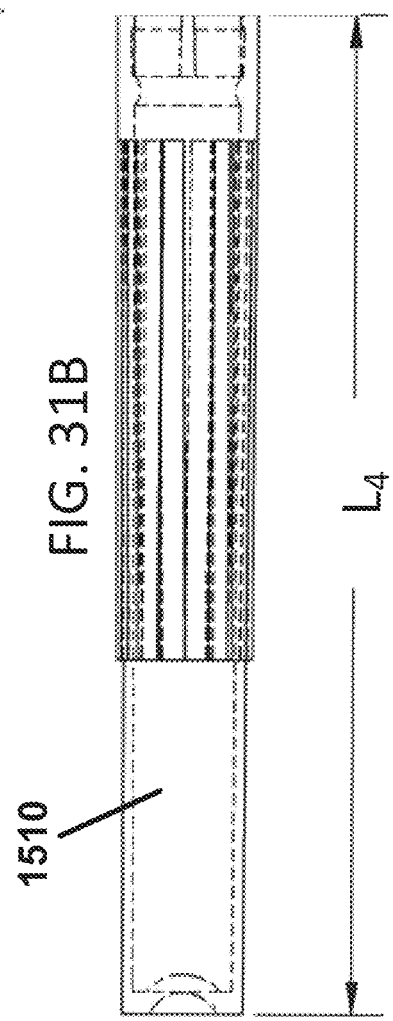
FIG. 31B is a side view of the needle cap of FIG. 31A in a second configuration.

FIG. 31A is a side view of the needle cap 1510 in a first configuration. As shown in FIG. 31A, the needle cap 1510 has a proximal portion 1571 that is configured to be removed before use of the needle cap 1510. The proximal portion 1571 has a length $L_3$. The length $L_3$ can be, for example, about 3.51 millimeters. FIG. 31B is a side view of the needle cap 1510 in a second configuration with the proximal portion 1571 removed. After removal of the proximal portion 1571, the proximal edge can be deburred. As shown in FIG. 31B, the needle cap 1510 in the second configuration can have a length $L_4$. The length $L_4$ can be, for example, about 51.02 millimeters.

FIGS. 32A-C are a side view, a top view, and a perspective view of the needle 1530, respectively. The needle 1530 can have an overall length $L_5$. The length $L_5$ can be, for example, about 0.470 inches. In other embodiments, the length $L_5$ can be, for example, about 0.467 inches. Additionally, the needle 1530 can be, for example, 27 gauge. The structure and function of the needle 1530 can be similar to or the same as the structure and function of any of the needles described herein. For example, the needle 1530 can have a beveled end and a non-beveled end. The non-beveled end can be deburred such that it is substantially burr free.

Figure 33A:
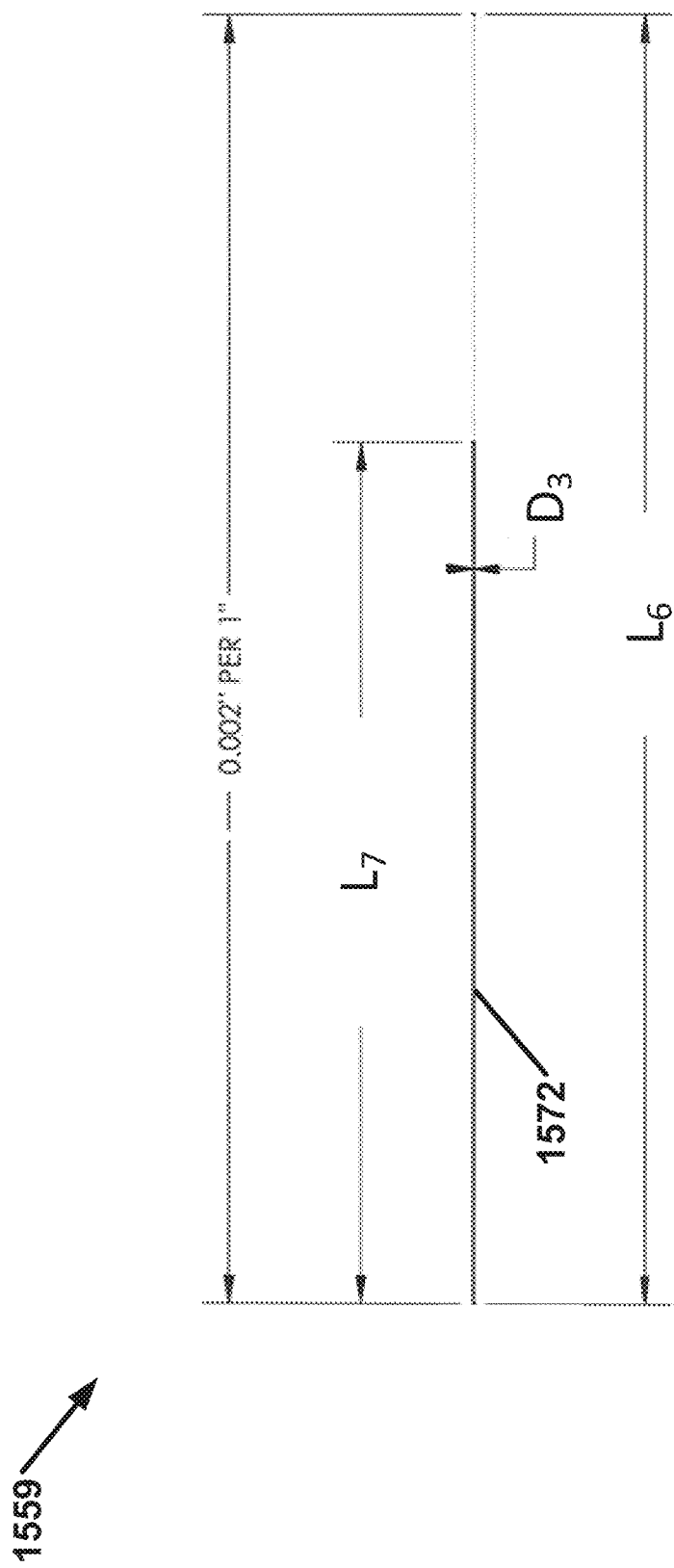
FIG. 33A is a side view of the pusher wire of FIG. 29, according to an embodiment.

FIG. 33A is a side view of the pusher wire 1559. The pusher wire 1559 includes a coated portion 1572. The pusher wire can have an overall length $L_6$. The length $L_6$ can be, for example, about 3.00 inches. In some embodiments, the length $L_6$ can range from about 2.75 inches to about 3.25 inches. The coated portion 1572 can have a length $L_7$. The length $L_7$ can be, for example, about 2.000 inches. In some embodiments, the length $L_7$ can range from about 1.900 inches to about 2.100 inches. The diameter of the coated portion 1572 can be a diameter $D_3$. The diameter $D_3$ can be, for example, about 0.0090 inches. In some embodiments, the diameter $D_3$ can range from about 0.0086 inches to about 0.0094 inches. The coated portion 1572 can include an end of the pusher wire 1559 such that the end of the pusher wire 1559 is also fully coated. The coated portion 1572 can be coated with, for example, PTFE.

FIG. 33B is a side view of an alternative pusher wire 1559A. The pusher wire 1559A is uncoated. The pusher wire 1559A can have a length $L_9$ and a diameter $D_4$. The length $L_9$ can be, for example, about 2.123 inches. In some embodiments, the length $L_9$ can range from about 2.103 inches to about 2.143 inches. The diameter $D_4$ can be, for example, about 0.0197 inches. In some embodiments, the diameter $D_4$ can range from about 0.0193 inches to about 0.0201 inches.

Figures 34A, 34B, 34C, 34D:
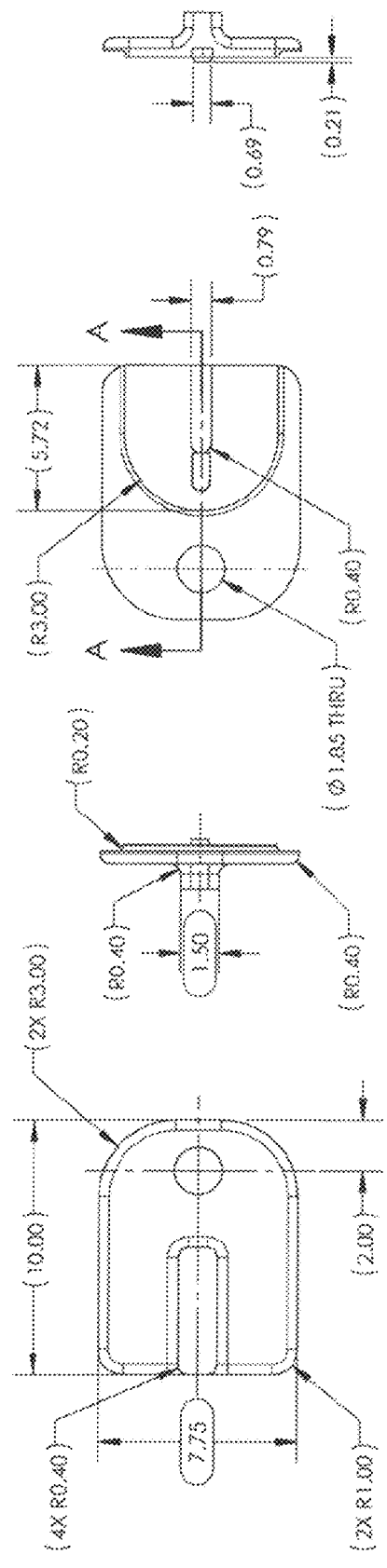
FIG. 34A is a top view of the shuttle closure of FIG. 29, according to an embodiment.
FIG. 34B is a side view of the shuttle closure of FIG. 34A.
FIG. 34C is a bottom view of the shuttle closure of FIG. 34A.
FIG. 34D is an alternative side view of the shuttle closure of FIG. 34A.
Figure 34E:
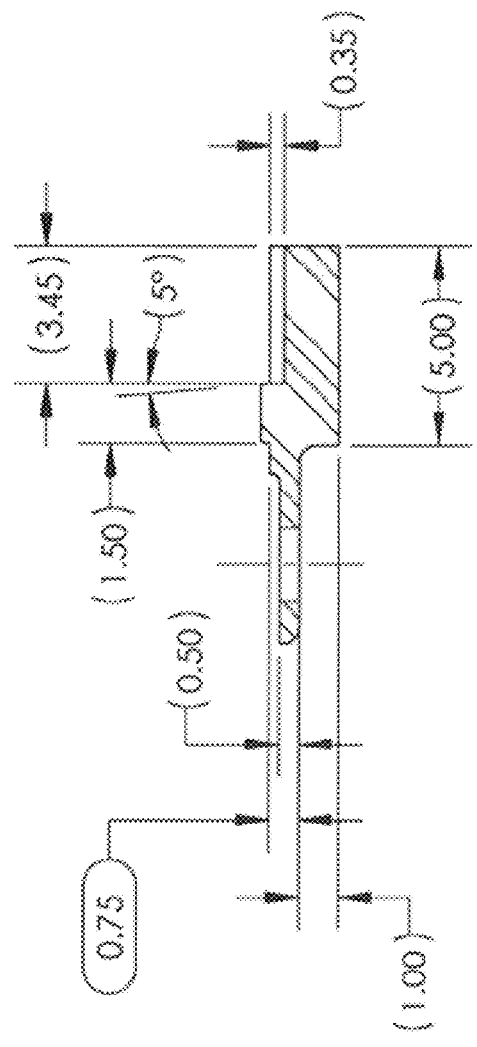
FIG. 34E is a cross-sectional view of the shuttle closure of FIG. 34A taken along line A-A in FIG. 34C.

FIG. 34A is a top view of the shuttle closure 1561. FIG. 34B is a side view of the shuttle closure 1561. FIG. 34C is a bottom view of the shuttle closure 1561. FIG. 34D is an alternative side view of the shuttle closure 1561. FIG. 34E is a cross-sectional view of the shuttle closure 1561 taken along line A-A in FIG. 34C.

FIG. 35A is a side view of the shuttle base 1563. FIG. 35B is a top view of the shuttle base 1563. FIG. 35C is a side view of the shuttle base 1563. FIG. 35D is a bottom view of the shuttle base 1563. FIG. 35E is a cross-sectional view of the shuttle base 1563 taken along line A-A in FIG. 35B.

Figure 36B:
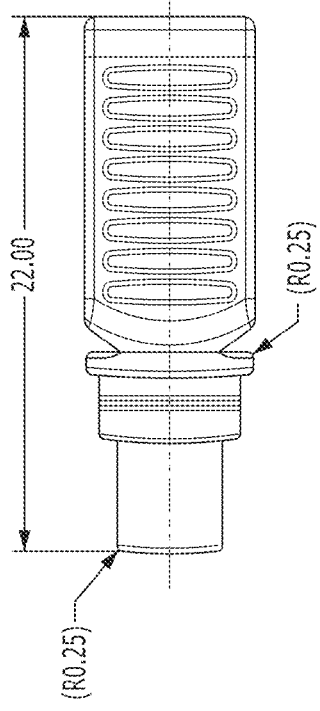
FIG. 36B is a top view of the implant chamber hub of FIG. 36A.
Figure 36C:
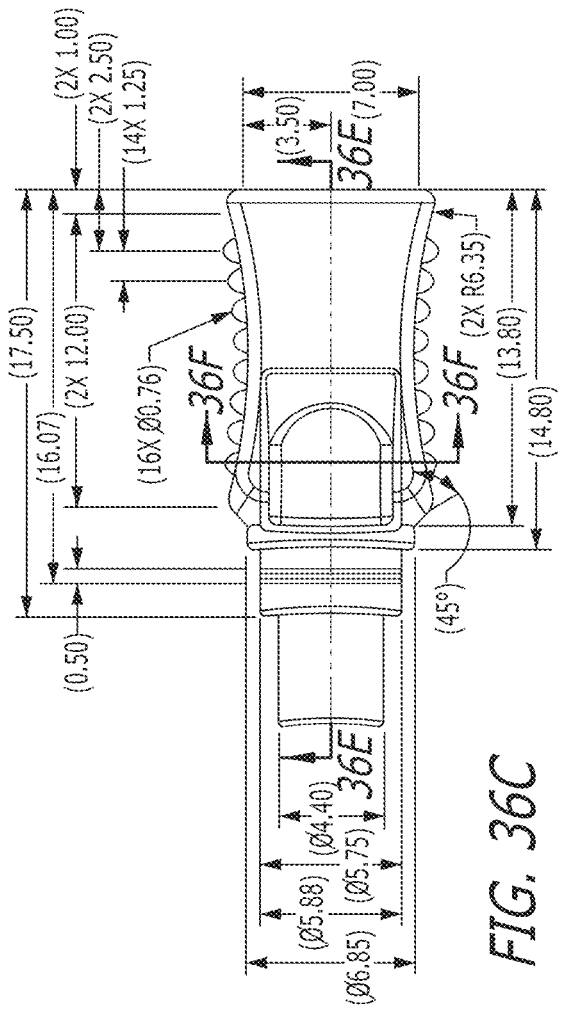
FIG. 36C is a side view of the implant chamber hub of FIG. 36A.
Figure 36A:
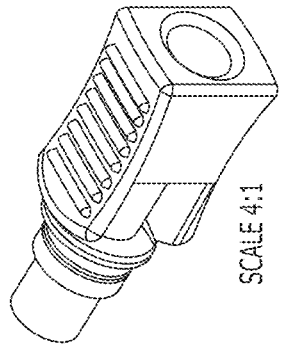
FIG. 36A is a perspective view of the implant chamber hub of FIG. 29, according to an embodiment.
Figure 36D:
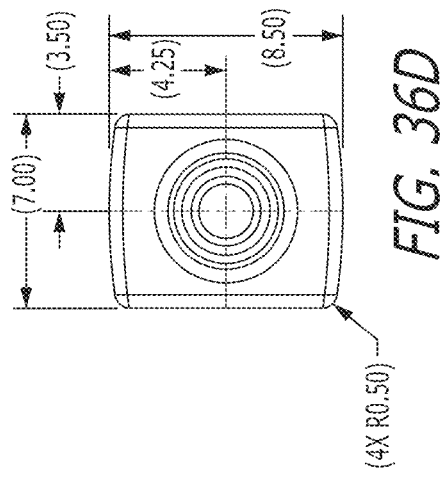
FIG. 36D is a distal end view of the implant chamber hub of FIG. 36A.
Figure 36F:
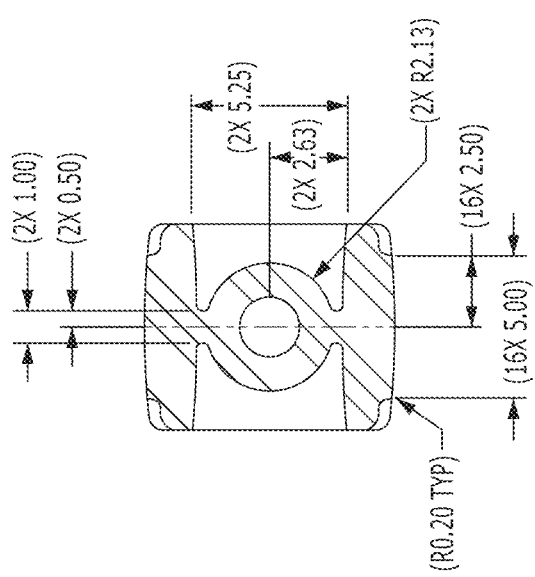
FIG. 36F is a cross-sectional view of the implant chamber hub of FIG. 36A taken along line B-B in FIG. 36C.
Figure 36E:
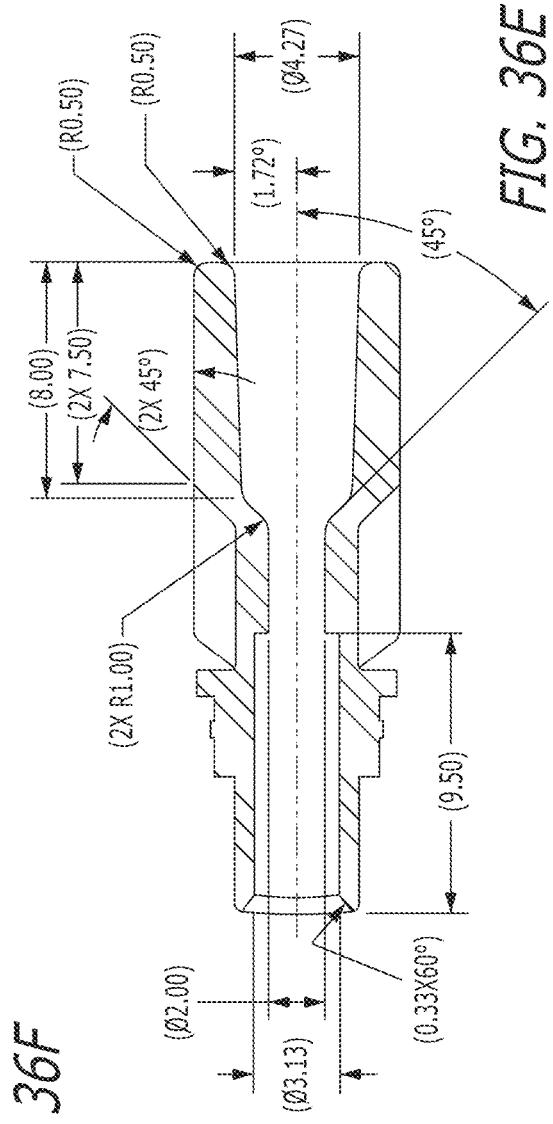
FIG. 36E is a cross-sectional view of the implant chamber hub of FIG. 36A taken along line A-A in FIG. 36C.

FIG. 36A is a perspective view of the implant chamber hub 1520. FIG. 36B is a top view of the implant chamber hub 1520. FIG. 36C is a side view of the implant chamber hub 1520. FIG. 36D is a distal end view of the implant chamber hub 1520. FIG. 36E is a cross-sectional view of the implant chamber hub 1520 taken along line A-A in FIG.

36C. FIG. 36F is a cross-sectional view of the implant chamber hub 1520 taken along line B-B in FIG. 36C.

FIG. 37A is a top view of the dog bone spring 1564. FIG. 37B is [a side view?] of the dog bone spring 1564. FIG. 37C is a cross-sectional view taken along line A-A in FIG. 37A. FIG. 37D is an enlarged view of Detail B in FIG. 37C.

Figure 38E:
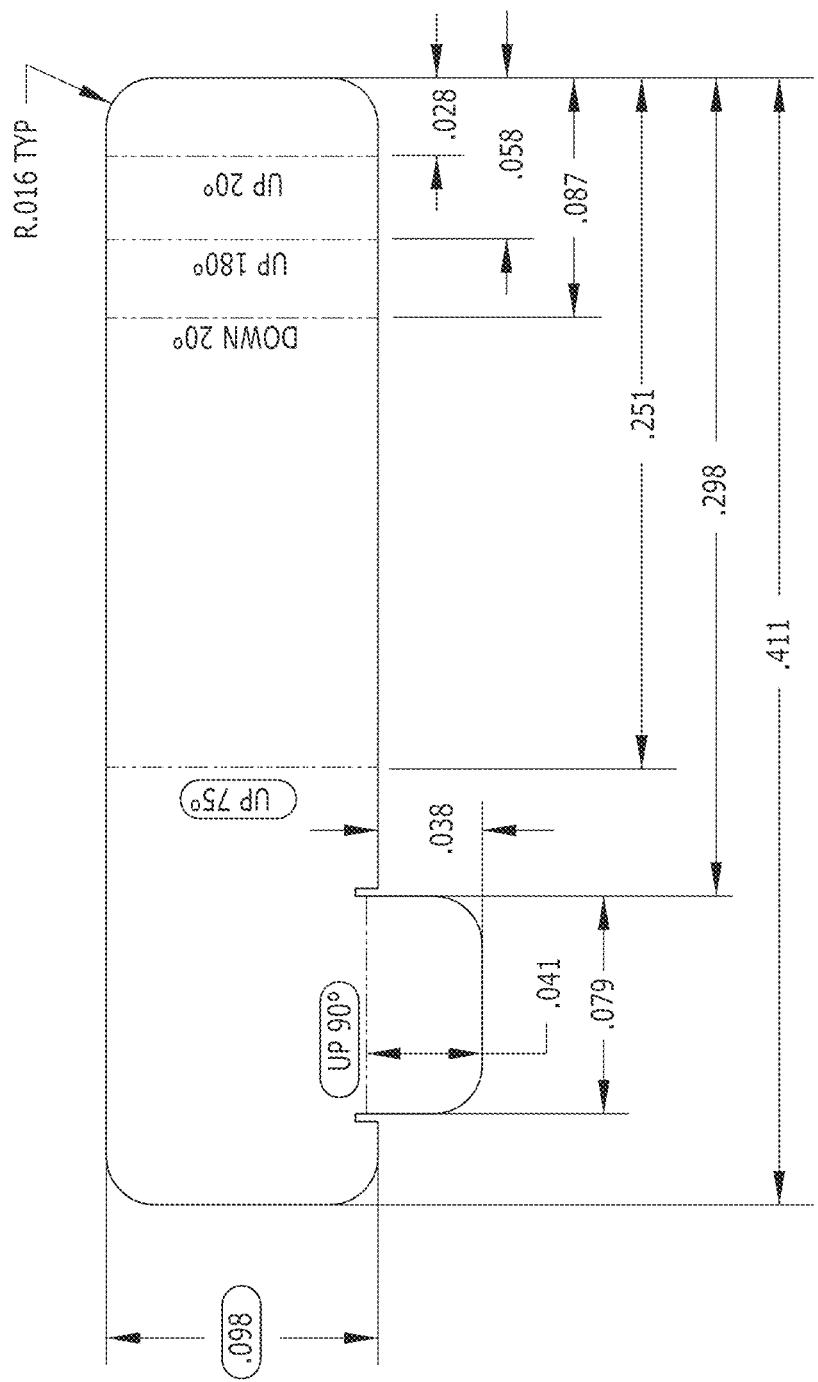
FIG. 38A is a perspective view of the pawl of FIG. 29, according to an embodiment.

FIG. 38A is a perspective view of the pawl 1558. FIG. 38B is a side view of the pawl 1558. FIG. 38C is a cross-sectional view of the pawl 1558 taken along line A-A in FIG. 38B. FIG. 38D is a side view of the pawl 1558 in a pre-bent configuration. FIG. 38E is a top view of the pawl 1558 in a pre-bent configuration. FIG. 38E includes instructions for bending portions of the pawl 1558 such that the pawl 1558 takes the form of FIGS. 38A-38D.

FIG. 39A is a perspective view of the wheel hub 1565. FIG. 39B is a side view of the wheel hub 1565. As shown in FIG. 39B, the wheel hub 1565 includes wheel hub pockets 1574. FIG. 39C is a side view of the wheel hub 1565 from the opposite side as FIG. 39B. FIG. 39D is a proximal end view of the wheel hub 1565. FIG. 39E is a distal end view of the wheel hub 1565.

FIG. 40A is a perspective view of the first wheel rim 1567A. FIG. 40B is a side view of the first wheel rim 1567A. FIG. 40C is a cross-sectional view of the first wheel rim 1567A taken along line A-A in FIG. 40B. FIG. 40D is an enlarged view of Detail C in FIG. 40C. FIG. 40E is an enlarged view of Detail D in FIG. 40B. FIG. 40F is an enlarged view of Detail E in FIG. 40B. FIG. 40G is a front view of the first wheel rim 1567A. FIG. 40H is a side view of the first wheel rim 1567A from the opposite side of FIG. 40B. FIG. 40I is a cross-sectional view taken along line B-B in FIG. 40H. FIG. 40J is an enlarged view of Detail F in FIG. 40H.

Although not shown, the second wheel rim 1567B can be identical to the first wheel rim 1567A.

FIG. 41 is a side view of a secondary pusher wire 1570 that can be included in the needle hub assembly 1500.

FIG. 42A is a top view of the first housing portion 1552A. FIG. 42B is a side view of the first housing portion 1552A. FIG. 42C is a bottom view of the first housing portion 1552A. FIG. 42D is a side view of the first housing portion 1552A from the opposite side of FIG. 42B. FIG. 42E is an enlarged view of Detail A in FIG. 42B. FIG. 42F is an enlarged view of Detail B in FIG. 42B. FIG. 42G is a cross-sectional view of the first housing portion 1552A taken along line C-C in FIG. 42B. FIG. 42H is a cross-sectional view of the first housing portion 1552A taken along line D-D in FIG. 42B. FIG. 42I is a cross-sectional view of the first housing portion 1552A taken along line O-O in FIG. 42B. FIG. 42J is a cross-sectional view of the first housing portion 1552A taken along line P-P in FIG. 42B. FIG. 42K is a distal end view of the first housing portion 1552A. FIG. 42L is a proximal end view of the first housing portion 1552A.

FIG. 43A is a top view of the second housing portion 1552B. FIG. 43B is a side view of the second housing portion 1552B. FIG. 43C is a bottom view of the second housing portion 1552B. FIG. 43D is a side view of the second housing portion 1552B from the opposite side of FIG. 43B. FIG. 43E is a cross-sectional view of the second housing portion 1552B taken along line A-A in FIG. 43B. FIG. 43F is a cross-sectional view of the second housing portion 1552B taken along line B-B in FIG. 43B. FIG. 43G is a cross-sectional view of the second housing portion 1552B taken along line C-C in FIG. 43B. FIG. 43H is a cross-sectional view of the second housing portion 1552B taken along line D-D in FIG. 43B. FIG. 43I is an enlarged view of Detail E in FIG. 43B. FIG. 43J is a distal end view of the second housing portion 1552B. FIG. 43K is a proximal end view of the second housing portion 1552B.

In use, the applicator 1550 can be operated by a trained healthcare provider such as, for example, an ophthalmologist. The needle 1530 can be loaded by a user or may be pre-loaded with one or more implants. The needle hub subassembly 1500 can then be operably coupled to the connection region 1555 of the applicator 1550. The applicator 1550 can be operated by rotating the wheel subassembly distally (i.e., rotating the first wheel rim 1567A and the second wheel rim 1567B). The rotation of the wheel subassembly causes the shuttle to move distally. Distal movement of the shuttle causes the shuttle to push the pusher wire 1559 distally into the needle hub 1520. Movement of the pusher wire 1559 distally into the needle hub 1520 can cause the pusher wire 1559 to move into a lumen of the needle 1530 and to engage with an implant loaded within a lumen of the needle 1530. Farther distal movement of the pusher wire 1559 (as a result of additional rotation of the wheel subassembly) can cause the pusher wire 1559 to push an implant from the distal end of the needle 1530. If more than one implant was loaded within the needle 1530, the pusher wire 1559 can optionally be moved farther distally to push additional implants from the distal end of the needle 1530. Said another way, the pusher wire 1559 can be extended from the applicator 1550 to a pre-determine position, allowing for control over the injection of an implant from the needle hub assembly 1500. Other benefits include no thread tangles and no overtravel of the pusher wire 1559. Additionally, a user can visually verify the distance from the pusher wire 1559 to the heel of the bevel.

The applicator 1550 can be a scroll-wheel actuated dry injector that utilizes the pusher wire 1559 (e.g., a stainless steel shaft) to eject, implants from the lumen of the applicator needle. The applicator 1550 can be used to deliver, for example, an ENV515 (travoprost) intracameral implant for reduction of intraocular pressure in patients with glaucoma. ENV515 is a fully biodegradable extended-release formulation of a marketed prostaglandin analogue travoprost with the potential to significantly limit disease progression and vision loss through improved safety, efficacy, and patient compliance. The applicator 1550 can be used to insert ENV515 (travoprost) intracameral implants into the anterior chamber of the eye. The applicator 1550 is a needle-based injector and is intended to be a single use, disposable instrument.

Implants can be loaded into the applicator 1550 immediately prior to use. Alternatively, the sterile ENV515 implants can be preloaded into the applicator 1550, with the needle hub assembly 1520 of the applicator 1550 functioning as a container closure for the implants. The implant will be placed in the eye during an office procedure, where an ophthalmologist may use a slit lamp or operating scope or other means of magnification and the applicator for insertion of ENV515 biodegradable implant into the eye.

In one embodiment, the applicator 1550 can be used to deliver a drug to an eye of a patient. According to one embodiment, the applicator 1550 can be used, for example, by first treating the patient's ocular surface with topical anesthetic (for example, proparacaine 0.5% or equivalent). Next, the patient's ocular surface can be treated with povidone iodide. After two minutes, a lid speculum can be inserted. Then, implant(s) can be administered into the anterior chamber via intracameral injection through clear, peripheral cornea using the applicator 1550. The needle 1530 should be advanced parallel with the iris, about 1 mm anterior to the limbus with the patient sitting at the slit lamp, or with the patient supine under the operating scope.

FIG. 44 is an exploded perspective view of an injector assembly 1602.

FIG. 45A is a top view of the injector assembly 1602.

FIG. 45B is a side view of the injector assembly 1602.

FIG. 46 is an exploded perspective view of an injector assembly 1702.

FIG. 47A is a top view of the injector assembly 1702.

FIG. 47B is a side view of the injector assembly 1702.

FIG. 48A is a perspective view of the needle hub 1720. FIG. 48B is a top view of the needle hub 1720. FIG. 48C is a side view of the needle hub 1720. FIG. 48D is a distal end view of the needle hub 1720. FIG. 48E is a proximal end view of the needle hub 1720. FIG. 48F is a cross-sectional view taken along line A-A in FIG. 48C. FIG. 48G is a cross-sectional view of the needle hub 1720 taken along line B-B in FIG. 48F.

FIG. 49A is a side view of the open-ended cap 1710. FIG. 49B is a distal end view of the open-ended cap 1710. FIG. 48C is a proximal end view of the open-ended cap 1710. FIG. 48D is a cross-sectional view of the open-ended cap 1710 taken along line A-A in FIG. 49A.

FIG. 50A is a side view of the open-ended cap plug 1712. FIG. 50B is a distal end view of the open-ended cap plug 1712. FIG. 50C is a proximal end view of the open-ended cap plug 1712. FIG. 50D is a cross-sectional view of the open-ended cap plug 1712 taken along line A-A in FIG. 50A.

FIG. 51A is a top view of the first housing portion 1752A. FIG. 51B is a side view of the first housing portion 1752A. FIG. 51C is a bottom view of the first housing portion 1752A. FIG. 51D is a side view of the first housing portion 1752A from the opposite side of FIG. 51B. FIG. 51E is an enlarged view of Detail A in FIG. 51B. FIG. 51F is an enlarged view of Detail B in FIG. 51B. FIG. 51G is a cross-sectional view of the first housing portion 1752A taken along line C-C in FIG. 51B. FIG. 51H is a cross-sectional view of the first housing portion 1752A taken along line D-D in FIG. 51B. FIG. 51I is a cross-sectional view of the first housing portion 1752A taken along line O-O in FIG. 51B. FIG. 51I is a cross-sectional view of the first housing portion 1752A taken along line P-P in FIG. 51B. FIG. 51K is a distal end view of the first housing portion 1752A. FIG. 51L is a proximal end view of the first housing portion 1752A.

FIG. 52A is a top view of the second housing portion 1752B. FIG. 52B is a side view of the second housing portion 1752B. FIG. 52C is a bottom view of the second housing portion 1752B. FIG. 52D is a side view of the second housing portion 1752B from the opposite side of FIG. 52B. FIG. 52E is a cross-sectional view of the second housing portion 1752B taken along line A-A in FIG. 52B. FIG. 52F is a cross-sectional view of the second housing portion 1752B taken along line B-B in FIG. 52B. FIG. 52G is a cross-sectional view of the second housing portion 1752B taken along line C-C in FIG. 52B. FIG. 52H is a cross-sectional view of the second housing portion 1752B taken along line D-D in FIG. 52B. FIG. 52I is an enlarged view of Detail E in FIG. 52B. FIG. 52J is a distal end view of the second housing portion 1752B. FIG. 52K is a proximal end view of the second housing portion 1752B.

In some embodiments, a delivery device can include an elongated body member. The elongated body member can define a longitudinal axis along the longest dimension of the elongated body member. The elongated member can also define a top-plane for engaging a user, and, when engaged by a user, the elongated member can comprise a proximal end nearest the user and a distal end farthest from the user. The delivery device can also include a cannula having an inner diameter and defining a longitudinal axis along the centerline of the cannula. The longitudinal axis can be oriented substantially parallel with the longitudinal axis of the elongated body member. In some embodiments, the longitudinal axis of the cannula is not more than 7 millimeters below the top-plane of the elongated body member near the distal end of the elongated body member.

In some embodiments, the delivery device includes a plunger. The plunger is configured to translate through the inner diameter of the cannula along the longitudinal axis of the cannula. Upon translation along the longitudinal axis of the cannula, the plunger can push cargo along the inner diameter of the cannula. The delivery device can also include a movable member configured to move the plunger along the longitudinal axis of the cannula.

In some embodiments, the longitudinal axis of the cannula is not more than 5 millimeters below the top-plane of the elongated body member. In other embodiments, the longitudinal axis of the cannula is about 4 millimeters below the top-plane of the elongated body member. In other embodiments, the longitudinal axis of the cannula is about 3.5 millimeters below the top-plane of the elongated body member. In still other embodiments, the longitudinal axis of the cannula is between 5 and 0.5 millimeters below the top-plane of the elongated body member. In other embodiments, the longitudinal axis of the cannula is between 5 and 3 millimeters below the top-plane of the elongated body member.

In some embodiments, the movable member extends not more than 2 millimeters above the top-plane of the elongated body member. In other embodiments, the movable member extends not more than 1 millimeter above the top-plane of the elongated body member. In some embodiments, the movable member extends not more than 0.5 millimeter above the top-plane of the elongated body member.

The movable member can comprise a user engagement point. In some embodiments, the user engagement point of the movable member can be between 2 millimeters below and 2 millimeters above the top-plane of the elongated body member. In other embodiments, the movable member can be between 1 millimeter below and 1 millimeter above the top-plane of the elongated body member.

The movable member can comprise a wheel for rotation by the user. The wheel can be ratcheted and can be movable in one direction of rotation. The wheel can comprise a groove in axial alignment with the longitudinal axis of the cannula. The plunger can pass through the groove. The cannula can reside in the groove. The cannula can be smaller than a 22 or 25 gauge needle. For example, in some embodiments, the cannula can be a 27 or 30 gauge ultrathin walled needle. The movable member can be configured for rotational movement such that rotation of the movable member is translated into linear movement of the plunger.

In another embodiment, a delivery device can comprise an elongated body member. The elongated body member can define a longitudinal axis along its longest dimension and a top-plane for engaging a user. When engaged by a user, the elongated body member can include a proximal end nearest the user and a distal end farthest from the user. The delivery device can also include a plunger having a longitudinal axis and being configured to translate through the elongated body member in axial alignment with the elongated body member. In some embodiments, the plunger is not more than 7 millimeters below the top-plane of the elongated body member near the distal end of the elongated body member.

The delivery device can also include a movable member configured to move the plunger along its longitudinal axis.

The delivery device can also include a removable needle hub configured and dimensioned to removably engage the distal end of the elongated body member. The removable needle hub can comprise a cannula coupled with a needle hub. The cannula can be in axial alignment with the plunger of the delivery device when the needle hub is engaged with the distal end of the delivery device. Additionally, the plunger can axially translate through the cannula upon operation of the movable member by a user.

The needle hub can include a bevel indicator in positional alignment with a bevel on the distal end of the cannula.

In some embodiments, the longitudinal axis of the plunger is not more than 5 millimeters below the top-plane of the elongated body member. In some embodiments, the longitudinal axis of the plunger is about 4 millimeters below the top-plane of the elongated body member. In some embodiments, the longitudinal axis of the plunger is about 3.5 millimeters below the top-plane of the elongated body member. In some embodiments, the longitudinal axis of the plunger is between 5 and 0.5 millimeters below the top-plane of the elongated body member. In some embodiments, the longitudinal axis of the plunger is between 5 and 3 millimeters below the top-plane of the elongated body member.

In some embodiments, the movable member extends not more than 2 millimeters above the top-plane of the elongated body member. In some embodiments, the movable member extends not more than 1 millimeter above the top-plane of the elongated body member. In some embodiments, the movable member extends not more than 0.5 millimeter above the top-plane of the elongated body member.

In some embodiments, the movable member includes a user engagement point. In some embodiments, the user engagement point of the movable member is between 2 millimeters below and 2 millimeters above the top-plane of the elongated body member. In other embodiments, the user engagement point of the movable member is between 1 millimeter below and 1 millimeter above the top-plane of the elongated body member.

The movable member can comprise a wheel for rotation by the user. The wheel can be ratcheted and can be movable in one direction of rotation. The wheel can comprise a groove in axial alignment with the longitudinal axis of the plunger. The plunger can reside in the groove. The cannula can be smaller than a 25 gauge needle. For example, in some embodiments, the cannula is a 27 gauge ultrathin walled needle. The movable member can be configured for rotational movement such that rotation of the movable member is translated into linear movement of the plunger.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

At least some of the embodiments disclosed above, in particular at least some of the methods/processes disclosed, may be realized in circuitry, computer hardware, firmware, software, and combinations thereof (e.g., a computer system). Such computing systems, may include PCs (which may include one or more peripherals well known in the art), smartphones, specifically designed medical apparatuses/devices and/or other mobile/portable apparatuses/devices. In some embodiments, the computer systems are configured to include clients and servers. A client and server are generally remote from each other and typically interact through a communication network (e.g., VPN, Internet). The relationship of client and server arises by virtue of computer programs running on the respective computers and having a client-server relationship to each other.

Some embodiments of the disclosure (e.g., methods and processes disclosed above) may be embodied in a computer program(s)/instructions executable and/or interpretable on a processor, which may be coupled to other devices (e.g., input devices, and output devices/display) which communicate via wireless or wired connect (for example).

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, the terms "about" and "approximately" generally mean plus or minus 10% of the value stated, for example about 250 μm would include 225 μm to 275 μm, about 1,000 μm would include 900 μm to 1,100 μm. It is to be understood that the dimensions discussed herein may be, in some embodiments, relative, and not absolute, such that ratios present in an example embodiment given in inches may be generalized to other units and/or scales.

While various embodiments of the system, methods and devices have been described above, it should be understood that they have been presented by way of example only, and not limitation. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

Applicator Handle Sub-Assembly Example

The Applicator Finished Assembly includes all components, and is a finished assembly that is packaged and sterilized. It is anticipated that the following order of assembly will be conducted:

1. Cut Kevlar thread to length
2. Knot ends of thread (e.g., KEVLAR thread)
3. Press fit wheel axle into the Wheel Hub
4. Align/press fit each Wheel Rim to the Wheel Hub using alignment features
5. Secure with adhesive
6. Repeat steps 4 and 5 for second Wheel Rim
7. Insert Kevlar ends into the pocket of the Wheel Hub
8. Glue Kevlar ends
9. Wrap Kevlar thread around the groove in the shuttle
10. Place Dogbone Spring onto post in Shuttle Base
11. Glue the Shuttle Closure over the Shuttle Base
12. Place one side of Pusher Wire into Shuttle and glue in place
13. Press thread inserts into Right Side Handle Half
14. Place Pawl into Right Side Handle Half
15. Glue Pawl to secure
16. Insert Pin (e.g., 1554 and/or Dogbone anchor) into the Right Side Handle Half
17. Insert wheel/shuttle sub-assembly into Right Side Handle Half
18. Twist Dogbone Spring over Pin
19. Close assembly with Left Side Handle Half
20. Secure handle with Cap Screws
21. Package in gamma sterilization compatible pouch Implant Stability Sub-Assembly Example The Implant Stability Sub-Assembly includes the following components, making up a sub-assembly which is packaged and sterilized.

Secondary Push Wire Assembly
Needle
Needle Hub
Open Ended Cap

The following order of assembly can be followed:

1. Cut Needle to length (or choose appropriate needle length)
2. Attach (e.g., glue) Needle into Needle Hub (orientation of the needle bevel based on notch on Hub)
3. Fix the Secondary Pusher End and the Secondary Pusher Stop to the Secondary Pusher Wire.
4. Slide the Secondary Pusher Wire sub-assembly into the Needle Hub
5. Verify depth of insertion
6. Insert needle assembly into Open Ended Cap
7. Package into tray (multiple per tray) with the Open Ended Cap Plug and heat seal tray closed
8. Sterilize sealed trays The device can include several custom metal or machined components.

Example Functionality i. Extension of the pusher wire to a pre-determined position
ii. No thread tangles
iii. No overtravel
iv. Smooth functioning v. Depth of pusher wire in needle hub assembly
   1. Verification of the distance from the pusher wire to the heel of the bevel Example Visual Inspections vi. Needle bevel alignment
vii. Needle straightness
viii. Needle sharpness
ix. Burrs on metal components
x. Particulates
xi. Adhesive blooming
xii. Water stains (washed components)

We claim:

1. An apparatus, comprising:
   a first cap;
   a second cap including a proximal end, a distal end, and a longitudinal axis;
   a needle hub connected to the second cap;
   a pusher wire and a pusher wire connector disposed within the needle hub;
   a needle including a first beveled end configured to receive an implant, and a second end disposed within a hub pocket of the needle hub, the first cap connected to the needle hub and disposed at a proximal end of the second cap, wherein the pusher wire, the pusher wire connector, and the needle are substantially aligned with one another along the longitudinal axis of the second cap; and
   an applicator including a wheel axle and a wheel hub operably configured to move a shuttle using a thread connected to the wheel hub and the shuttle, wherein movement of the shuttle causes movement of the pusher wire.

2. The apparatus of claim 1, wherein the pusher wire is dimensioned such that it can be received in the bore of the needle.

3. The apparatus of claim 1, wherein the pusher wire is configured to engage, upon attachment to the applicator and during use, with an actuator the shuttle of the applicator.

4. The apparatus of claim 1, further comprising at least one implant disposed within the needle, wherein the applicator is configured to advance, during use, a single implant through the beveled end of the needle upon a predetermined partial rotation of a wheel rim associated with the wheel axle and the wheel hub.

5. The apparatus of claim 4, wherein the implant is a medical implant.

6. The apparatus of claim 4, wherein the implant is an ocular implant.

7. The apparatus of claim 4, wherein the implant is an intracameral implant.

8. The apparatus of claim 4, wherein the implant is a biodegradable implant.

9. The apparatus of claim 4, wherein the implant is a sterile implant.

10. The apparatus of claim 4, wherein the implant includes travoprost.

11. The apparatus of claim 1, wherein the second cap comprises a bristle retainer at least partially disposed therewithin at the distal end thereof, the bristle retainer having a bristle at least partially disposed therewithin;
    wherein the needle hub is at least partially disposed within the second cap;
    the apparatus further comprising at least one implant disposed within the needle.

12. The apparatus of claim 11, wherein the bristle retainer includes a bristle retainer hub having one or more ribs on an exterior surface thereof, the one or more ribs configured to interference fit with the second cap.

13. The apparatus of claim 11, wherein the needle hub includes one or more ribs on an exterior surface thereof, the one or more ribs configured for interference fit with the second cap.

14. The apparatus of claim 11, wherein the needle and the needle hub are connected to one another.

15. The apparatus of claim 11, wherein the needle and the needle hub are connected to one another with an adhesive.

16. The apparatus of claim 11, wherein the bristle is partially fixed within the bristle retainer.

17. The apparatus of claim 11, wherein the bristle is partially fixed within the bristle retainer with an adhesive.

18. The apparatus of claim 1, wherein:
    the second cap includes a bristle retainer at least partially disposed therewithin at the distal end thereof, the bristle retainer having a bristle at least partially disposed therewithin; and
    at least one implant disposed within the needle, and the needle and the at least one implant are substantially aligned with one another along the longitudinal axis of the cap.

19. The apparatus of claim 18, wherein the applicator comprises a handle that is configured to actuate, and the pusher wire is configured such that, with each actuation of the applicator handle during use, a single implant disposed within the bore of the needle is linearly advanced.

20. The apparatus of claim 18, wherein
    the bristle retainer is at least partially disposed within at the distal end of the second cap;
    the needle includes a bore that runs longitudinally from the first end to the second;
    the second end of the needle is partially disposed within the hub pocket and is opposite to the connection of the applicator to the needle hub; and
    wherein at least one implant is disposed longitudinally within the needle bore.

21. The apparatus of claim 1, wherein:
    the first cap includes a proximal end and a distal end;
    the needle hub includes a distal end, a proximal end and a hub pocket contained within the needle hub;
    such that:
    (a) the second end of the needle is disposed within the hub pocket of the needle hub;
    (b) the first cap is cooperatively engaged with the needle hub;
    (c) the second end of the needle is partially disposed within the hub pocket;
    (d) the second cap is reversibly connected to the needle hub and disposed at the distal end of the first cap such that when the proximal end of the second cap is reversibly connected to the needle hub, the beveled end of the needle is disposed within the second cap; and
    (e) the pusher wire, the pusher wire connector, and the needle are substantially aligned with one another along the longitudinal axis of the second cap.

* * * * *